United States Patent
Dlugos, Jr. et al.

(10) Patent No.: US 8,523,885 B2
(45) Date of Patent: *Sep. 3, 2013

(54) IMPLANTABLE RESTRICTION SYSTEM WITH LOAD MONITOR

(75) Inventors: Daniel F. Dlugos, Jr., Middletown, OH (US); Wells D. Haberstich, Loveland, OH (US); Geoffrey C. Hueil, Mason, OH (US); Donna L. Korvick, Maineville, OH (US); Jeffrey D. Messerly, Cincinnati, OH (US); Kyle P. Moore, Mason, OH (US); Daniel J. Mumaw, Milford, OH (US); Mark S. Ortiz, Milford, OH (US); Frederick E. Shelton, IV, Hillsboro, OH (US); Patrick J. Swindon, Cincinnati, OH (US); Eric W. Thompson, Pleasant Plain, OH (US); Lauren S. Weaner, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 625 days.

This patent is subject to a terminal disclaimer.

(21) Appl. No.: 12/562,257

(22) Filed: Sep. 18, 2009

(65) Prior Publication Data

US 2011/0071553 A1    Mar. 24, 2011

(51) Int. Cl.
*A61B 17/12* (2006.01)

(52) U.S. Cl.
USPC ............................. 606/151; 600/37

(58) Field of Classification Search
USPC ................. 606/151, 157; 600/29–31, 37
See application file for complete search history.

(56) References Cited

U.S. PATENT DOCUMENTS

| | | | |
|---|---|---|---|
| 5,314,437 A * | 5/1994 | Holtsch | 606/157 |
| 5,704,893 A * | 1/1998 | Timm | 600/29 |
| 6,272,936 B1 | 8/2001 | Oreper et al. | |
| 6,547,801 B1 | 4/2003 | Dargent et al. | |
| 7,060,080 B2 * | 6/2006 | Bachmann | 606/151 |
| 7,238,191 B2 * | 7/2007 | Bachmann | 606/151 |
| 7,370,392 B2 * | 5/2008 | Holtsch | 24/170 |
| 7,879,068 B2 * | 2/2011 | Dlugos et al. | 606/201 |
| 7,901,419 B2 * | 3/2011 | Bachmann et al. | 606/157 |
| 7,972,346 B2 * | 7/2011 | Bachmann et al. | 606/151 |
| 8,012,162 B2 * | 9/2011 | Bachmann | 606/157 |
| 2005/0143765 A1 * | 6/2005 | Bachmann et al. | 606/157 |
| 2005/0143766 A1 * | 6/2005 | Bachmann et al. | 606/158 |
| 2006/0189888 A1 | 8/2006 | Hassler, Jr. et al. | |
| 2006/0199997 A1 * | 9/2006 | Hassler et al. | 600/37 |
| 2006/0211913 A1 | 9/2006 | Dlugos et al. | |
| 2007/0167672 A1 * | 7/2007 | Dlugos et al. | 600/37 |
| 2008/0097487 A1 * | 4/2008 | Pool et al. | 606/151 |

(Continued)

*Primary Examiner* — Julian Woo
*Assistant Examiner* — Christopher L Templeton
(74) *Attorney, Agent, or Firm* — Welsh Flaxman & Gitler LLC

(57) ABSTRACT

An apparatus for regulating the functioning of a patient's organ or duct includes an elongated member having a first end and a second end. A fastener is disposed on the first end of the elongated member. The fastener is configured to engage the second end of the elongated member so that the elongated member forms a loop around the organ or duct. A tension element is disposed for movement within the elongated member. A drive element is associated with and engages the tension element for causing the tension element to control the tension applied by the elongated member against a patient's body organ or duct. A load monitor ensures that excessive pressure is not applied to a patient's body organ or duct.

15 Claims, 39 Drawing Sheets

(56) References Cited

U.S. PATENT DOCUMENTS

| | | |
|---|---|---|
| 2008/0249806 A1 | 10/2008 | Dlugos et al. |
| 2009/0187202 A1 | 7/2009 | Ortiz et al. |
| 2011/0071341 A1* | 3/2011 | Dlugos et al. .................. 600/37 |
| 2011/0071557 A1* | 3/2011 | Dlugos et al. ................. 606/157 |
| 2011/0071558 A1* | 3/2011 | Dlugos et al. ................. 606/157 |
| 2011/0071646 A1* | 3/2011 | Dlugos et al. ............. 623/23.64 |

* cited by examiner

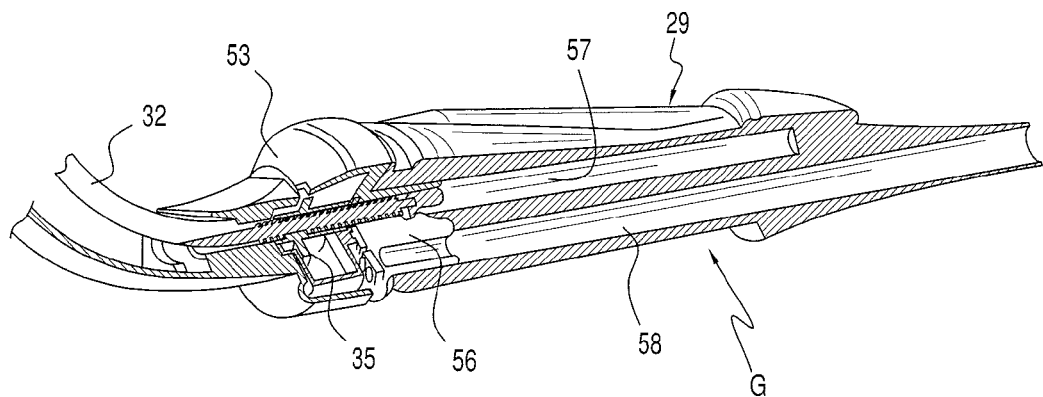
FIG. 21
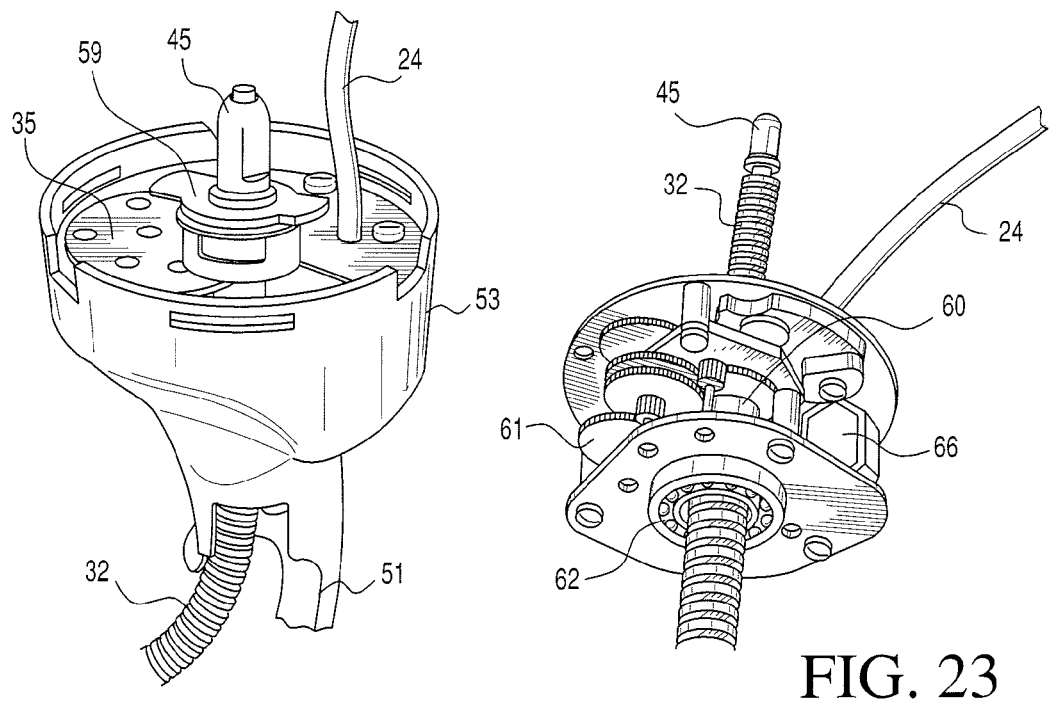
FIG. 22
FIG. 23

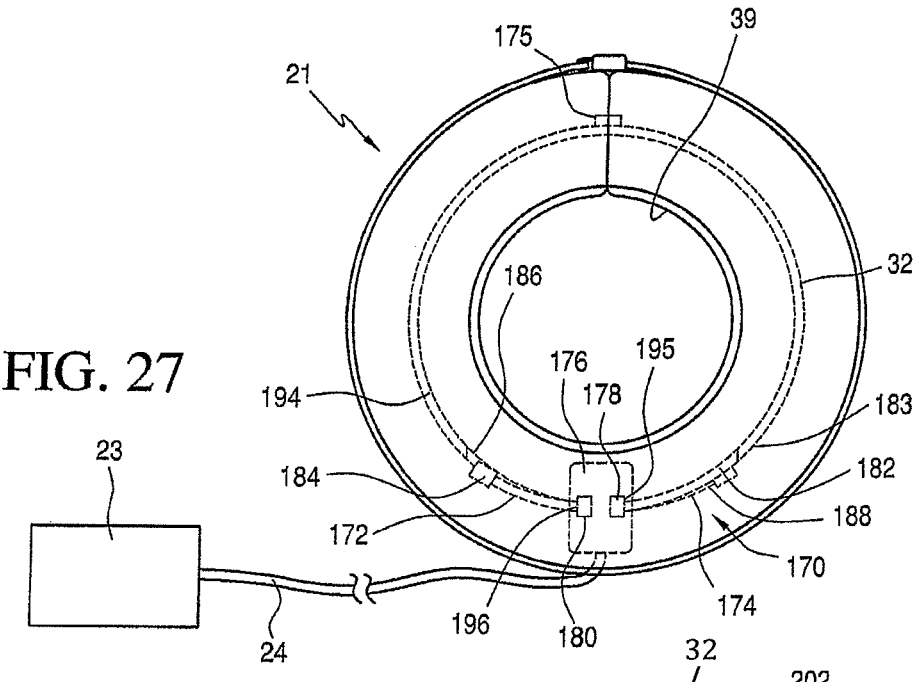
FIG. 27
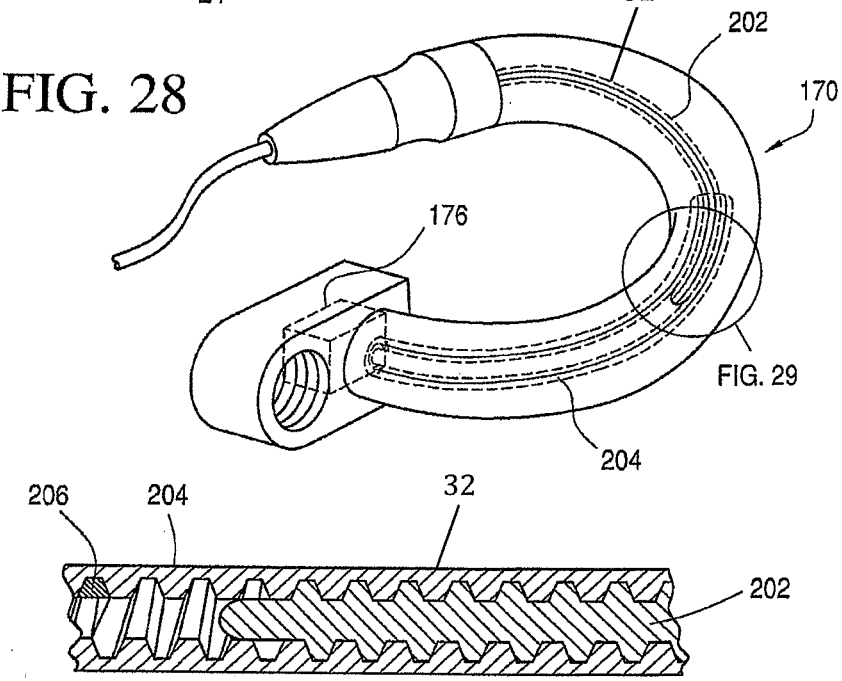
FIG. 28
FIG. 29

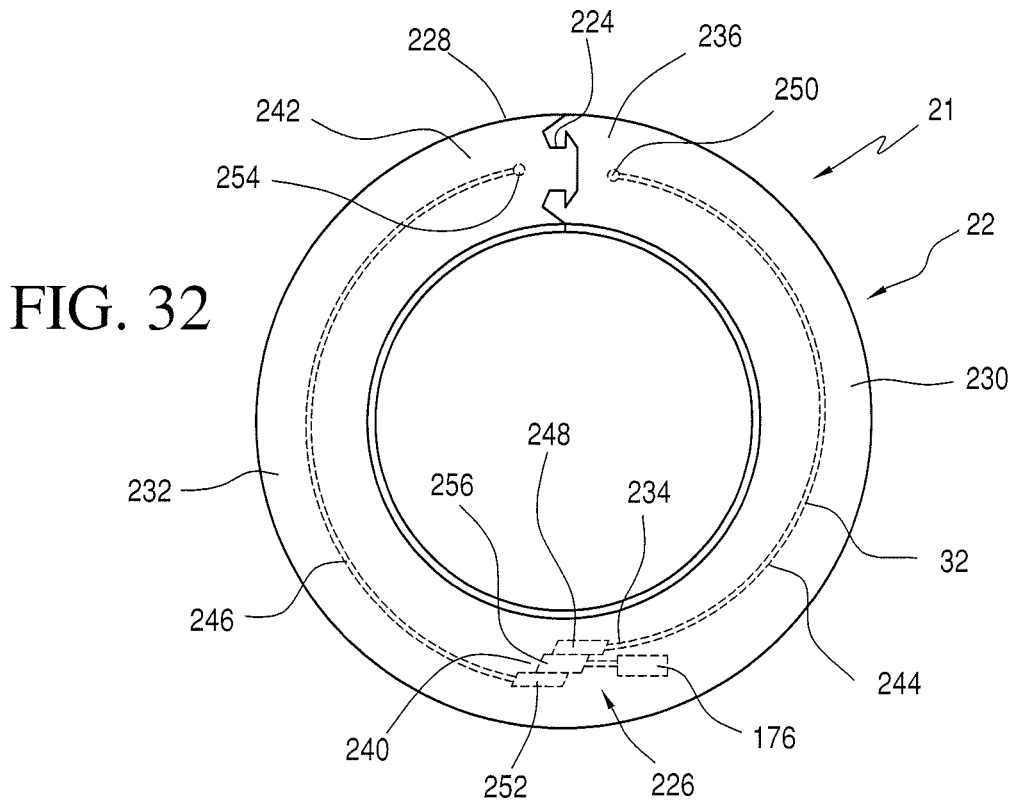
FIG. 32
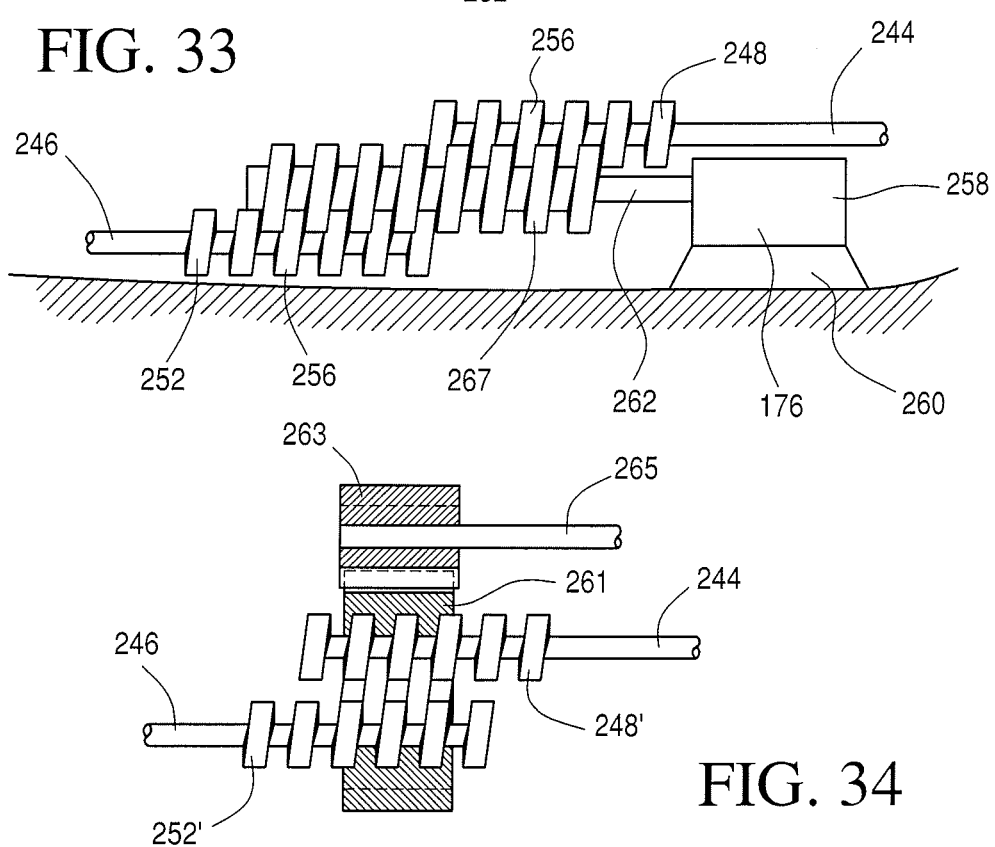
FIG. 33
FIG. 34

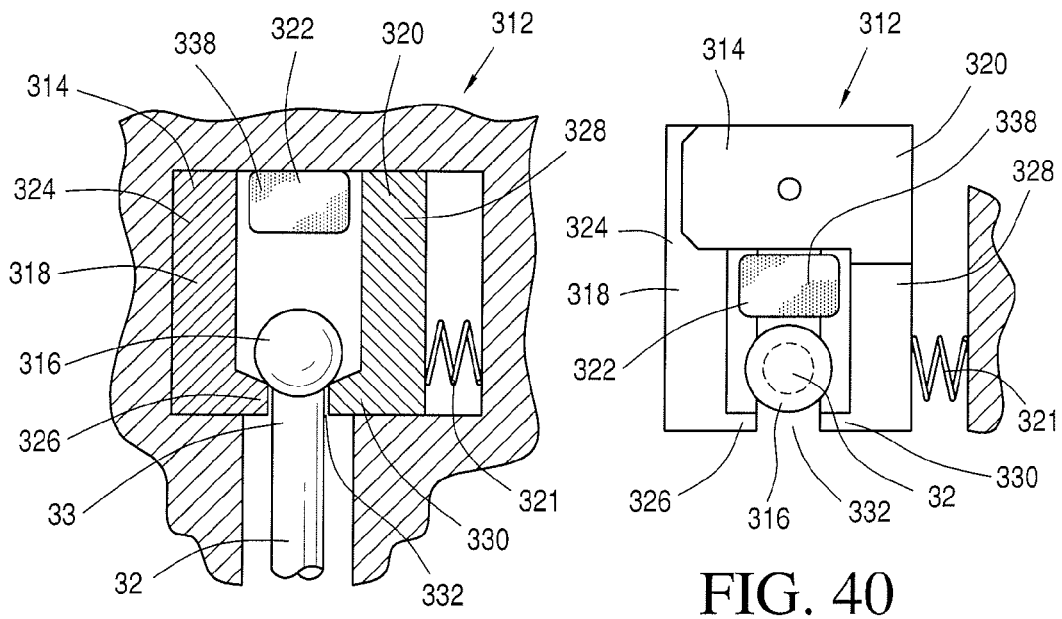
FIG. 39
FIG. 40
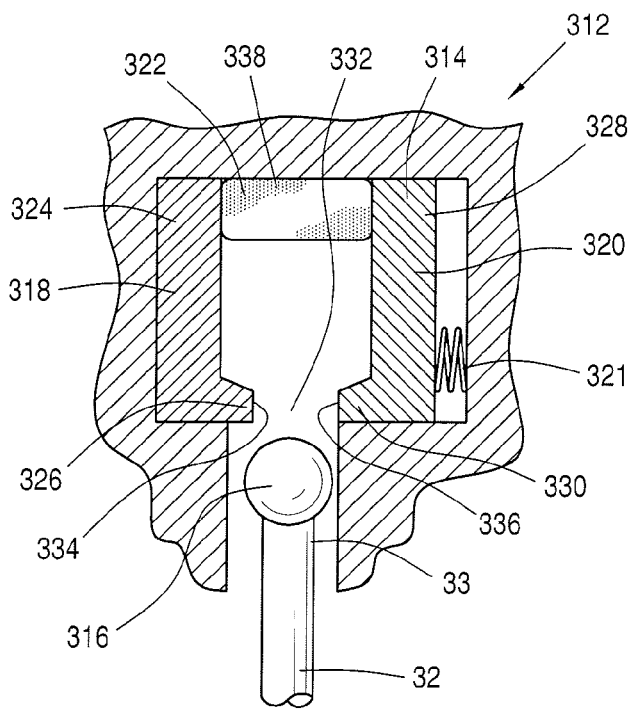
FIG. 41

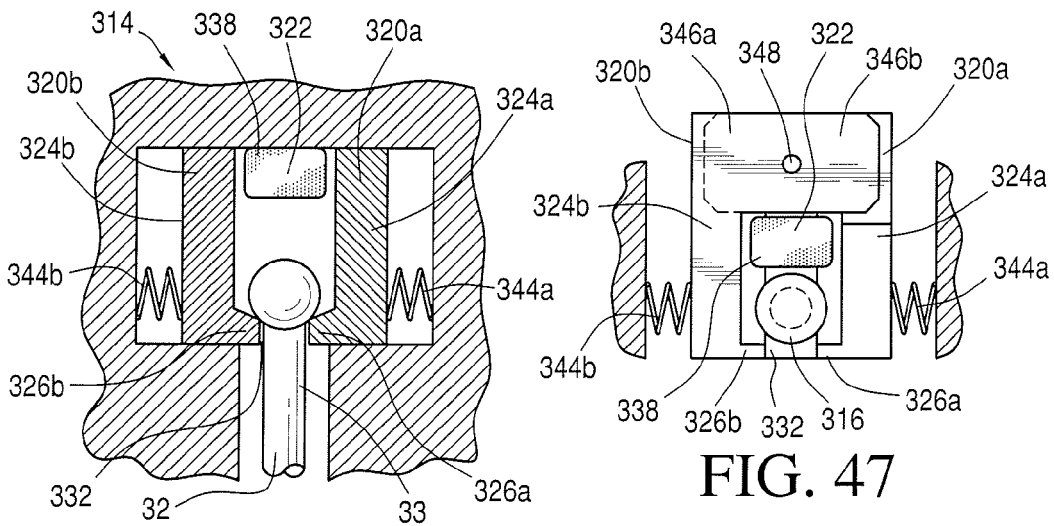
FIG. 46
FIG. 47
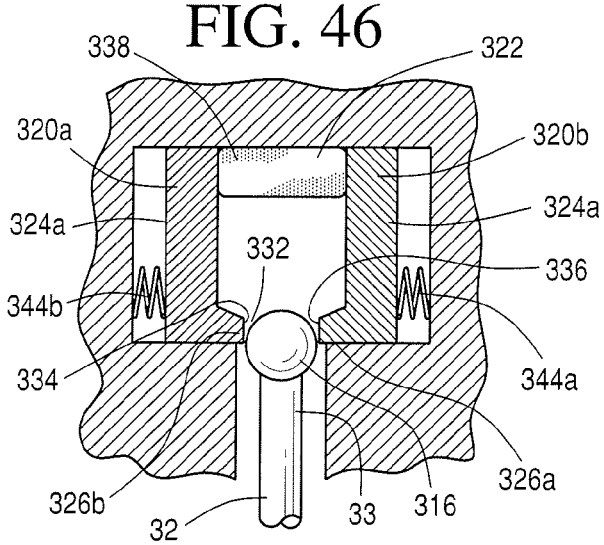
FIG. 48
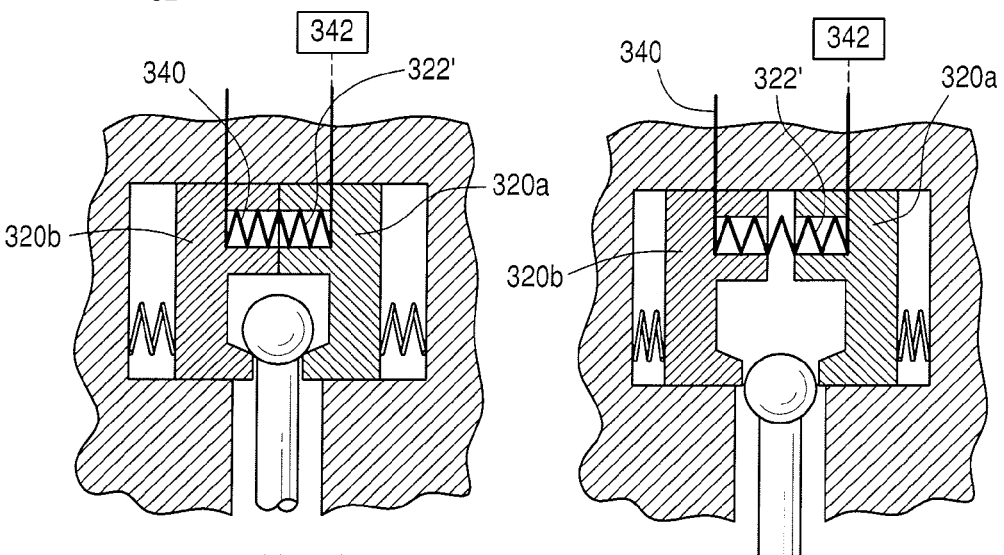
FIG. 49
FIG. 50

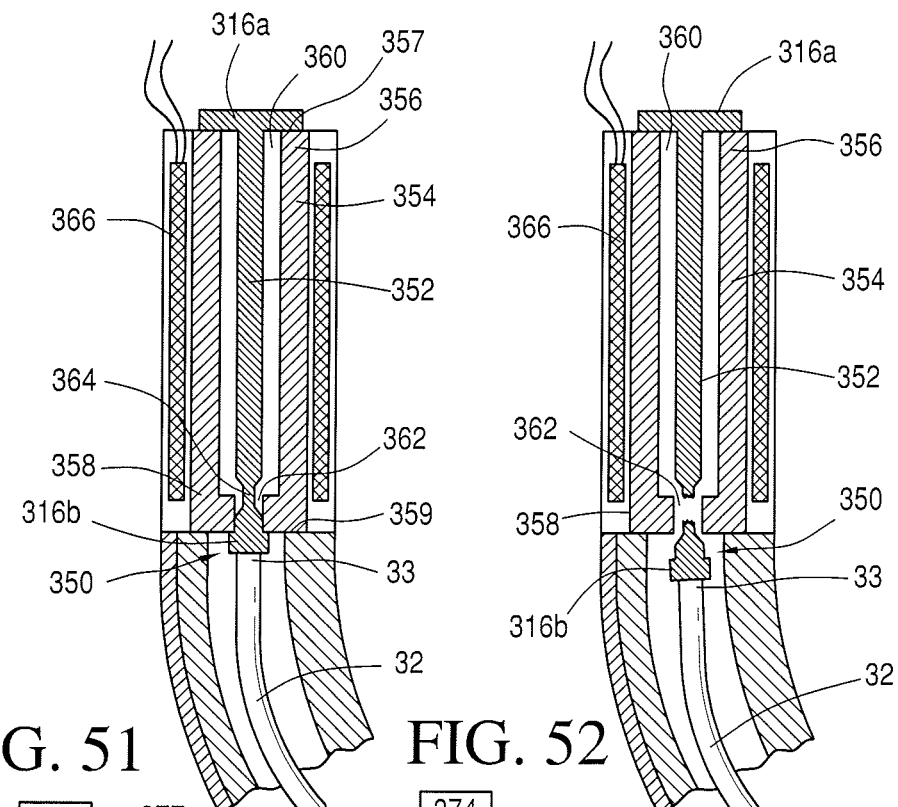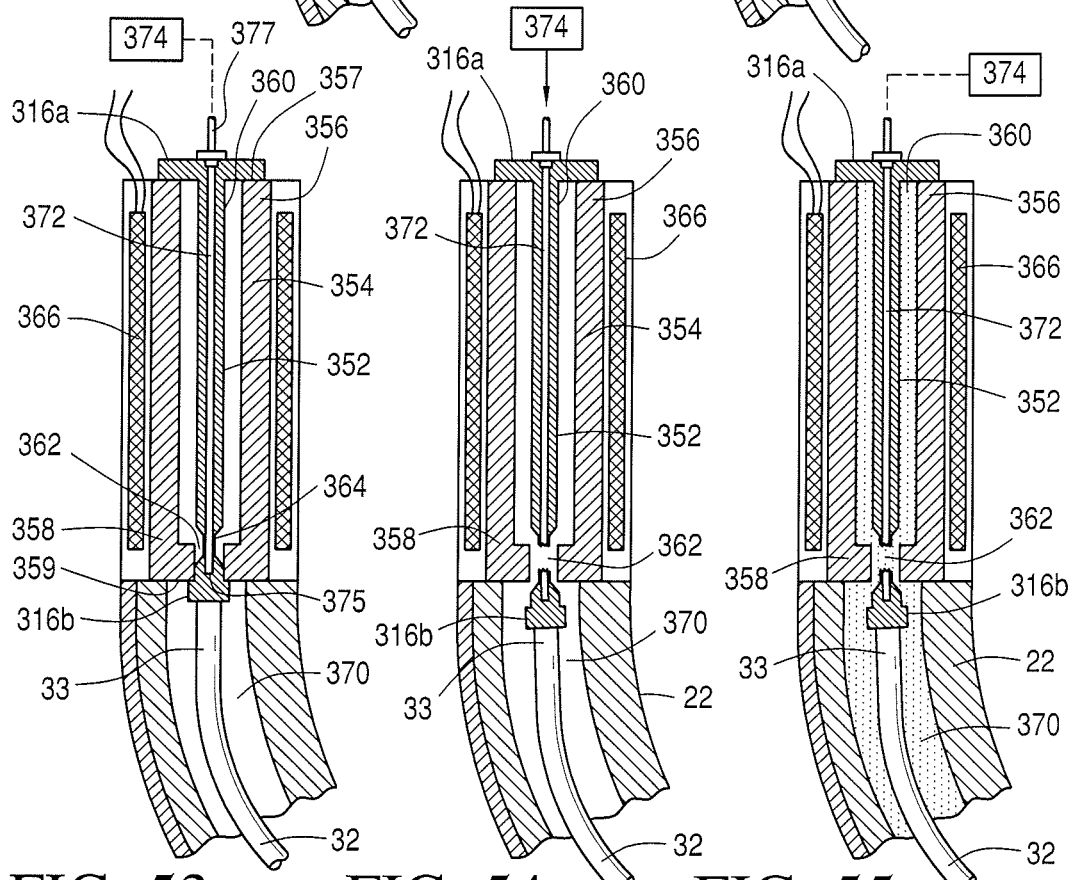
FIG. 51  FIG. 52  FIG. 53  FIG. 54  FIG. 55

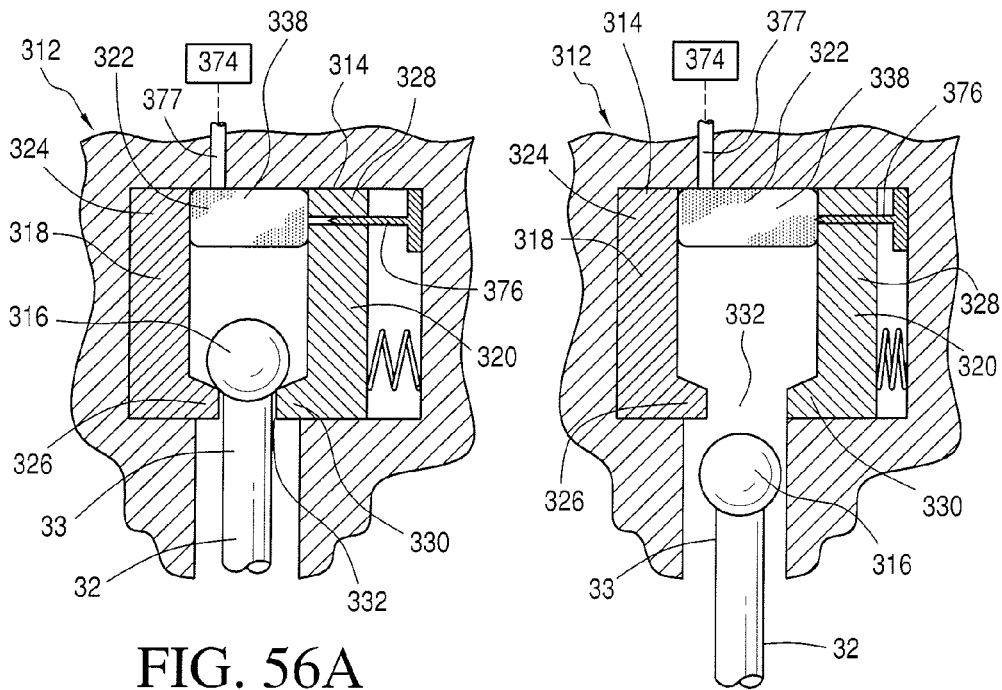
FIG. 56A
FIG. 56B
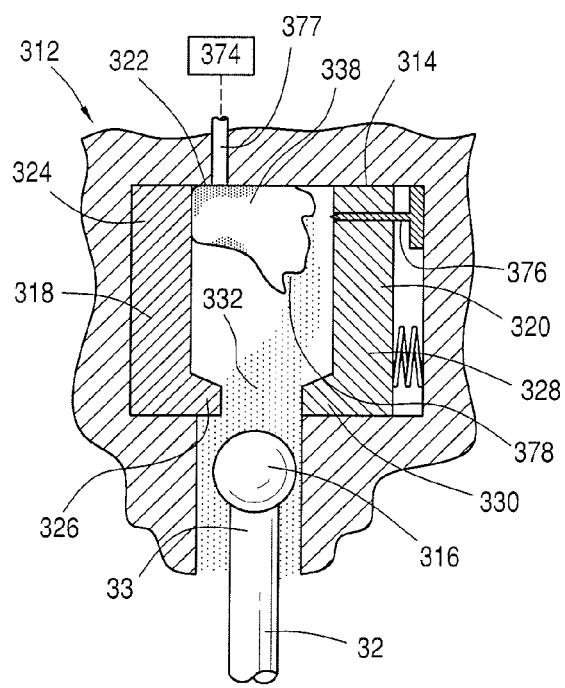
FIG. 56C

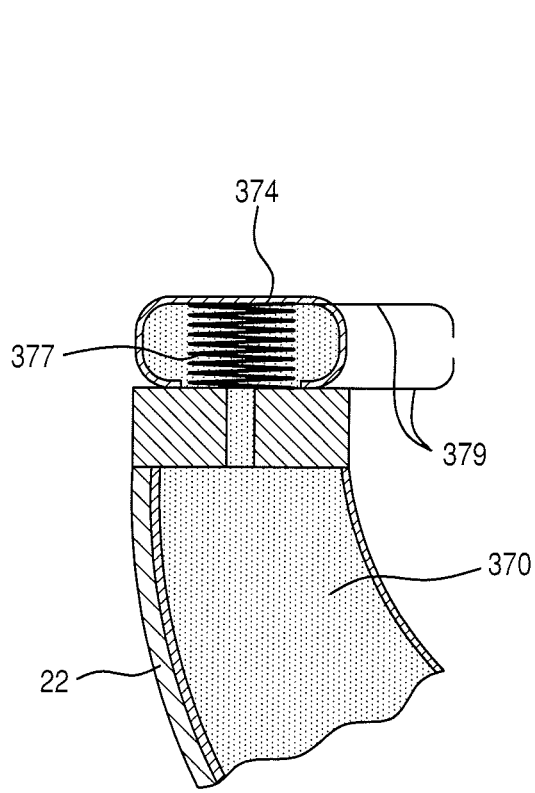
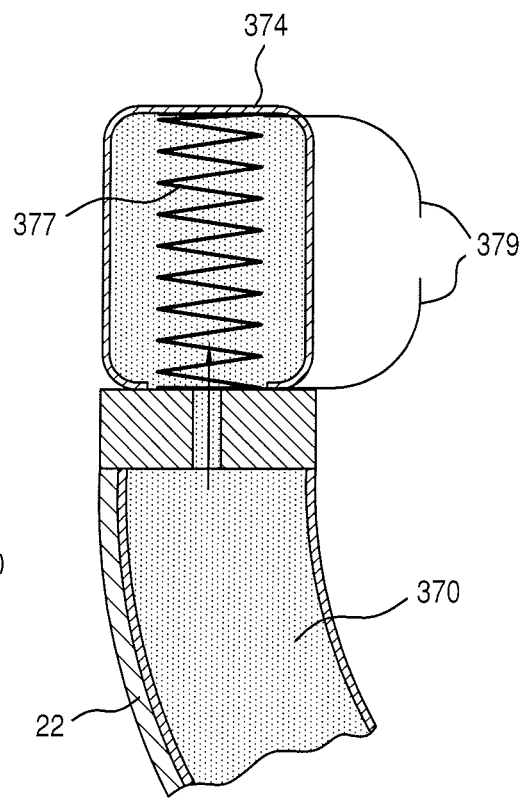
FIG. 57A  FIG. 57B
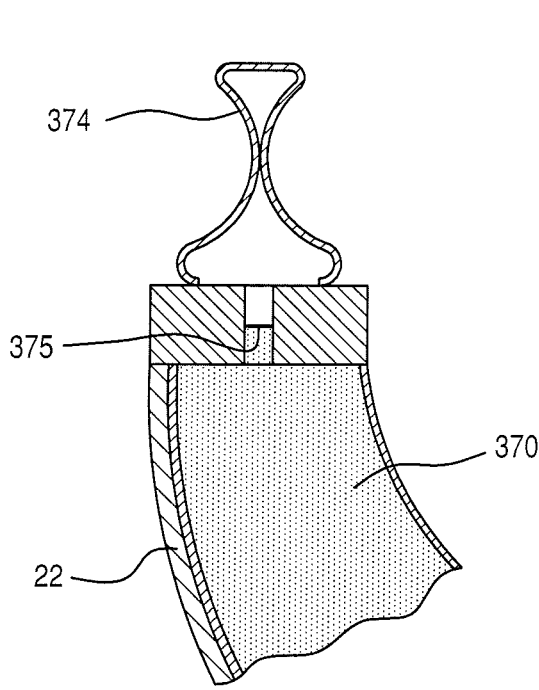
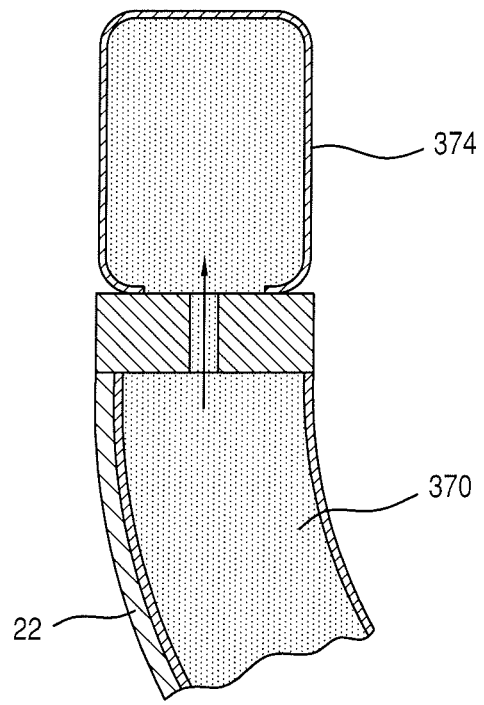
FIG. 58A  FIG. 58B

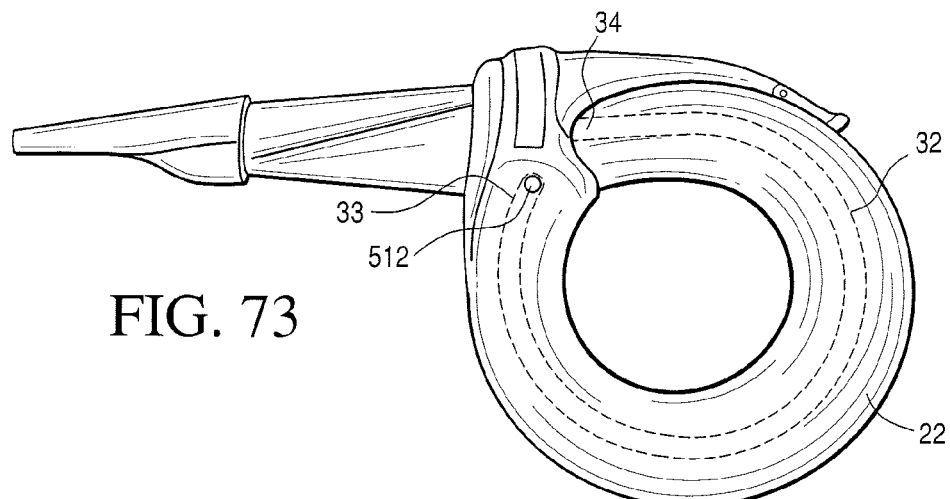
FIG. 73
FIG. 74
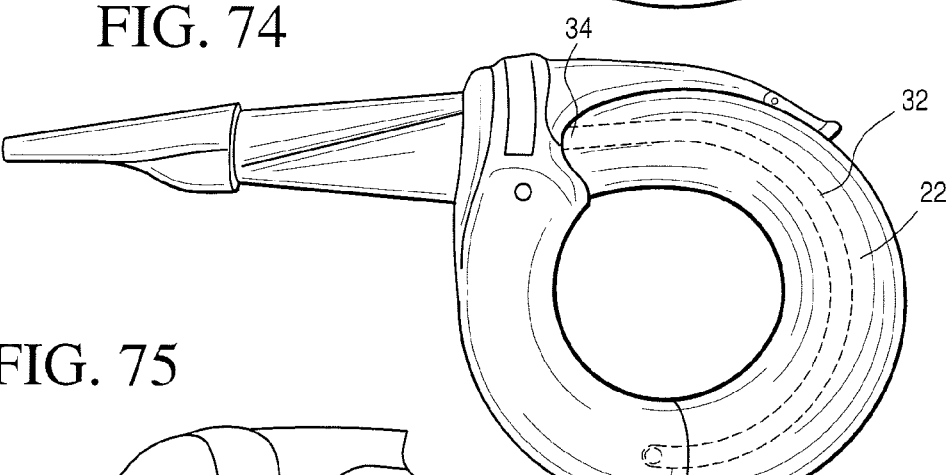
FIG. 75
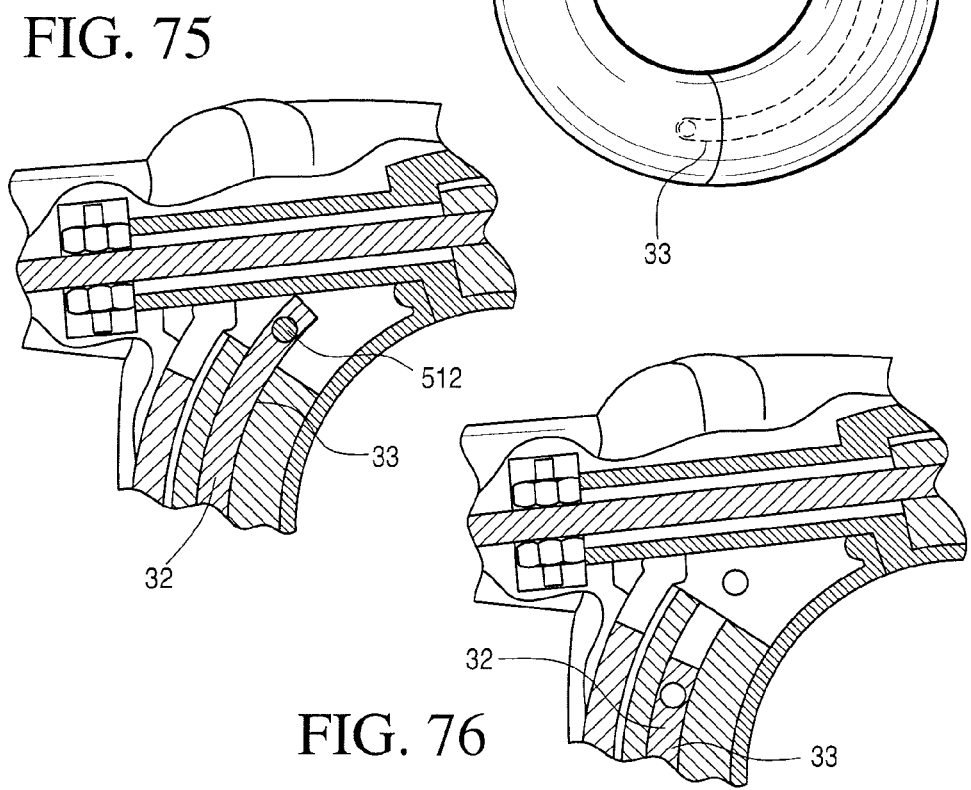
FIG. 76

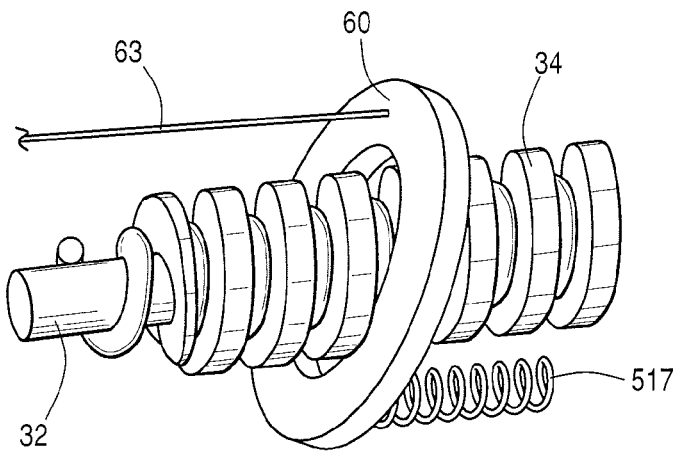
FIG. 80
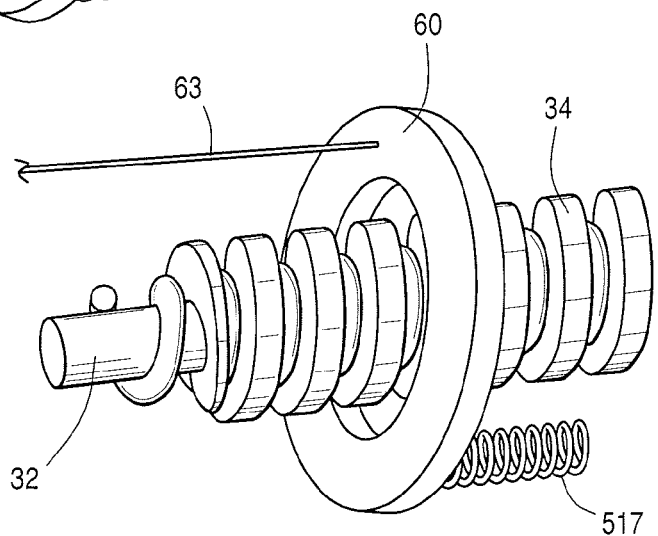
FIG. 81
FIG. 82
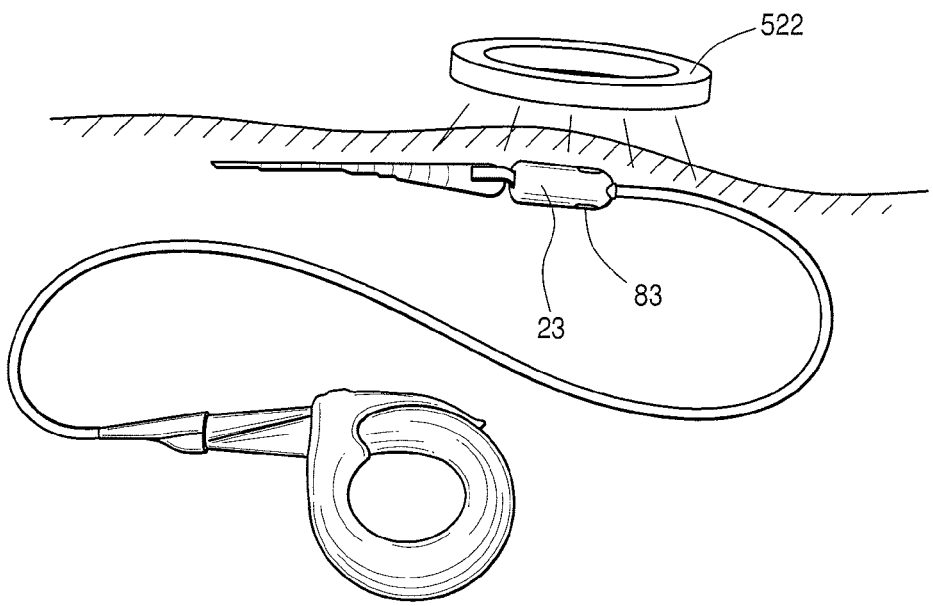

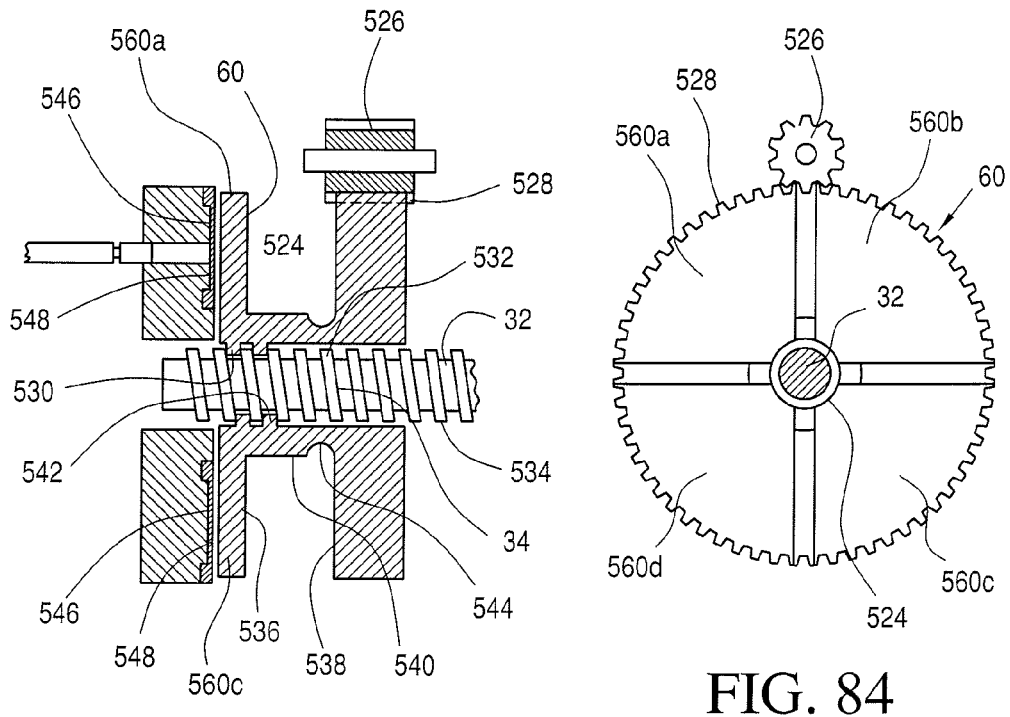
FIG. 83
FIG. 84
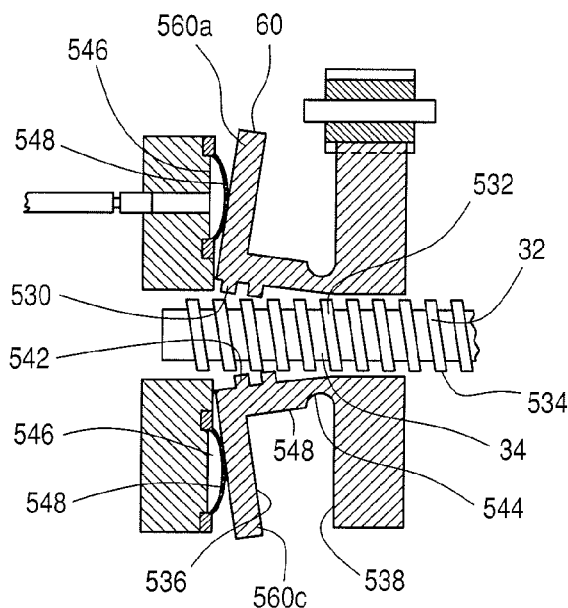
FIG. 85

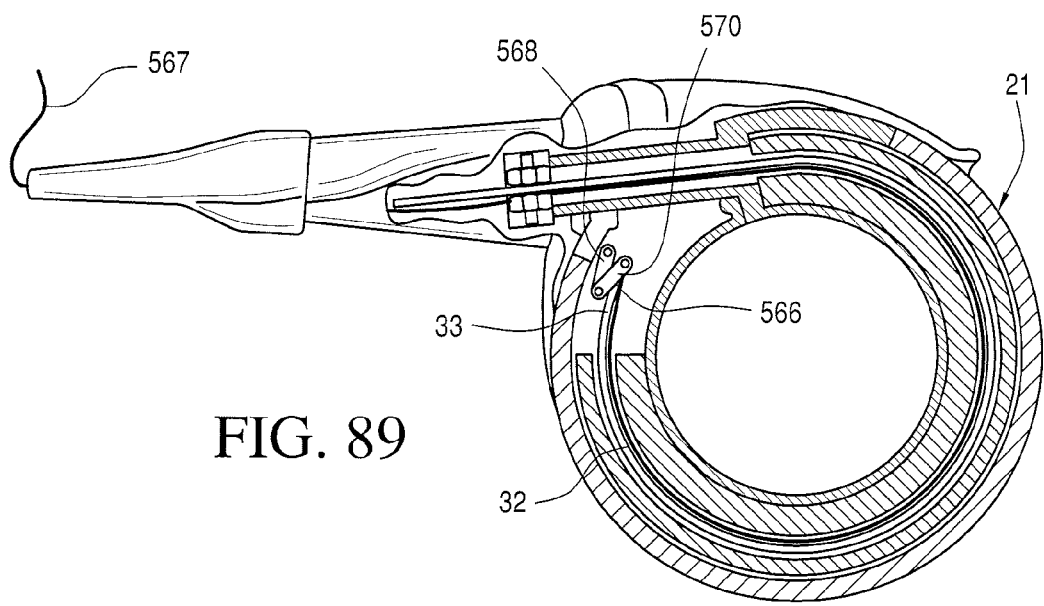
FIG. 89
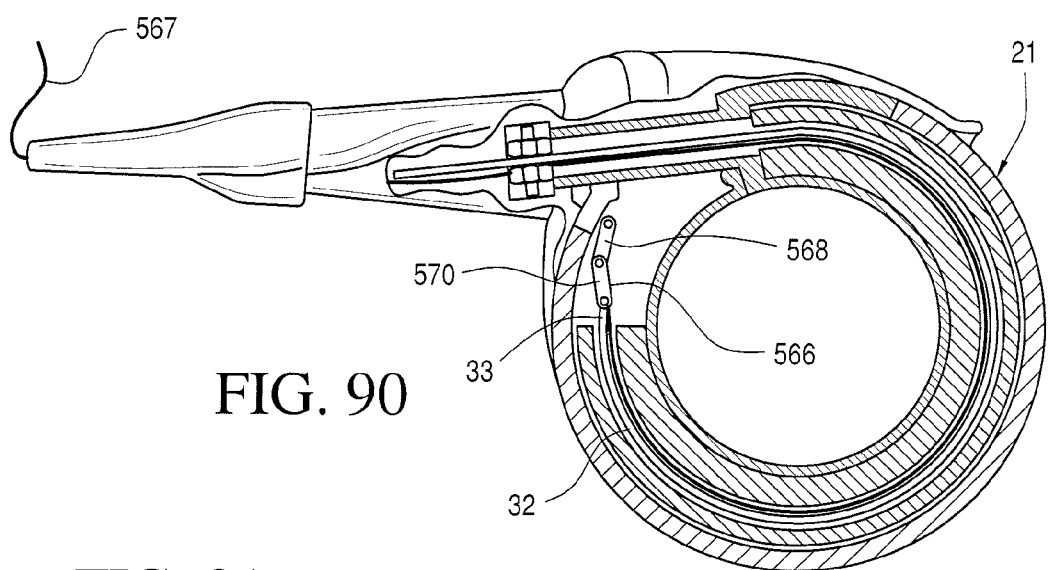
FIG. 90
FIG. 91
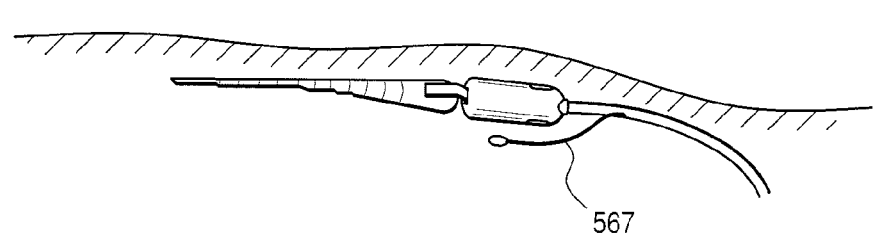

FIG. 100
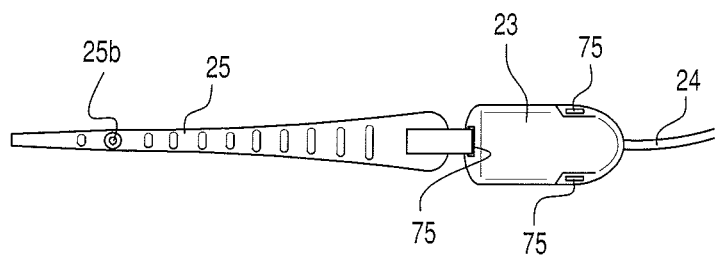
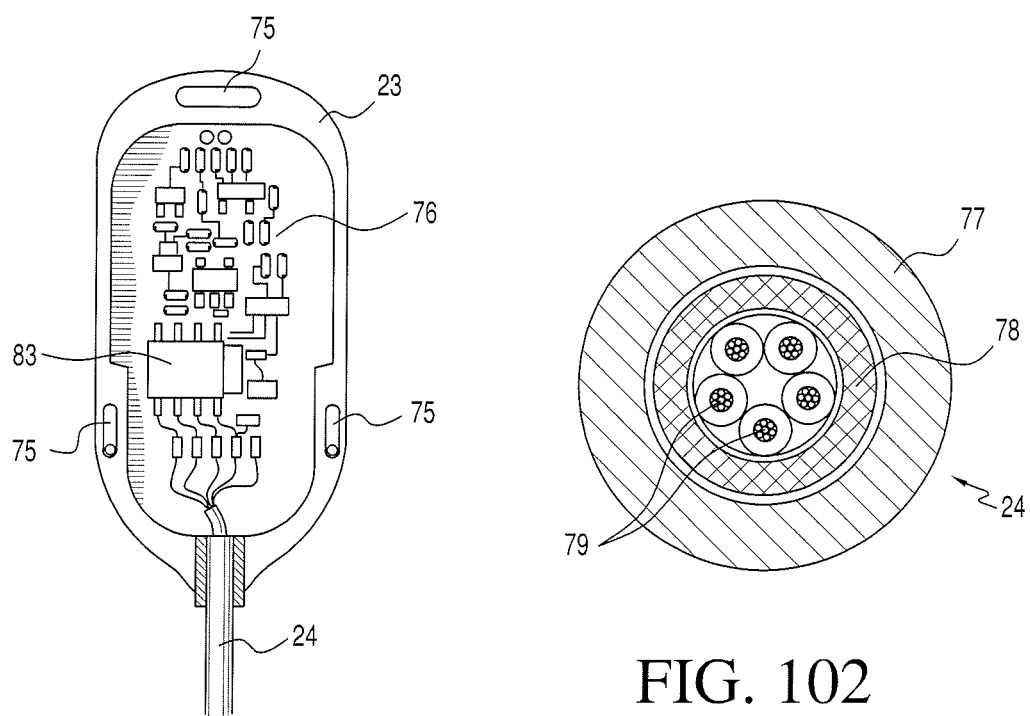
FIG. 102
FIG. 101

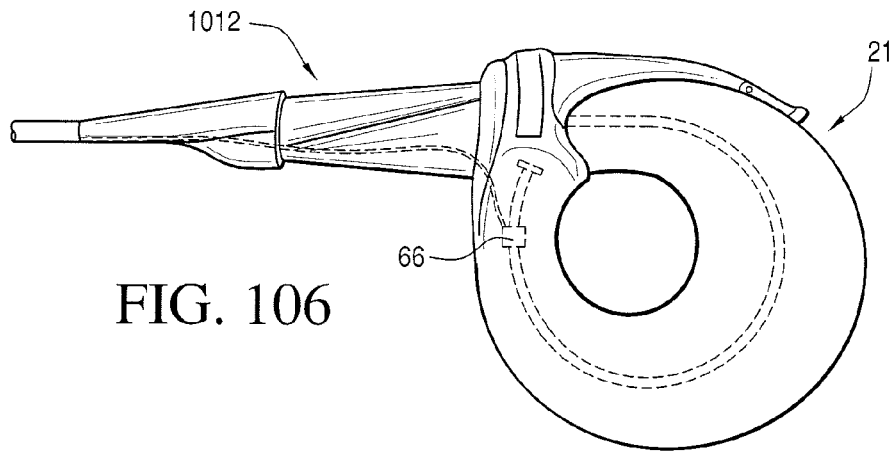
FIG. 106
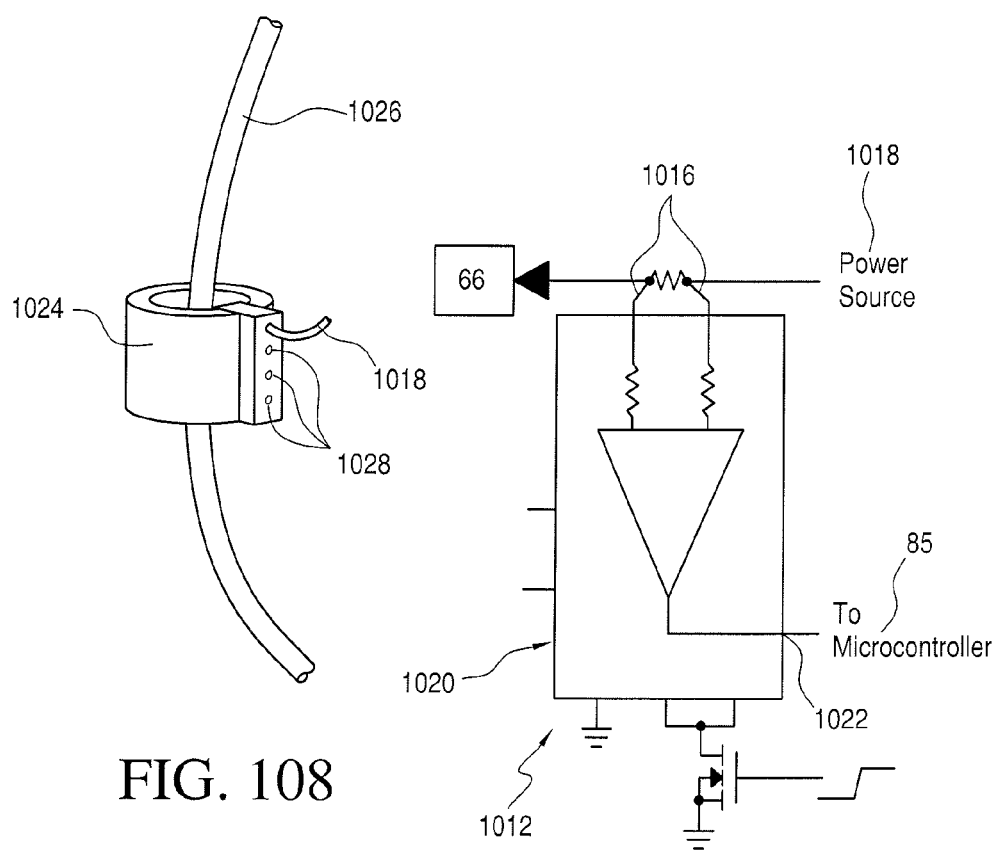
FIG. 108
FIG. 107

IMPLANTABLE RESTRICTION SYSTEM WITH LOAD MONITOR

BACKGROUND OF THE INVENTION

1. Field of the Invention

This invention relates to laparoscopic implanted restriction system designed to be implanted in the body of a patient around a biological organ having a pouch or duct to regulate functioning of the organ or duct. More specifically, the present invention is directed to an implantable telemetrically powered and controlled ring suitable for use as a gastric band to treat obesity or as an artificial sphincter.

2. Description of the Related Art

Obesity refers to a body weight that exceeds the body's skeletal and physical standards. One well recognized parameter used to measure obesity is Body Mass Index (BMI), because it takes into account patient height and not just weight. BMI is calculated by dividing weight by height squared and is expressed in kg/m2.

Obesity is well recognized as a serious health problem, and is associated with numerous health complications, ranging from non-fatal conditions to life-threatening chronic diseases. Surgical intervention generally is the treatment of choice for patients afflicted with morbid obesity. Such intervention not only mitigates the myriad of health problems arising from being overweight, but may also reduce the risk of early death of the patient. Left untreated, morbid obesity may reduce a patient's life expectancy by ten to fifteen years.

Morbidly obese patients as a group are poorly adapted to attain sustainable long-term weight loss using non-surgical approaches, such as strict diets combined with exercise and behavioral modification, even though such methods are acknowledged to be the safest. For this reason, there is a continuing need for direct intervention to provide effective, long-term treatments for morbid obesity. Three main surgical procedures are currently in use: Roux-en-Y Gastric Bypass ("RYGB"), Vertical Banded Gastroplasty ("VBG") and Adjustable Gastric Banding ("AGB").

In RYGB a small stomach pouch is created and a Y-shaped section of the small intestine is attached to the pouch so that food bypasses the lower stomach, the duodenum and the first portion of the jejunum. The RYGB procedure is both restrictive, in that the small pouch limits food intake and malabsorptive, in that the bypass reduces the amount of calories and nutrients the body absorbs.

VBG employs a non-adjustable synthetic band and staples to create a small stomach pouch. AGB employs a constricting synthetic ring defining a gastric band that is placed around the upper end of the stomach to create an artificial stoma within the stomach. The band is filled with saline solution and is connected to a small reservoir/access-port located under the skin of the abdomen. The AGB band may be inflated, thereby reducing the size of the stoma, or deflated, thus enlarging the stoma, by puncturing the access-port with a needle and adding or removing saline solution. Both VBG and AGB are purely restrictive procedures, and have no malabsorptive effect.

It is sometimes necessary to re-operate, either to relieve the patient or to adjust or change the previously implanted band. In such cases, the previously implanted band must be cut and either removed or replaced. These operations are difficult to carry out, difficult for the patient to tolerate and costly.

Several attempts to overcome the drawbacks associated with hydraulically actuated gastric bands, are found in the prior art. For example U.S. Pat. No. 6,547,801 to Dargent et al. describes a surgically implanted gastroplasty system having a flexible tactile element that engages a motor-driven notched pulling member. The motor is powered and controlled by an inductive circuit, so that the diameter of the ring may only be changed by operation of an external remote control.

All of the foregoing surgical techniques involve major surgery and may give rise to severe complications. Recent developments have focused on the use of laparoscopic implantation of the gastric ring to minimize patient discomfort and recuperation time.

In view of the foregoing, it would be desirable to provide apparatuses and methods for regulating functioning of a body organ or duct that provides high precision in controlling the degree of constriction imposed upon the organ or duct, without the drawbacks associated with prior control mechanisms.

SUMMARY OF THE INVENTION

It is, therefore, an object of the present invention to provide an apparatus for regulating the functioning of a patient's organ or duct including an elongated member having a first end and a second end. A fastener is disposed on the first end of the elongated member. The fastener is configured to engage the second end of the elongated member so that the elongated member forms a loop around the organ or duct. A tension element is disposed for movement within the elongated member. A drive element is associated with and engages the tension element for causing the tension element to control the tension applied by the elongated member against a patient's body organ or duct. A load monitor ensures that excessive pressure is not applied to a patient's body organ or duct.

It is also an object of the present invention to provide an apparatus wherein the load monitor includes a monitoring circuit monitoring current drawn by the drive element.

It is a further object of the present invention to provide an apparatus wherein drive element is motor.

It is another object of the present invention to provide and apparatus wherein the monitoring circuit is a closed loop feedback circuit.

It is also an object of the present invention to provide an apparatus wherein the monitoring circuit includes leads accessing current flowing from a power source to a motor of the drive element.

It is a further object of the present invention to provide an apparatus wherein the current is measured using a current sensing circuit and output current measurement is forward to a microcontroller for control of the drive element.

It is another object of the present invention to provide and apparatus wherein the monitoring circuit includes a Hall sensor positioned about a wire supplying a motor of the drive element with electrical power.

It is also an object of the present invention to provide an apparatus wherein load monitor is a strain gage.

It is a further object of the present invention to provide an apparatus wherein the drive element includes a motor acting upon threading of the tension element and the strain gage measures tension applied to the threading of the tension element.

It is another object of the present invention to provide and apparatus wherein the load monitor includes a pressure monitor associated with a fluid filled bladder forming part of the elongated member.

It is also an object of the present invention to provide an apparatus wherein the fluid filled bladder is formed along the interior surface of the elongated member.

It is a further object of the present invention to provide an apparatus wherein the fluid bladder is a separate component and may be added or fixedly attached to the elongated member prior to or during installation.

It is another object of the present invention to provide and apparatus wherein the fluid filled bladder is pre-filled with fluid and calibrated prior to implantation.

It is also an object of the present invention to provide an apparatus wherein the fluid filled bladder may be fluid calibrated post implantation.

It is a further object of the present invention to provide an apparatus wherein the fluid filled bladder is adjustable.

It is another object of the present invention to provide and apparatus wherein the fluid filled bladder is provided with a port in fluid communication with a filling tube that extends from the fluid bladder.

It is also an object of the present invention to provide an apparatus wherein fluid within the fluid bladder is a non-aqueous fluid or gel.

It is a further object of the present invention to provide an apparatus wherein load monitor includes a torque sensor measuring the motor torque.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 21 is a cross-sectional view of an elastomeric housing of the gastric band depicting the path of the antenna wire and cavity that accepts the tension element.

FIG. 22 is a perspective view of the drive element housing, tension element and drive element of the present invention.

FIG. 23 is a perspective view of the tension element engaged with the drive element.

FIGS. 27 to 38 show various embodiments of drive assemblies, which may be used in accordance with the present invention.

FIGS. 39 to 55 show various embodiments for releasing the fixed end of the tension element from its position at the second end of the ring.

FIGS. 56A-C show another embodiment of implementing a balloon based back-up system in conjunction with the mechanical tension element.

FIGS. 57A, 57B and 58A, 58B show a couple embodiments of releasing fluid from the secondary cavity of the ring.

FIGS. 73 to 76 show additional embodiments for releasing the tension element.

FIGS. 77 to 94 show various embodiments for releasing the free end of the tension element from engagement with the drive element in accordance with the present invention.

FIG. 100 is a perspective view of the antenna/controller pod of the present invention.

FIG. 101 is a cut-away view of the interior of the implantable antenna/controller pod of FIG. 100.

FIG. 102 is a cross-sectional view of the antenna cable of FIG. 100.

FIGS. 106 to 112 show various embodiments for monitoring the tension applied by the ring.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1:
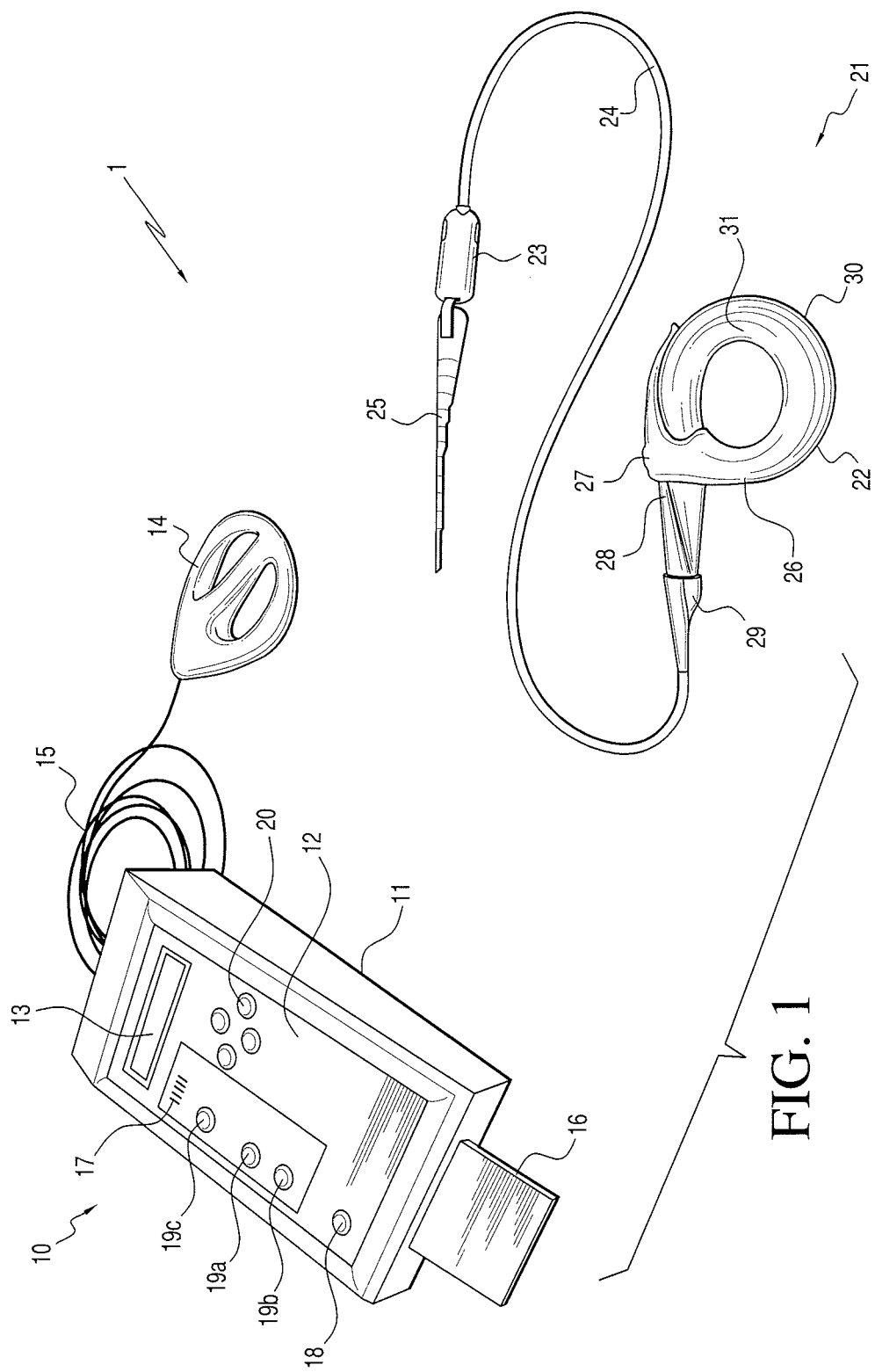
FIG. 1 is a perspective view of a banding system in accordance with the present invention.

Referring now to FIG. 1, the banding or implantable restriction system 1 of the present invention is described. The banding system 1 includes an external control 10 and implantable gastric band 21. In the following description reference will be made, by way of illustration, to a gastric band 21 in the form of a ring 22 designed to be implanted around the stomach to selectively adjust the diameter of the opening of the stoma, and thereby control food intake. Such regulation has the effect of creating a feeling of satiety in the patient after relatively little food is consumed, and provides an effective treatment for morbid obesity.

It is to be understood, however, that the present invention is in no way limited to gastroplasty, but on the contrary, advantageously may be applied to regulate the functioning of other body organs or ducts, such as in the treatment of gastroesophageal reflux disease, urinary or fecal incontinence, colostomy, ileostomy or to regulate blood flow in connection with isolated organ perfusion for treatment of cancer. When applied in the treatment of urinary continence, the implantable portion of the present banding system 1, in particular, the elongated member in the form of a ring 22 will be implanted around the bladder or urinary tract, while in the case of fecal incontinence, the ring 22 may be implanted around a portion of the gastro-intestinal tracts, such as anal structures of the intestine. With this in mind, the present banding system 1 is MRI compatible and all elements thereof are non-ferro-magnetic.

As discussed above, the present invention relates to an implantable restriction system. A preferred embodiment of the implantable restriction system is disclosed herein with reference to a gastric band used in restricting the effective size of the stomach for application in bariatric procedures. As such, the implantable restriction system of the present invention is referred to as including a gastric band or ring throughout the present disclosure, although those skilled in the art will appreciate the concepts underlying the present invention may be applied in a variety of implantable restriction devices as briefly discussed above.

System Overview

With respect to FIG. 1, the self-contained external control 10 comprises a housing 11 having a control panel 12 and a display screen 13. The external control 10 includes a digital signal processor and may be battery-powered or powered using an external power supply, e.g., connected to an electric wall outlet. An external antenna 14 is coupled to the external control 10 via a cable 15. As described more fully with respect to FIG. 105, the external control 10 includes a controller (such as a microprocessor) that controls the emission of radiofrequency signals to the gastric band 21 to both control and power operation of the gastric band 21.

The external control 10 accepts a patient microchip card 16, which corresponds to the specific gastric band 21 implanted in the patient, and stores data, such as the implant identification number, adjustment parameters (e.g., upper and lower limits of an adjustment range, etc.) and information regarding the last adjustment position of the ring 22. The external control 10 as shown in FIG. 1 includes a signal strength indicator 17, as described in more detail below with respect to FIG. 103, an ON/OFF button 18, an OPEN button 19a, a CLOSE button 19b, a COUPLING button 19c and a menu options panel 20.

During use of the present banding system 1, the physician need only turn on external control 10 using the ON/OFF button 18, position the external antenna 14 over the patient's chest above antenna/controller pod 23, check the coupling by depressing the COUPLING button 19c, and when the coupling is sufficient, adjust the degree of constriction using the OPEN button 19a or the CLOSE button 19b to control the effective circumference of the ring 22 in a manner discussed below in greater detail. The diameter of the gastric band 21 is continually displayed on the display screen 13 with a precision of about 0.1 mm for the entire range of diameters of the ring 22, e.g., from 19 mm fully closed to 29 mm fully opened.

Still referring to FIG. 1 and as briefly mentioned above, the gastric band 21 of the present invention includes a ring 22 coupled to an implantable antenna/controller pod 23 via an antenna cable 24. The antenna/controller pod 23 includes a removable tag 25 that may be used to laparoscopically position the ring 22. The ring 22 includes a first end 26 having a clip 27 that slides over and positively engages a second end 28 of the ring 22.

Figure 20:
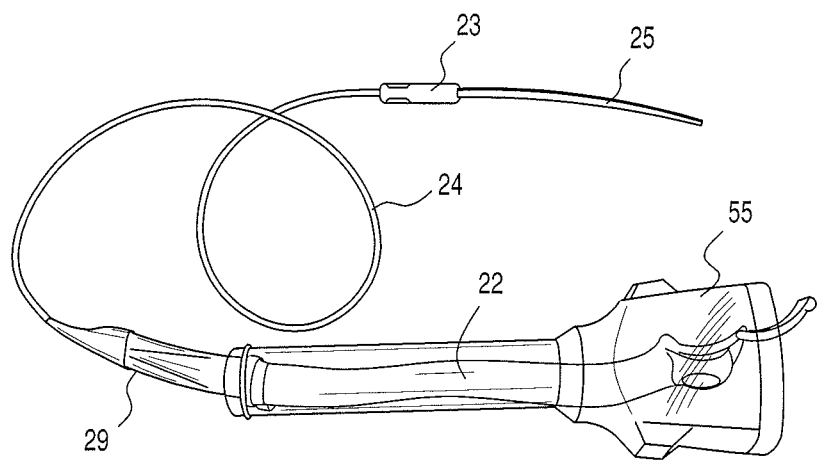
FIG. 20 is a perspective view of the ring of FIG. 1 straightened and inserted within a standard 18 mm trocar.

As described in detail below, the ring 22 is configured to be straightened to pass through the lumen of a commercially available 18 mm trocar for delivery to a patient's abdomen (see FIG. 20). The tag 25, antenna/controller pod 23 and antenna cable 24 are passed through a clip 27 to form the gastric band 21 into a substantially circular ring 22 around an upper portion of the patient's stomach, thereby reducing the diameter of the opening of the stomach. In its undeformed shape, the ring 22 assumes a circular arc configuration that facilitates positioning of the ring 22 around the stomach and also in self-guiding the clipping procedure.

The ring 22 of the present invention comprises a flexible tubular member having a smooth, flexible and elastic membrane, thus ensuring atraumatic contact with the patient's stomach tissue that is easily tolerated. When engaged with a dorsal element 38, the membrane 39 is stretched by an appropriate factor (i.e., 20%-40%), so that when the ring 22 is in it's fully closed position, little or no wrinkling appears on the membrane surface. The ring 22 has approximately the shape of a torus of revolution of substantially cylindrical cross-section. Alternatively, the ring 22 may have other suitable cross-sections, including rectangular. The housing 29 on the second end 28 of the ring 22, the clip 27 on the first end 26 of the ring 22 and the dorsal peripheral portion 30 of the ring 22, preferably are made of a biocompatible material such as silicone. An interior portion 31 of the ring 22 may be constructed in a variety of manners as discussed below in greater detail to permit engagement with the tissue without bunching or rippling, and, as discussed below in greater detail, may be covered in various manners to enhance the ring/tissue interface and protect the ring 22.

Implantable Ring

Figure 2A:
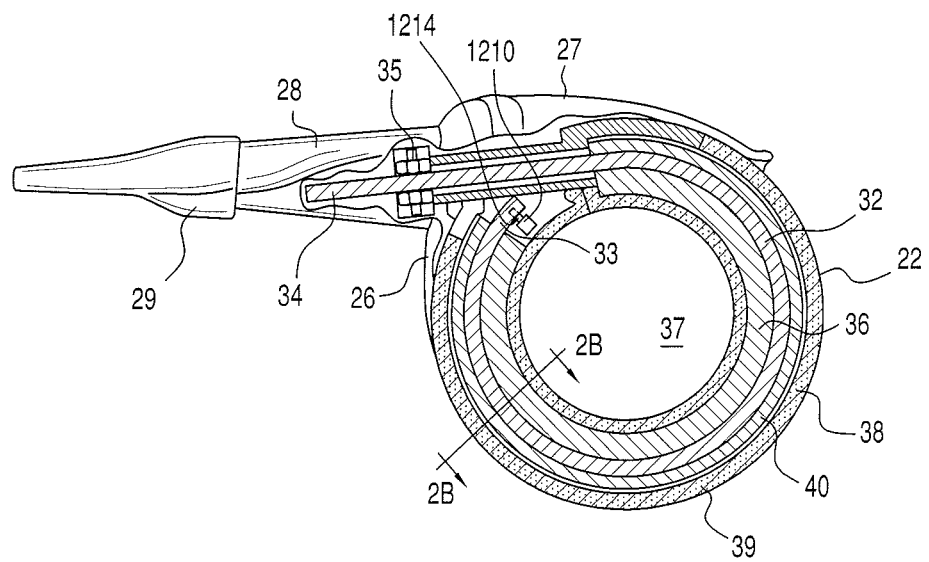
FIGS. 2A and 2B are, respectively, a schematic diagram, partly in cross-section, of the gastric band of FIG. 1 and a sectional view taken along line 2B-2B of FIG. 2A.
Figure 2B:
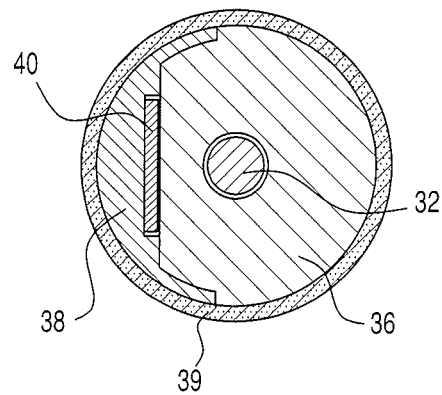
Figure 3:
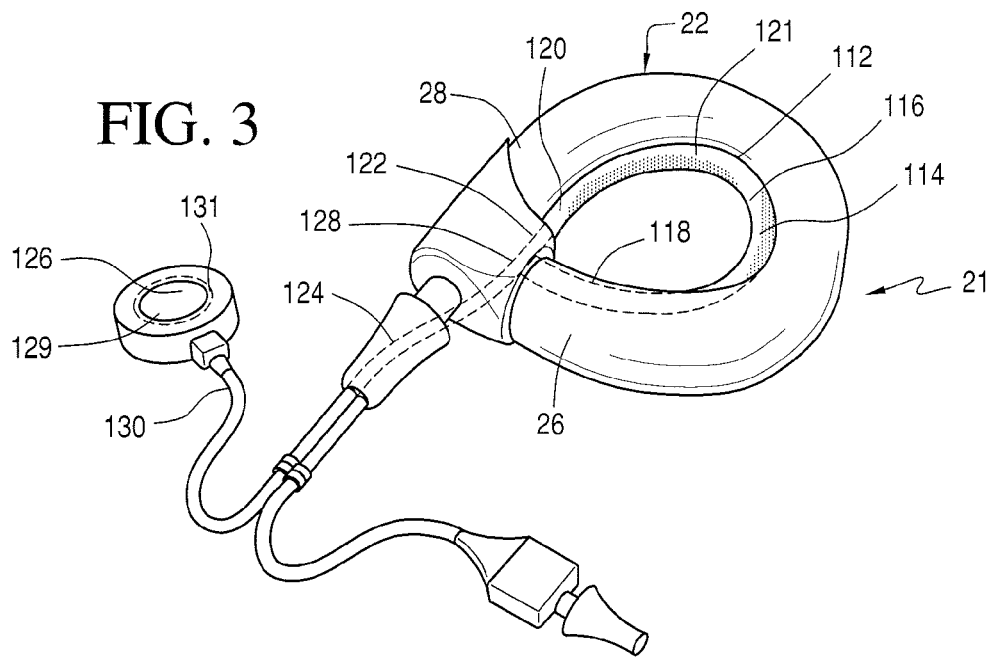
FIGS. 3 to 14 show various embodiments enhancing the interior surface of the ring for contact with tissue.
Figures 4, 5, 6:
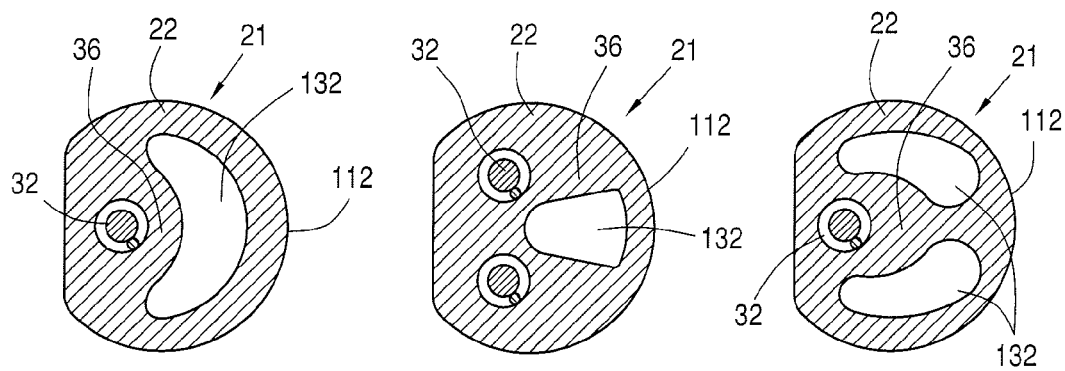
Figures 7, 8:
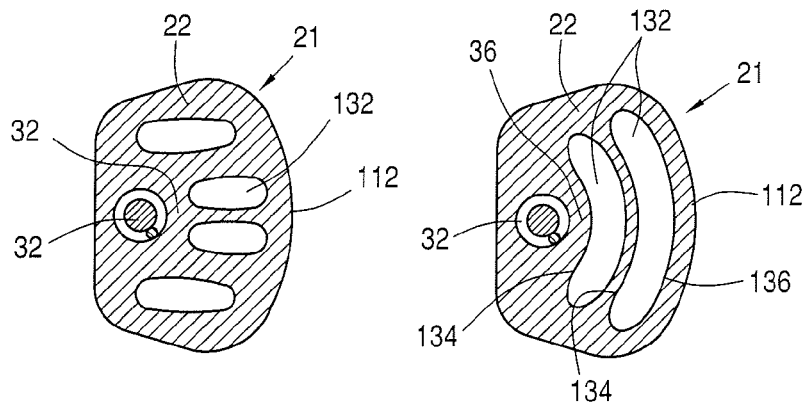

Referring now to FIGS. 2A and 2B, the internal structure of the ring 22 is described. In particular, and as depicted in FIG. 2A, the ring 22 includes a flexible tension element 32 having a fixed end 33 statically mounted to the first end 26 of the ring 22 and a free end 34 that is engaged with a motor-driven drive element 35 and extends into a cavity in the housing 29. The tension element 32 is slidingly disposed within a substantially cylindrical tube of a compressible material 36, e.g., ePTFE, as illustrated in FIG. 2B, so that when the tension element 32 is pulled through the drive element 35, the compressible material 36 is compressed and the diameter of opening 37 is reduced. The compressible material 36 is preferably surrounded on its dorsal face by a dorsal element 38. The dorsal element 38 is flexible, but sturdier than the elastomeric material of the compressible material. The dorsal element is preferably composed of silicone. Both the compressible material 36 and the silicone dorsal element 38 preferably are enclosed within a membrane 39 of elastomeric biocompatible material, as shown in FIG. 2B, to prevent tissue in-growth between the ePTFE compressible material 36 and the silicone dorsal element 38. The membrane 39 may be affixed to the dorsal element 38 using a biocompatible glue to prevent leakage in case of accidental puncture on the dorsal surface.

With reference to FIGS. 3 to 14, various embodiments have been developed for improving the interaction between the inner surface 112 of the ring 22 and the tissue it engages as the band 21 is constricted about the stomach of a patient. In accordance with a first embodiment as shown with reference to FIG. 3, a fluid bladder 114 is added to the inner surface 112 along the internal circumference of the ring 22 such that the fluid bladder 114 interfaces with the tissue. In addition, to improving the tissue band interface, the addition of a fluid bladder 114 along the inner surface 112 of the ring 22 allows for ready adjustments to the restrictive level of the ring 22.

In accordance with such an embodiment, and as briefly discussed above, the fluid bladder 114 is formed along the inner surface 112 of the ring 22 for direct engagement with the tissue when the ring 22 is applied to the stomach and constricted thereabout. The fluid bladder 114 is preferably made of silicone (or other biocompatible material) and is constructed as an elongated cylindrical member 116 with a high degree of flexibility allowing it to conform to the surface of the tissue to which it is applied without adversely affecting the tissue when applied thereto for long periods of time. The cylindrical member 116 extends about substantially the entire length of the inner circumference of the ring 22. As such, the fluid bladder 114 includes a first end 118 adjacent the first end 26 of the ring 22 and a second end 120 adjacent the second end 28 of the ring 22.

The cylindrical member 116 includes a central lumen 121 shaped and dimensioned to receive a filling fluid as discussed below. The cylindrical member 116, and ultimately the central lumen 121, includes the closed first end 118 and the open second end 120. The second end 120 is provided with a port 122 in fluid communication with a filling tube 124 that extends from the fluid bladder 114 to a remote fluid source 126 allowing for the controlled application of the fluid to the fluid bladder 114 for filling thereof as desired by the medical practitioner deploying and installing the present ring 22. In accordance with such an embodiment, it is contemplated the remote source of fluid 126 could be integrated with the antenna/controller pod 23 as discussed below in greater detail.

The filling tube 124 is provided with a first end 128 which is secured to the port 122 of the fluid bladder 114 and a second end 130 positioned remote from the first end 128. The second end 130 is fixedly or selectively secured to a source of fluid 126 for filling the fluid bladder 114 as one may desire in accordance with the principles of the present invention. In accordance with a preferred embodiment, the fluid source 126 is a miniature fill port which is subcutaneously implanted (for example, in conjunction with the antenna/controller pod 23) for access and addition of fluid as required by the needs of the patient being treated. The fill port 126 includes a flexible access septum 129 through which the medical practitioner may access the internal cavity 131 of the fill port 126 for increasing or decreasing the volume of fluid applied to the fluid bladder 114 positioned along the inner surface 112 of the ring 22 and in direct contact with the tissue of the stomach.

It is further contemplated that to achieve a softer tissue interface without secondary adjustability, the fluid bladder may be prefilled prior to implantation. Where such an implementation is employed, a fluid port would not be required. The fluid could be added directly through a catheter attached to the fluid bladder. Once added, the fluid would be trapped by plugging the catheter (for example, tying in a knot, adding a fluid plug, luer activated valve, etc.).

In the event of a mechanical or electrical adjustment feature failure the fluid bladder would allow at least minor adjustments to the band. The fluid bladder can be used as a safety feature in case the mechanical adjustment is not functioning properly, since fluid could easily be removed from the bladder un-tightening the gastric band and relieving the pressure applied to the stomach.

It is contemplated the fluid bladder could be prefilled with a substance or solution prior to installation. Where the fluid bladder is prefilled, the fluid within the fluid bladder is hyper-osmolar relative to the implanted physiological environment. For example, the filling fluid may be a salt solution or ionic polymer solution, sodium alginate, sodium hyaluronate, etc. The fluid may also be hypo-osmolar relative to the implanted physiological environment, such as, a non-ionic polymer solution poly(ethylene glycol). The fluid may also be a non-Newtonian fluid, such as, a polymer solution selected from the group consisting of a poly(vinylpyrrolidone), carboxymethylcellulose, poly(ethylene glycol), poly(acrylamid), sodium hyaluronate, hyaluronic acid, and alginates. The fluid may further be a non-aqueous fluid or gel, such as, a silicone oil or fluorosilicone oil.

In accordance with an alternate embodiment, the ring 22 is shaped and dimensioned to provide for more compliant material and/or construction by altering the cross sectional geometry of the ring 22 to reduce the spring constant of the compressible material 36 between the tension element 32 and the tissue. In addition, improved compliance and construction are achieved by altering the construction of the gastric band 21 such that a secondary, softer material is introduced into the space between the tension element 32 and the tissue, giving the gastric band 21 a reduced spring constant. Improved compliance and construction is further achieved by combining a reduced spring constant with a viscoelastic filler material to give viscoelastic (or rate dependent) deformation characteristics.

In accordance with this embodiment, and as show with reference to embodiments shown in FIGS. 4 to 8, variations in the spring constant of the gastric band 21 between the tension element 32 and the tissue is achieved through the formation of longitudinally extending space(s) 132 within the compressible material 36. In accordance with a preferred embodiment, the space(s) 132 maintains a constant shape along the length of the compressible material 36, although it is contemplated the shapes of the space(s) 132 may be varied along the length of the compressible material 36 and the ring 22. In practice of the present embodiment, the spring constants may be derived or inferred from tissue interface pressures in the range of −100 mmHg to 300 mmHg gauge pressure wherein the basic relationship is determined by the formula $p=F/A$. However, it is also contemplated pressures outside this range may also be used.

The space(s) 132 may be filled with another material such as silicone rubber, a lower durometer polymer or closed-cell foam to give a reduced spring constant. The space(s) 132 within the cross section may also include viscous or viscoelastic filler materials. That is, they demonstrate rate dependent response to dynamic force conditions such as the passage of food through the esophagus. Potential viscous/viscoelastic filler materials include, but are not limited to, saline liquid or gel silicone, biogels, close cell foams, or pack granules or spears of one or more materials.

In addition to improving the spring constant, the incorporation of open space(s) 132 in the compressible material 36 as disclosed herein maximizes the interface between the ring 22 and the tissue thereby spreading the forces or interface pressures applied to the tissue in accordance with the present invention.

As discussed above, the space(s) 132 may take a variety of forms. For example, and with reference to FIG. 4, the space 132 takes the form of a substantially C-shaped lumen. In accordance with an alternate embodiment as shown with reference to FIG. 5, the space 132 takes the form of truncated triangle wherein the top section (that is, the narrow portion adjacent the tension element 32) of the triangle is curved and the bottom section (that is, the wide portion removed from the tension element 32) of the triangle includes a slightly concave base. In accordance with yet a further embodiment, and with reference to FIG. 6, first and second arcuate spaces 132 are provided on opposite sides of the ring 22. Once again, and with reference to FIG. 7, four elongated spaces 132 are provided. The elongated spaces 132 are oriented such that when viewed across the cross section of the ring 22, the longitudinal axis thereof extends transversely against the longitudinal axis passing through the center of the ring 22. In accordance with yet a further embodiment, and with reference to FIG. 8, the spaces 132 are formed so as to extend circumferentially about the compressible material 36 of the ring 22 and take the form of arcuate members whose concave surfaces 134 faces away from the center of the ring 22 and whose convex surfaces 136 face away from the center of the ring 22.

Figures 9, 10:
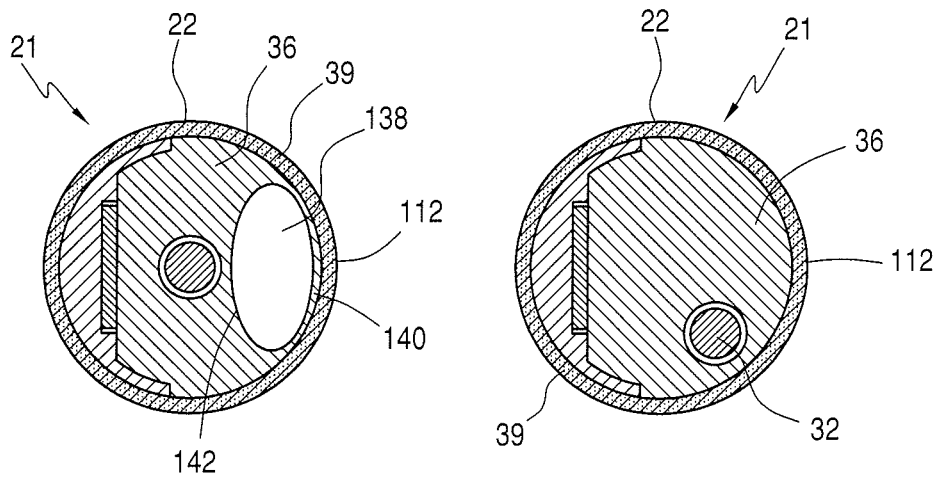

In accordance with yet another embodiment of the present invention, and with reference to FIG. 9, the ring 22, and in particular, the compressible material 36, may be provided with a fluid chamber 138 extending along the inner circumferential portion of the compressible material 36. In contrast to the embodiment disclosed above with reference to FIG. 3, the fluid lumen or chamber 138 forms part of the compressible material and is preferably integrally formed with the compressible material 36. As such, the compressible material 36 may be thought of as including a fluid lumen 138 along its inner surface, the fluid lumen 138 being shaped and dimensioned for maintaining a desired fluid therein so as to improve the stress profile being applied to the tissue.

In accordance with a preferred embodiment of the present invention, the fluid chamber 138 includes a cross-sectional profile, when viewed along a plane transverse to the circumferential axis running along the center of the ring 22, that remains constant along the length of the ring 22. The profile is elliptical defining an arcuate inner wall 140 and an arcuate outer wall 142 with the concave surfaces thereof facing each other.

In addition to improving the tissue to ring interface by providing greater compliance along this area, the fluid chamber 138 may also allow for expansion of the gastric band 21 in the event the mechanical adjustment system fails. In particular, the fluid lumen 138 is maintained in fluid communication with a remote fluid pressure source as discussed above with reference to FIG. 3. As such, and if the mechanical or electrical adjustment feature fails, fluid may be pumped into the fluid lumen 138 creating additional pressure that is transferred to the stomach about which the ring 22 is positioned. Alternatively, fluid may be removed from the fluid lumen 138 thereby relieving pressure applied to the stomach about which the ring 22 is positioned. In accordance with a preferred embodiment, it is contemplated the fluid source may be housed in and controlled by the antenna/controller pod 23 of the ring 22. It is further contemplated, the fluid source may also be manually adjusted by a separate connection to a fluid port.

In accordance with still a further embodiment, the cross-sectional geometry of the gastric band 21 may be varied to cover other alternatives. As shown with reference to FIG. 10, the geometry is altered such that the tension element 32 is positioned off center of the compressible material 36, that is, the cross sectional area of the ring 22 itself. By doing this, the tension element 32 takes advantage of rotational torque resulting from the off center positioning and produces mechanical advantages during the constriction of the ring 22.

Figure 11:
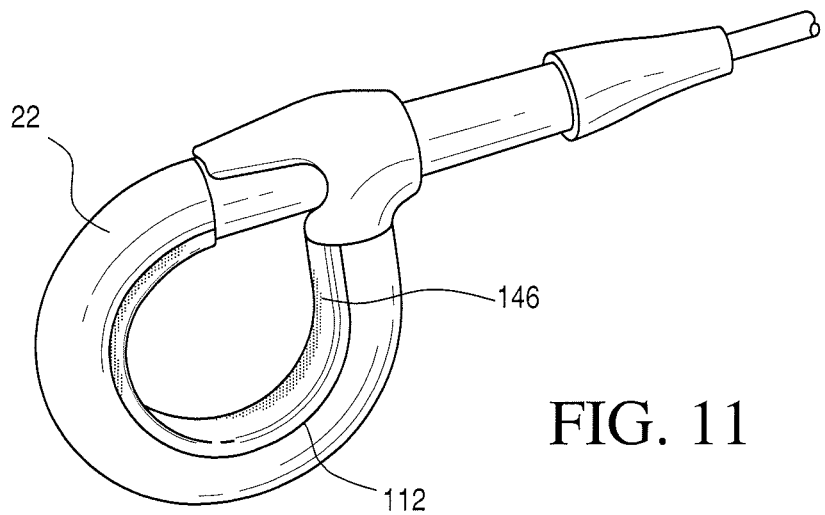
Figure 12:
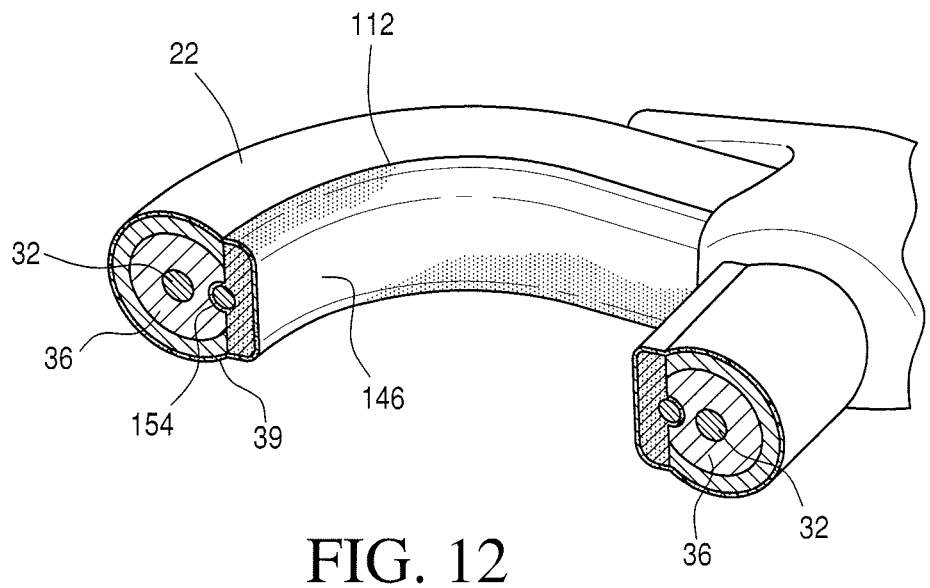
Figures 13, 14:
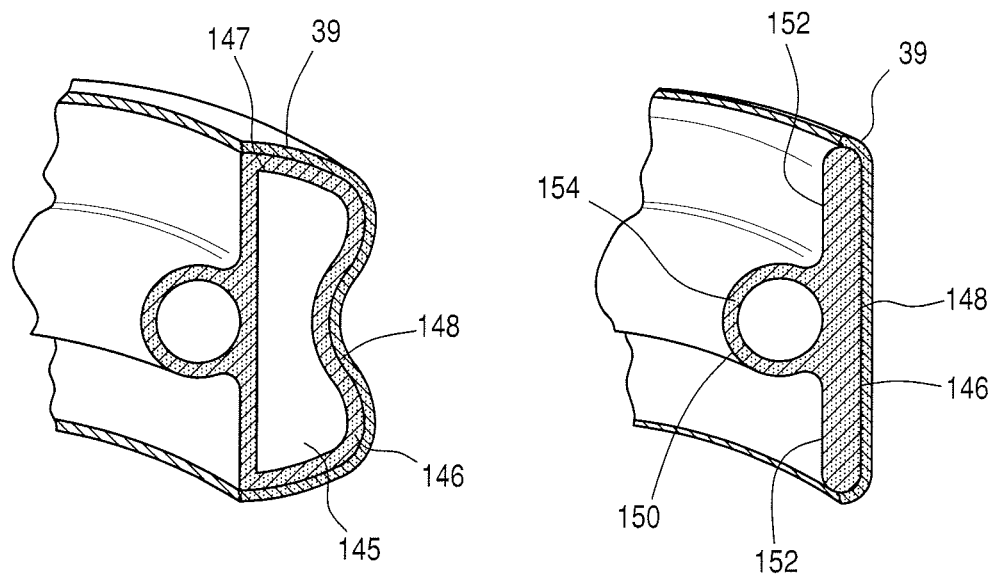

With reference to the embodiments shown with reference to FIGS. 12 and 13, a softer tissue ring interface is achieved by positioning a flexible strip 146 along the inner surface 112 of the ring 22, and between the compressible material 36 and the membrane 39. This strip 146 is designed to spread the forces of the tension element 32 along the entire circumference of the ring 22 and is preferably made from a polymer. With reference to FIG. 11, the strip 146 is placed along the inner surface 112 of the ring 22, and not between the compressible material 36 and the membrane 39. In accordance with a preferred embodiment, the strip 146 includes an inner surface 148 and an outer surface 150. The inner surface 148 is substantially smooth and flat and is adapted to directly face the tissue upon constriction of the ring 22, with the strip 146 positioned between the compressible material 36 and the membrane 39. The outer surface 150 includes substantially flat portions 152 and a central protrusion 154 which is shaped and dimensioned to directly engage the tension element 32 upon constriction thereof. As such, and when the tension element 32 is tightened, the tension element 32 applies pressure directly to the central protrusion 154 of the flexible strip 146. This pressure is transferred along the entire length of the flexible strip 146 such that pressure is evenly distributed along the inner surface 148 of the strip 146. In accordance with yet another embodiment, and with reference to FIG. 14, the inner surface 148 of the strip 146 may take the form of a resilient tubular member 147 with additional compliance. By utilizing such a design, the interior volume 145 defined by the strip 146 may be filled with viscoelastic materials enhancing the compliance of the strip 146 and the overall tissue ring interface.

In accordance with one aspect of the present invention, and with reference to FIGS. 15A, 15B, 16A and 16B, the ring 22 further comprises a layer 40 of a relatively rigid material disposed on the dorsal periphery of the ring 22. The layer 40, which may comprise a plastic or metal alloy, prevents the exterior diameter D of the ring 22 from changing during adjustment of the tension element 32 to reduce the internal diameter (or opening 37) of the ring 22. The layer 40, by its structural rigidity, imposes a circular arc shape for the entirety of the ring 22. Advantageously, the layer 40 allows the tension element 32 to be adjusted following encapsulation of the ring 22 by fibrous tissue after implantation, since adjustment of the internal diameter of the ring 22 does not change the external diameter D of the ring 22.

Figure 15A:
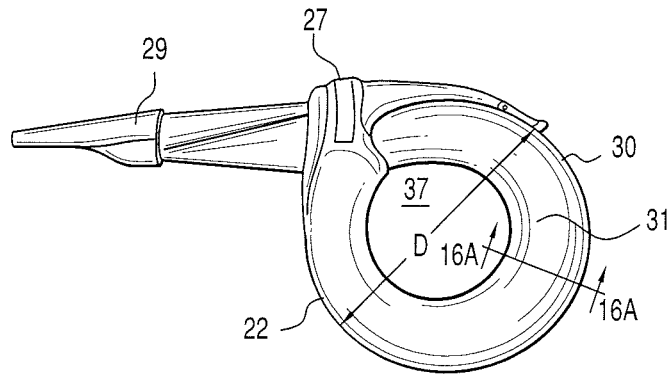
FIGS. 15A and 15B are perspective views illustrating the degree of constriction attainable by the ring of the present invention between the fully open and fully closed positions.
Figure 15B:
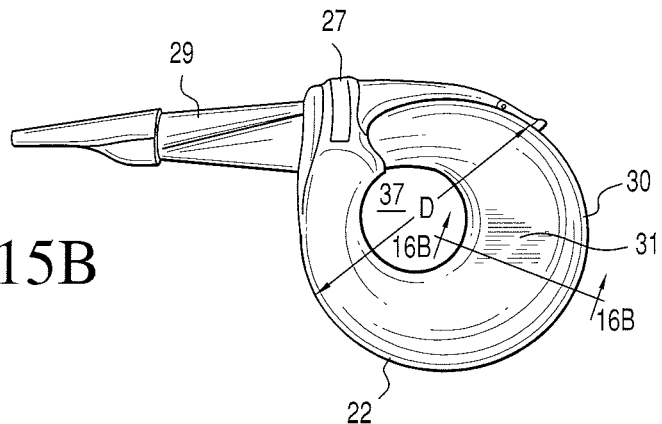

The foregoing feature is illustrated in FIGS. 15A and 15B where the ring 22 is shown in its fully opened and fully closed positions, respectively. As discussed above, the layer 40 forms a rigid skeleton that permits the internal diameter of the ring 22 to change while maintaining the external diameter D constant. Radial movement of the tension element 32 is transmitted to the membrane 39 by the compressible material 36. ePTFE is particularly well-suited for use as the compressible material 36 because it can undergo a 3:1 reduction in length without experiencing a significant increase in cross-section.

Figure 16A:
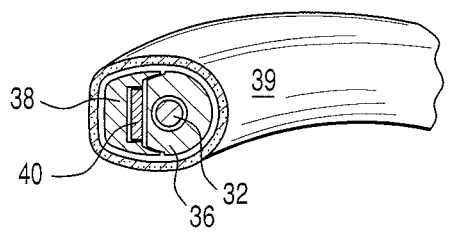
FIGS. 16A and 16B are cross-sectional views of the ring of the present invention along the lines 16A-16A and 16B-16B of FIGS. 15A and 15B, respectively.
Figure 16B:
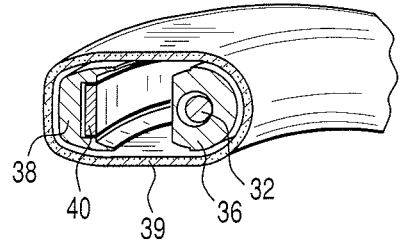

Accordingly, and as depicted in FIGS. 16A and 16B, increase or reduction of the effective length of the tension element 32 results in reversible radial displacement at the internal periphery of the ring 22 opposite the dorsal periphery. This in turn translates into a variation of internal diameter of the ring 22 from a fully open diameter to a fully closed diameter by expanding or controlling the ring 22 to control the tension applied by the ring 22 against a patient's body organ or duct. Preferably, the fully open internal diameter is about 35 mm, and the fully closed internal diameter is about 15 mm. More preferably, the fully open internal diameter is about 29 mm, and the fully closed internal diameter is about 19 mm.

Figure 17:
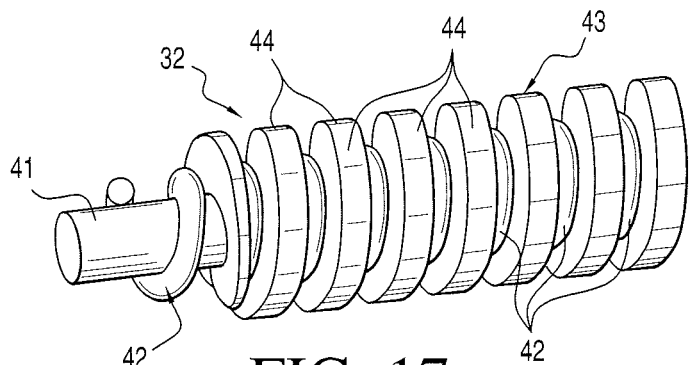
FIG. 17 is a partial perspective view of a screw thread portion of the tension element of the present invention.

Referring now to FIG. 17, the tension element 32 in accordance with a first embodiment is described. This tension element is disclosed in detail in U.S. Patent Application Publication No. 2005/0143766, which is incorporated herein by reference. Briefly, the tension element 32 has sufficient flexibility to permit it to be formed into the substantially circular shape of the ring 22, while also being able to transmit the force necessary to adjust the ring diameter. The tension element 32 therefore comprises a flexible core 41, preferably a metal alloy wire of circular cross section, on which is fixed, and wound coaxially, at least one un-joined coil spring which defines the screw thread pitch.

As shown in FIG. 17, the tension element 32 preferably comprises two un-joined coil springs that form a screw thread: a first spring 42, wound helicoidally along the flexible core 41, and a second spring 43 of greater exterior diameter. The second spring 43 preferably comprises coils 44 of rectangular transverse section, so as to delineate a flat external generatrix. The first spring 42 is interposed between coils 44 of the second spring 43 to define and maintain a substantially constant square screw thread pitch, even when the tension element 32 is subjected to bending.

As a consequence of the foregoing arrangement, the ability of the tension element 32 to maintain a substantially constant thread pitch, when subjected to bending, confers great precision on adjustments of the ring 22. This is especially so when it is realized that as the tension element 32 is drawn through the drive element 35, an ever-increasing curvature is imposed on the remaining portion of the tension element 32. However, because the foregoing arrangement of un-joined coils maintains a substantially constant screw thread pitch, the energy needed to drive the drive element 35 remains low and the efficiency of energy transmission resulting from the use of a square screw thread pitch remains high. In addition, the use of a square screw thread pitch guarantees a stable adjustment position even when the drive element is unpowered.

Figures 18, 19:
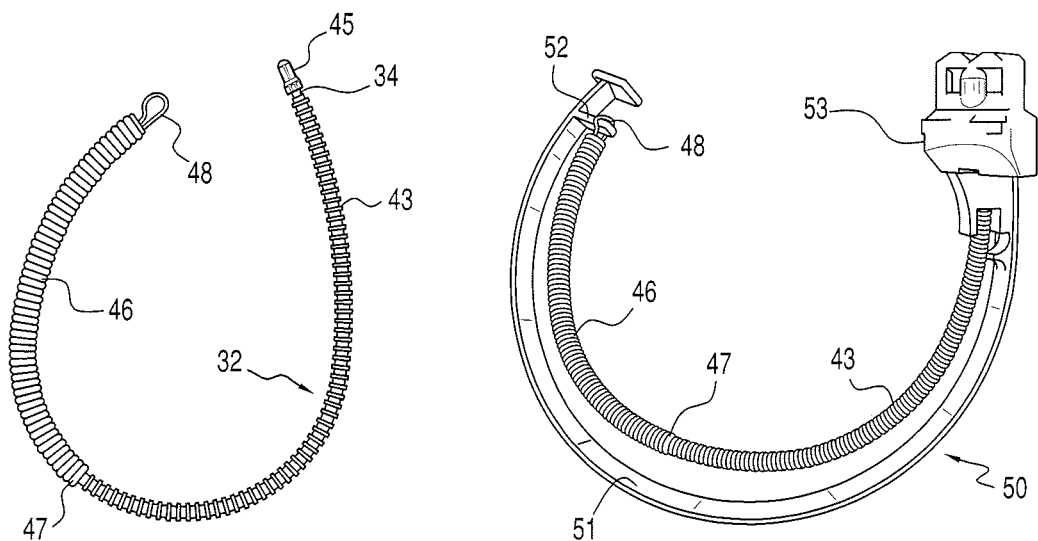
FIG. 18 is a perspective view of an entire tension element suitable for use in the ring of the present invention.
FIG. 19 is a perspective view of the tension element of FIG. 6 coupled to the rigid dorsal peripheral portion and motor housing of the ring.

Referring now to FIG. 18, the tension element 32 is described. The free end 34 includes a crimped cap 45, the second spring 43 has coils with a square transverse section, and the first spring 42 (not visible in FIG. 18, but shown in FIG. 17) is intertwined between the coils of the second spring 43. The flexible core 41 extends through the first and second springs 42, 43, and terminates close to the crimped cap 45. In accordance with one aspect of the present invention, the tension element 32 further comprises a third spring 46 that is coupled to the flexible core 41, and the first and second springs 42, 43 at junction 47. The third spring 46 includes a loop 48 at the end opposite to junction 47, which permits the tension element 32 to be mounted to the first end 26 of the ring 22.

With respect to FIG. 19, the tension element 32 is shown disposed within a skeleton 50 of the ring 22. The skeleton 50 includes a layer 51 that forms the dorsal periphery (corresponding to the layer 40 of FIGS. 2A, 2B, 16A and 16B), an anchor 52 that accepts the loop 48 of the tension element 32, and a drive element housing 53. The skeleton 50 is preferably constructed from a high strength moldable plastic. As further depicted in FIG. 19, the skeleton 50 extends along a greater arc length than the tension element 32. In accordance with another aspect of the present invention, the third spring 46 permits the gastric band 21 to be straightened for insertion through a standard 18 mm trocar, despite the differential elongation of the skeleton 50 and the tension element 32. This feature is illustrated in FIG. 20, which depicts the ring 22 inserted through 18 mm trocar 55 so that the ring 22 is substantially straight.

Referring now to FIG. 21, the housing 29 of the free end of the ring 22 is described. The housing 29 comprises an elastomeric material, such as silicone, having a recessed portion 56, a tension element cavity 57 and a cable lumen 58. The recessed portion 56 is configured to accept the drive element housing 53 of the skeleton 50, so that as the tension element 32 is drawn through the drive element 35 it extends into the tension element cavity 57. A cable lumen 58 extends through the housing 29 so that the antenna cable 24 may be coupled to the drive element 35. The housing 29 preferably may be grasped in area G using atraumatic laparoscopic graspers during manipulation of the gastric band 21.

In FIG. 22, the drive element housing 53 of the skeleton 50 is shown with the drive element 35 and the tension element 32 disposed therethrough. The antenna cable 24 is coupled to a motor (not shown) disposed within the drive element housing 53. The tension element 32 is in the fully opened (largest diameter) position, so that the crimped cap 45 contacts the printed circuit board 59 of the reference position switch, described below with respect to FIG. 26.

Because the tension element 32 must be drawn through the drive element 35 to cause tightening thereof, the tension element 32 described above necessarily requires that the tail end 34, that is, the end nearest crimped cap 45, of the tension element 32 extends beyond the drive element 35 with the extending portion increasing as the ring 22 is tightened, making potential interference with the viscera possible. In addition, the tension element 32 may cause localized stress to the inside surface, for example, the compressible material 36, of the gastric band 21 as well as potentially to the viscera.

Figure 24:
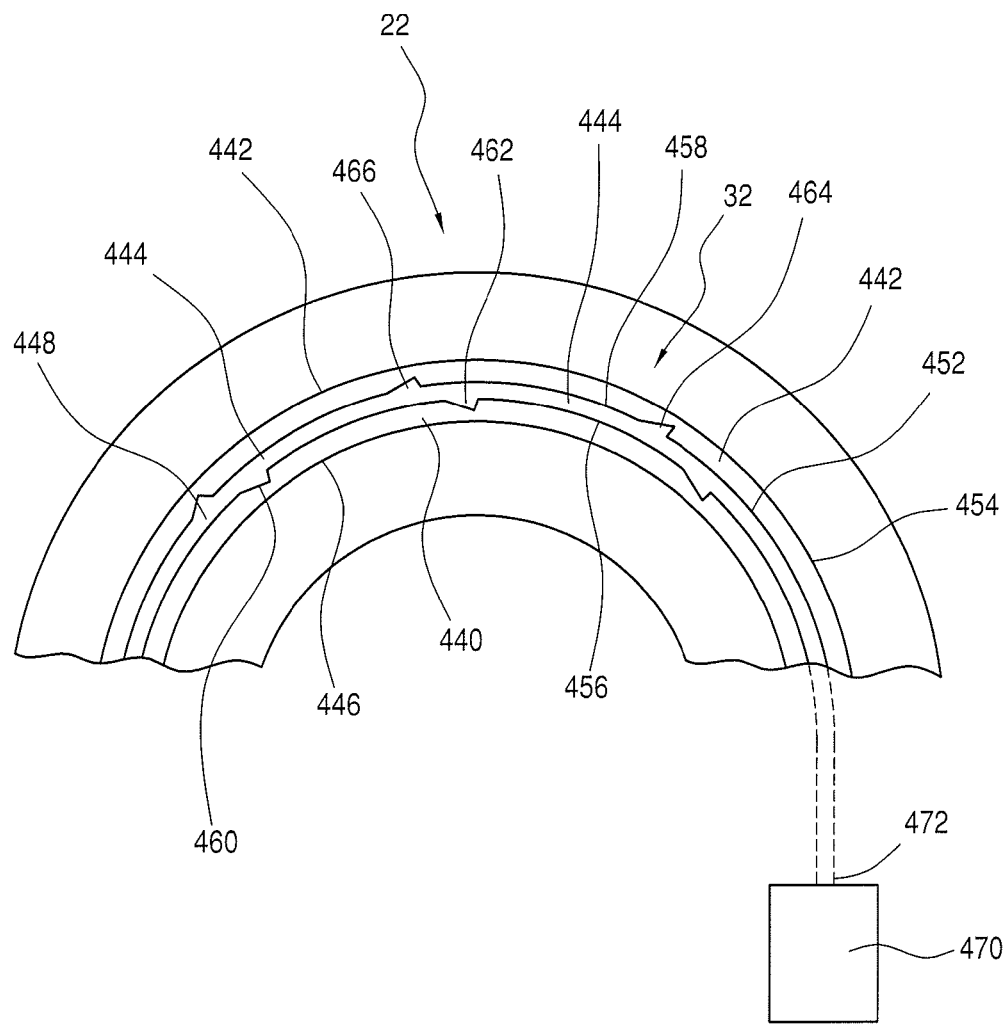
FIG. 24 is a cross-sectional view of a tension element in accordance with an alternate embodiment.

In accordance with an alternate embodiment and with reference to FIG. 24, the diameter of the ring 22 is adjusted without the need for a tension element including a tail end which is extended and retracted as the need for adjustments in the diameter of the ring 22 are desired. The tension element 32 in accordance with this embodiment is composed of an inner first strap member 440, an outer second strap member 442 and a camming strap member 444 moveably positioned therebetween. The first strap member 440 includes an inner surface 446 and an outer surface 448, the second strap member 442 includes an inner surface 452 and an outer surface 454, and the camming strap member 444 includes an inner surface 456 and an outer surface 458. The inner surface 446 of the first strap member 440 is substantially smooth and is shaped and dimensioned for facing the tissue which the ring 22 engages. The outer surface 448 of the first strap member 440 includes a plurality of recessed camming surfaces 460 shaped and dimensioned for interacting with protruding camming 462 surfaces extending from the inner surface 456 of the camming strap member 444. Similarly, the outer surface 454 of the second strap member 442 is substantially smooth and is shaped and dimensioned for facing the tissue which the ring 22 engages. The inner surface 452 of the second strap member 442 includes a plurality of recessed camming surfaces 464 shaped and dimensioned for interacting with protruding camming surfaces 466 extending from the outer surface 454 of the camming strap member 444.

As discussed above, the camming strap member 444 is shaped and dimensioned for positioning between the first strap member 440 and the second strap member 442 in manner such that the camming strap member 444 is in sliding contact with the first and second strap members 440, 442 but is free to move relative thereto. As such, when the camming strap member 444 moves circumferentially relative to the first and second strap members 440, 442, the protruding camming surfaces 462, 466 of the camming strap member 444 interact with the recessed camming surfaces 460, 464 of the respective first and second strap members 440, 442. As a result of this interaction, the first strap member 440 is caused to move inwardly or outwardly selectively decreasing or increasing the effective diameter of the ring 22.

Controlled movement of the camming strap member 444 is achieved by a drive element 470 secured at the first end 472 of the camming strap member 444. In accordance with a preferred embodiment, the drive element 470 is a conventional drive mechanism, for example, screw drive, friction belt drive, servomotor, etc.

It is further contemplated the recessed camming surfaces 460, 464 and the protruding camming surface 462, 466 may be adjusted in height and location along the circumference of the tension element 32 so as to adjust the ability of the tension element 32 to control adjustments in the diameter of the ring 22. That is, the total adjustment range of the tension element 32 will depend on the configuration of the recessed and protruding camming surfaces 460, 462, 464, 466, specifically, the number of camming surfaces and the height of the camming surface. In the simplest case the adjustment diameters could be described as $\theta_i$=original diameter
h=height of wedge
$\theta_f$=final diameter
$\theta_f=\theta_i+2(h)$ This tension element 32 construction offers a variety of advantages, including: the cost of the flexible spring assembly disclosed with reference to other embodiments can be avoided and the total throw of the motor can be reduced therefore reducing the length of the tail section. Multiple camming surface configurations can be adapted to the design to achieve different adjustment ranges while a constant pressure profile on the restricted tissue can be is maintained.

Drive Element

Figure 25:
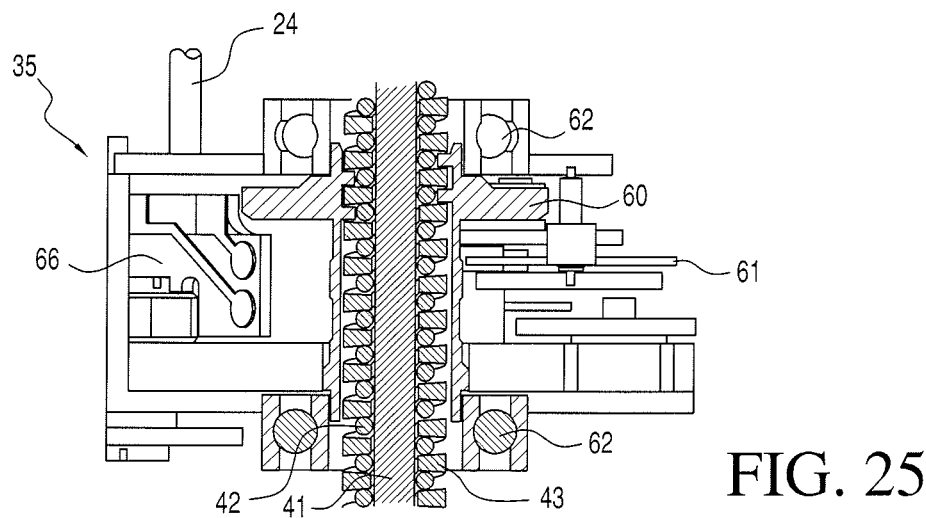
FIG. 25 is a cross-sectional view depicting the construction of the drive element of FIG. 23.
Figure 26:
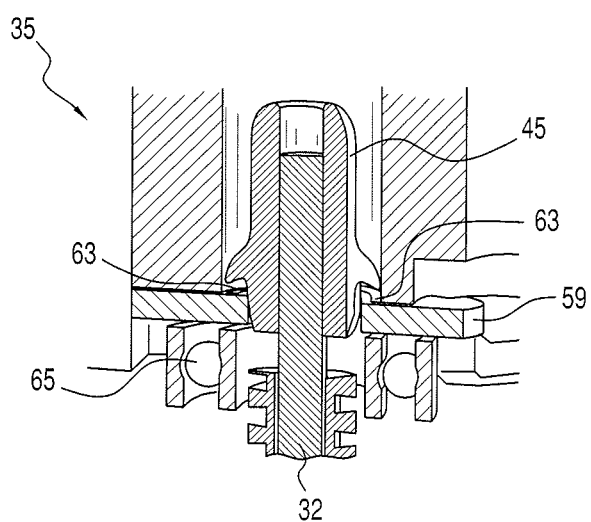
FIG. 26 is a cross-sectional view depicting the construction of the reference position switch.

With respect to FIGS. 25 and 26, the drive element 35 used in conjunction with the tension element 32 disclosed with reference to FIGS. 22 and 23, includes a motor 66 coupled to the antenna cable 24 that drives the nut 60 through the gears 61. As with the various embodiments presented throughout the present disclosure, the motor may take a variety of forms including, but not limited to a stepper motor and piego motor. The nut 60 is supported by upper and lower bearings 62 to minimize energy losses due to friction. The nut 60 is self-centering, self-guiding and provides high torque-to-axial force transfer. The drive element 35 is disclosed in greater detail with reference to U.S. Patent Application Publication No. 2005/0143766, entitled "TELEMETRICALLY CONTROLLED BAND FOR REGULATING FUNCTIONING OF A BODY ORGAN OR DUCT, AND METHODS OF MAKING, IMPLANTATION AND USE", which is incorporated herein by reference.

Referring now to FIG. 26, the reference position switch of the present banding system 1 is described. Because the drive element 35 of the present banding system 1 employs a nut 60 driven by a stepper motor 66, there is no need for the system to include a position sensor or encoder to determine the length of the tension element 32 drawn through the drive element 35. Instead, the diameter of the ring 22 may be directly computed as a function of the screw thread pitch and the number of rotations of the nut 60. To ensure an accurate calculation of the degree of restriction imposed by the ring 22, however, it is desirable to provide at least one reference point.

This reference datum is accomplished in the ring 22 of the present invention using a reference position switch that is activated when the ring 22 is moved to its fully open position. The crimped cap 45 on the free end of the tension element 32 serves this function by contacting electrical traces 63 on the printed circuit board 59 (and also limits elongation of the screw thread). The circuit board 59 is disposed just above the bearing 65, which forms part of the drive element 35 (see also FIG. 22). When the crimped cap 45 contacts the traces 63, it closes a switch that signals the implantable controller that the ring 22 is in the fully open position.

In accordance with an alternate embodiment, and with reference to FIG. 27, a symmetrical drive system 170 is employed. Briefly, and in accordance with a preferred embodiment of the present invention, the drive system 170 employs two flexible members 172, 174 which, in accordance with a preferred embodiment of the present invention, are flexible screws simultaneously operating upon the tension element 32 using a single motor 176 with a dual actuated drive 178, 180. The dual actuated drives 178, 180 provide directional control for loosening or tightening the flexible members 172, 174. In accordance with a preferred embodiment of the present invention, the body of the tension element 32 is constructed in substantially the same manner as that described with reference to the embodiment shown in FIGS. 17, 18 and 19. However, and considering the flexible members interact with the dual actuated drives for controlled construction and expansion of the ring 22, the body of the tension element may be constructed of various materials and may be constructed without departing from the spirit of the present invention. However, and as will be appreciated based upon the following disclosure, flexible first and second screws 172, 174 are secured to the opposite ends 183, 194 of the tension element 32 allowing for actuation in accordance with the embodiment disclosed herein.

By drawing the tension element 32 at both ends, and simultaneously applying pressure to the opposite ends, the applied tension is uniformly distributed along the length of the tension element 32.

More particularly, a flexible first screw 172 is provided at one end of the tension element 32. The first screw 172 includes a first end 182 and a second end 184. The first end 182 is secured to a first end 183 of the tension element 32 and the second end 184 is fed into a first actuated drive 178 of the motor 176. Similarly, the flexible second screw 174 includes a first end 186 and a second end 188. The first end 186 is secured to a second end 194 of the tension element 32 and the second end 188 is fed into a second actuated drive 180 of the motor 176. With the first and second ends 183, 194 of the tension element 32 respectively secured to the first end 182 of the first screw 172 and the first end 186 of the second screw 174, and the motor 176 connecting the second ends 184, 188 of the first and second screws 172, 174, a complete circular loop is created. The effective circumference of the circular loop is, therefore, readily adjusted by manipulating the extent to which the first and second screws 172, 174 are drawn into the first and second actuated drives 178, 180 of the motor 176.

As briefly discussed above, the motor 176 is provided with first and second actuated drives 178, 180. The first and second actuated drives 178, 180 include respective inputs 195, 196 that are positioned on opposites sides of the motor 176 for receiving the second ends 184, 188 of the respective first and second screws 172, 174. As such, the second end 184 of the first screw 172 is fed into the input 195 of the first actuated drive 178 where it is engaged by a drive mechanism (for example, a screw drive in accordance with a preferred embodiment of the present invention). The second end 188 of the second screw 174 is fed into the input 196 of the second actuated drive 180 where it is engaged by a drive mechanism (for example, a screw drive in accordance with a preferred embodiment of the present invention).

In accordance with a preferred embodiment, the drive mechanisms of the first actuated drive 178 and the second actuated drive 180 employ nut-like features upon which a threaded surface of the first and second screws 172, 174 ride so as to push or pull the first and second screws 172, 174 through the motor body. When the motor 176 is energized, the first and second screws 172, 174 move in opposite directions and tighten the tension element 32 about a central axis of the ring 22. Because both screws 172, 174 move at the same time, the tension element 32, and ultimately, the gastric band 21, can be adjusted twice as fast as a single direction screw with the same amount of work.

With the first screw 172 engaged by the drive mechanism of the first actuated drive 178 and the second screw 174 engaged by the drive mechanism of the second actuated drive 180, actuation of the motor 176 is controlled to actuate the first and second actuated drives 178, 180 to either simultaneous draw the first and second screws 172, 174 into the motor 176 or the simultaneous push the first and second screws 172, 174 out of the motor 176 for either decreasing or increasing the effective circumference of the tension element 32.

By employing the embodiment described above, symmetrical movement allows for a more uniform distribution of force on the tension element 32. The tension element 32 is also fixedly secured to the ring 22 at an anchor point 175 diametrically opposite the motor 176. In this way, the first and second screws 172, 174 connected to the tension element 32 pull the membrane 39 of the ring 22 uniformly inward or outward from the anchor point 175 diametrically opposite the motor 176 of the gastric band 21. It should be noted that is contemplated that the anchor point is not limited to the top of the gastric band but may be located at one side or opposite the motor drive.

In accordance with an alternate embodiment as shown with reference to FIGS. 28 and 29, the drive system 170 includes a tension element 32 composed of two flexible members (referred to as springs) 202, 204. The springs 202, 204 are linked together so as to define the tension element 32 used in increasing or decreasing the circumference of the ring. The flexible first member 202 is threaded externally like a bolt (inner spring) and the flexible second member 204 is internally threaded like a nut (outer spring). The inner spring 202 is shaped and dimensioned to seat within the outer spring 204 in a manner coupling the inner and outer springs 202, 204 but allowing rotation of the outer spring 204 relative to the inner spring 202 for controlled adjustment of their relative positions as discussed below in greater detail.

More particularly, the outer spring 204 is attached to a rotational motor 176 with the inner spring 202 threaded into the outer spring 204. As the motor 176 turns the inner spring 202 is either drawn farther into or pushed farther out of the outer spring 204 to either reduce or increase the diameter of the stoma defined by the ring 22. To prevent total restriction of the stomach, the outer spring 204 or inner spring 202 is provided with a hard stop 206 that will prevent further restriction. It will be appreciated that the inner and outer springs could also be thought of as a flexible screw and flexible nut.

Figure 30:
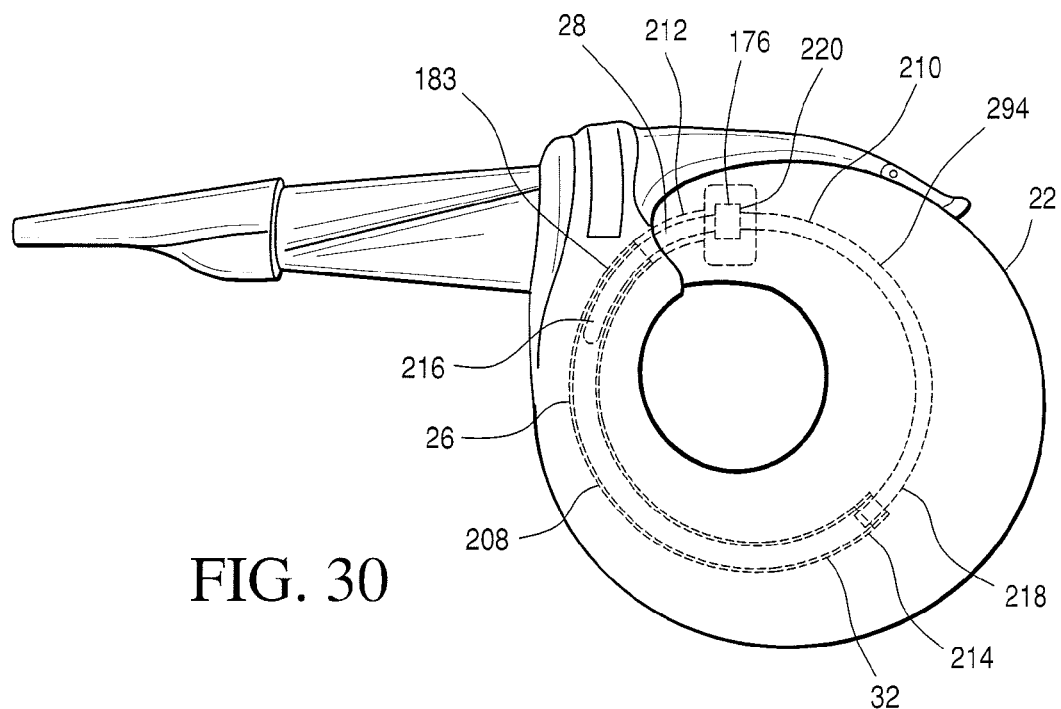
Figure 31:
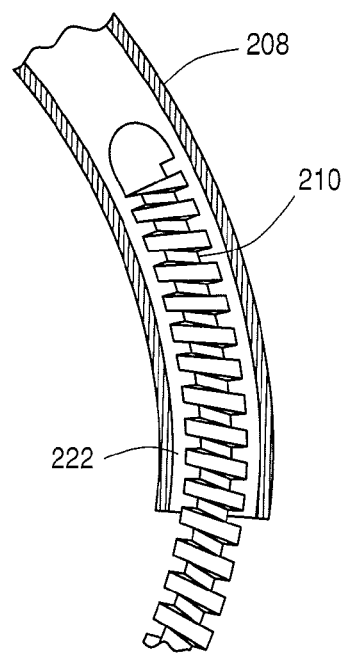

Referring now to FIGS. 30 and 31, yet another embodiment is disclosed. In accordance with this embodiment, the tension element 32 mounted within the ring 22 is provided with a flexible hollow threaded shaft 208 at its first end 26 and a flexible threaded shaft 210 at its opposite second end 28. The threaded shaft 210 is movably coupled to a drive motor 176 secured at the free end 212 of the hollow threaded shaft 208 for controlling movement of the first end 283 of the tension element 32 relative to the second end 294 of the tension element 32.

More particularly, the hollow threaded shaft 208 defining the first end 283 of the tension element 32 includes a free end 212 and a coupled end 214, while the threaded shaft 210 defining the second end 194 of the tension element 32 includes a free end 216 and a coupled end 218. The coupled end 214 of the hollow threaded shaft 208 is secured to the coupled end 218 of the threaded shaft 210.

A drive motor 176 is secured to the free end 212 of the hollow threaded shaft 208. The drive motor 176 includes an input passageway 220 shaped and dimensioned to guide the threaded shaft 210 therethrough and into the cavity 222 defined by the hollow threaded shaft 208. As such, and with the threaded shaft 210 engaged with the drive motor 176, the drive motor 176 is actuated to either draw into or push threaded shaft 210 out of the hollow threaded shaft 208 to either reduce or increase the diameter of the stoma defined by the ring 22. To prevent excessive inward or outward movement, it is contemplated the threaded shafts may be provided with a hard stop(s) (not shown). Additionally, to facilitate connection to the coupled end of the hollow shaft a tapered lead end feature may be added to the free end of the threaded shaft. Similarly, it is further contemplated the hollow threaded shaft may have a cone like feature to more readily facilitate alignment to the threaded shaft during connection.

In accordance with yet a further embodiment and with reference to FIGS. 32 to 38, a quick connect coupling 224 for use in conjunction with a screw drive mechanism 226 is employed. The quick connect coupling 224 is a snap-together feature molded into a central segment 228 of the ring 22.

More particularly, the ring 22 contains the silicone sleeve that interacts with the patient's stomach to create the gastric band 21, but the ring 22 is split at the central segment 228 to allow for controlled splitting of the ring 22 in a manner allowing for ease of deployment and ease of removal. As with the embodiments discussed above, a tension element 32 extends within the ring 22 and similarly includes a split in the central segment 228. Accordingly, the ring 22 may be thought of as including a first segment 230 and a second segment 232. The first segment 230 includes a first end 234 and a second end 236 and the second segment 232 includes a first end 240 and a second end 242. The tension element 32 is similar composed of a first tension segment 244 and a second tension segment 246. The first tension segment 244 includes a first end 248 and a second end 250 and the second tension segment 246 includes a first end 252 and second end 254. The first end 234 of the first segment 230 and the first end 240 of the second segment 238 are linked at the motor 176 that couples the first end 248 of the first tension segment 244 to the first end 252 of the second tension segment 246. Completing the circle defined by the ring and tension elements 230, 232, the second ends 236, 250 of the first segment 230 and first tension segment 244 and the second ends 242, 254 of the second segment 232 and second tension segment 246 are linked via the quick connect coupling 224.

In practice, the gastric band 21, with the quick connect coupling 224 disconnected allows the second ends 236, 242 of the first and second segments 230, 232 of the ring 22 to move freely relative to each other. Thus, the ring 22 can be positioned adjacent the stomach and the quick connect coupling 224 is used by the surgeon to first place and attach the gastric band 21 during surgery. The first end 248 of the first tension segment 244 and the first end 252 the second tension segment 246 each terminate with a drive screw 256. The drive screws 256 engage the drive motor 176 and are actuated thereby. The motor 176 may then be used to open and close the gastric band 21 about the stomach of the user.

It is contemplated the first and second tension segments 244, 246 could be made of braided cable, laminate polymers, or even a single wire. The body of the first and second tension segments 244, 246 may be substantially wider than the drive screw 256 to uniformly distribute the load. The non-braided version will be more susceptible to fatigue and failure so appropriate materials like nylon may need to be used. As discussed herein in greater detail, the first and second tension segments 244, 246 are housed within a center molded cavity of the gastric band 21 that allows them to slip with respect to the gastric band 21 so that as they are tightened stress does not build up in the silicone outer sleeve that would tend to wrinkle or fold the outer membrane.

With regard to the drive motor 176, it is housed within a pocket in the middle of the gastric band 21 and is secured to the first end 234 of the first segment 230 of the ring 22. The motor housing 258 is grounded and attached to the housing sleeve 260 so that when energy or power is applied; the motor shaft 262 rotates, not the motor housing 258. The motor housing 258 is attached to a drive screw 267 that is coupled to the opposite first ends 248, 252 of the first and second tension segments 244, 246. If one polarity is applied, the motor shaft 262 rotates in a first direction and the system is tightened drawing the first ends 248, 252 of the respective first and second tension segments 244, 246 toward one another. If the opposite polarity is applied, the motor shaft 262 rotates in a second direction opposite to the first direction and the system loosens, pushing the first ends 248, 252 of the respective first and second tension segments 244, 246 away from one another. The drive thread configuration can be changed to allow for different speed or torque ratios of the motor to the linear travel of the screws. This will also prevent back travel when the motor is not energized due to the inertia within the motor itself. Additionally, if power is always present, it is contemplated active braking could be incorporated by applying the same polarity to both poles of the motor thereby increasing its holding strength, although usage of power for braking might not be practical in certain application as it would consume power more quickly. It is further contemplated this could also be achieved passively by using a stepper motor which would inherently braking when power is removed.

In accordance with an alternate embodiment as shown with reference to FIG. 34, a tightening nut 261 is rotated around the outside of the first and second tension segments 244, 246 and has a worm gear 263 coupled to the motor (not shown). The worm gear 263 prevents back travel and forces cannot be passed from the tension segments 244, 246 back to the motor if the motor is not moving the disclosed worm gear configuration. Rotation in either direction by the motor drive shaft 265 linearly moves the screw head ends 248', 252' of the first and second tension segments 244, 246 towards each other or away from each other since the first and second tension segments 244, 246 are not actually rotated. It is contemplated the threading on the ends of the first and second tension segments may not be circumferential but only on one side. This would improve guidance and prevent slipping of the threads.

It is further contemplated the screw ends could be connected to drive cables forming the tension segments by crimping the metal thread end to the drive cable, or it could be overmolded plastic if the resulting threading was strong enough to work in conjunction with the drive. It could also be molded in the system as a hole with long fiber filler added to the plastic to improve its tension capabilities.

Figure 35:
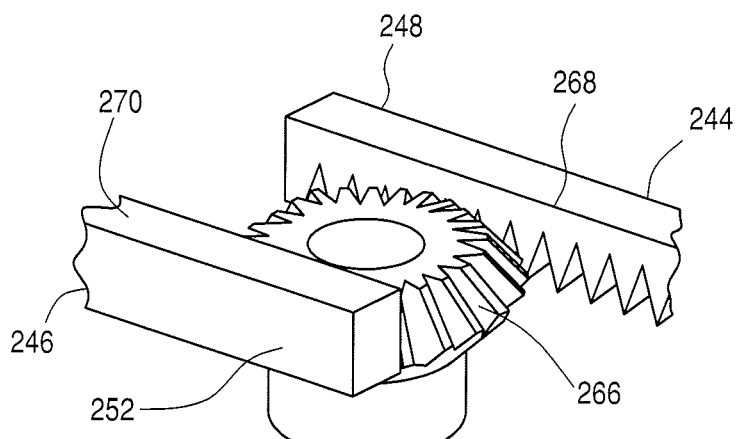

Referring to FIG. 35, and in accordance with another drive structure for use in accordance with the system described with reference to FIGS. 32 and 33, a drive 266 with an angled beveled gearing surface is connected to a motor 176 which is in turn connected to the outer portion of a gastric band 21. In this configuration, angled racks 268, 270 are formed along the first ends 248, 252 of the first and second tension segments 244, 246 of the gastric band 21. As the motor 176 rotates, both ends 248, 252 of the first and second tension segments 244, 246 of the gastric band 21 are drawn inward at the same speed if the motor 176 were to rotate in a first direction, for example, counterclockwise orientation, and the gastric band 21 is uniformly tightened.

Figure 36:
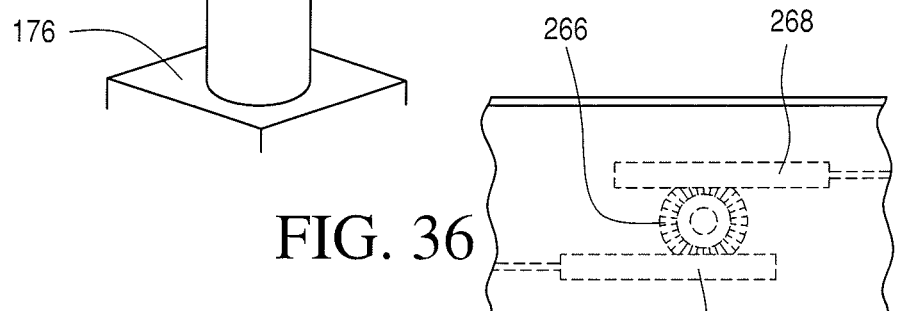

With reference to FIG. 36, it is contemplated the beveled gearing surface of the drive 266 may be oriented at a 90° angle from the above embodiment such that the angled racks 268, 270 are drawn over top of one another. The angled racks 268, 270 in these embodiments require a track with low friction by which they can travel linearly with respect to each other. This track would also ensure that there is a solid connection to the beveled gear and that no slippage occurs.

Figure 37:
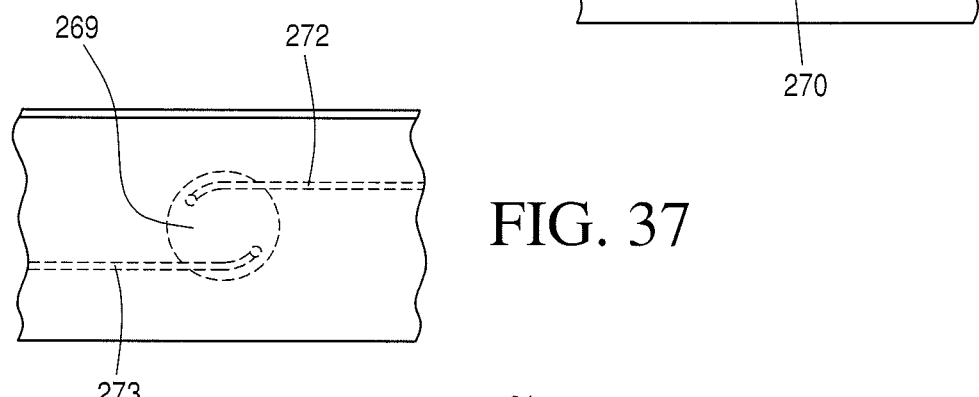

In accordance with an alternate embodiment, and with reference to FIG. 37, the angled racks 268, 270 (shown above with reference to FIGS. 35 and 36) are replaced by high strength cables 272, 273 and connected directly around a motor shaft 269 in a manner similar to a winch system. The alternative could reduce the complexity of the design as the cables would not require tight tolerances and there would be no concern that the racks could slip from the winch.

Figure 38:
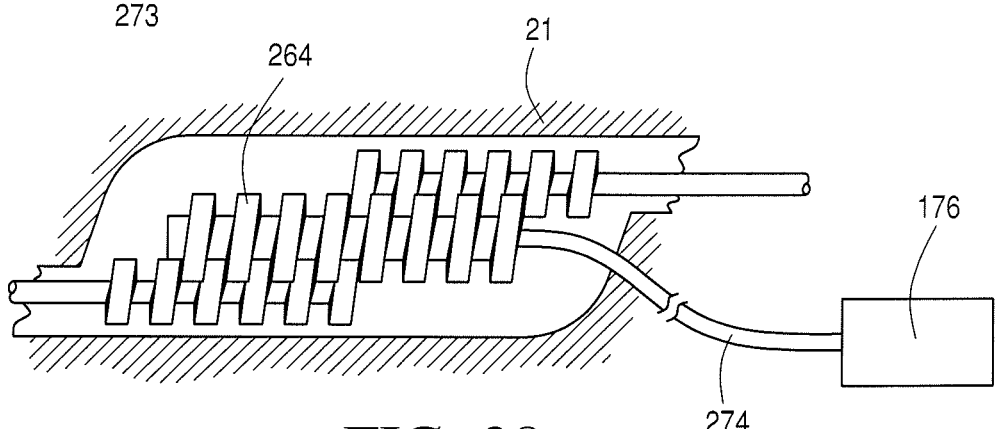

In accordance with yet another embodiment, and with reference to FIG. 38, the motor 176 is external to the gastric band 21 and has a flexible drive cable 274 that rotates any internal gears, racks, pinions, etc. (shown with reference to the drive of FIG. 33, although other drive systems are contemplated). The drive cable 274 is capable of providing adequate torque to the drive screw 264 in order to tighten the gastric band 21. The flexible cable drive would be similar to that found on the Johnson & Johnson Mammotome™ MR product. This flexible drive cable could be implemented into several other embodiments as well when coupled with the appropriate hardware at each of the ends.

While the drive element 35 of the present ring 22 is robust and not prone to failure, it may at times be necessary to release the tension element 32 in an emergency. The release of the tension element 32 would provide for immediate release of tension applied by the ring 22 to the stomach and permit removal of the ring 22 from its position about the stomach.

In accordance with a first embodiment of a tension element release system and with reference to FIGS. 39, 40 and 41, the tension element 32 includes a free end 34 and a fixed end 33. The fixed end 33 is secured adjacent the first end 26 of the ring 22 via a release mechanism 312 allowing selective release of the fixed end 33 of the tension element 32 from the first end of the ring 22 for release of tension being applied by the ring 22. The release mechanism 312 includes a jaw mechanism 314 that selectively engages the fixed end 33 of the tension element 32. The fixed end 33 is provided with a bulbous head 316 that is selectively seated within the jaw mechanism 314 in the manner discussed below in greater detail.

The jaw mechanism 314 includes a fixed jaw member 318 and a movable jaw member 320. A jaw drive element 322 is positioned between the fixed jaw member 318 and the movable jaw member 320. The fixed jaw member 318 is substantially L-shaped and includes a first leg 324 and a second leg 326 oriented perpendicular to each other. Similarly, the movable jaw member 320 is substantially L-shaped and includes a first leg 328 and a second leg 330 oriented perpendicular to each other. The fixed jaw member 318 and the movable jaw member 320 sit facing each other in a mirror like orientation with the first legs 324, 328 of the respective fixed jaw member 318 and the movable jaw member 320 substantially parallel to each other and the second legs 326, 330 of the respective fixed jaw member 318 and the movable jaw member 320 facing each other in an aligned manner. By adopting this orientation, the fixed jaw member 318 and the movable jaw member 320 create a cavity in which the enlarged head 316 of the tension element 32 may sit while the remainder of the tension element 32 extends through the opening 332 formed between the free ends 334, 336 of the respective second legs 326, 330 of the fixed jaw member 318 and movable jaw member 320. As will be appreciated based upon the following disclosure, a spring 321 biases the movable jaw member 320 toward the fixed jaw member 318 maintaining the free ends 334, 336 of the respective second legs 326, 330 of the fixed jaw member 318 and movable jaw member 320 in proximity to each other for holding the enlarged head 316 of the tension element 32 until it is desired to release the tension element 32.

When one desires to release the tension element 32, that is, release the enlarged head 316 of the tension element 32 from its position between the fixed jaw member 318 and the movable jaw member 320, the jaw drive element 322 is expanded in a manner pushing the movable jaw member 320 away from the fixed jaw member 318. As the movable jaw member 320 is pushed away from the fixed jaw member 318, that is, as the jaw mechanism 314 is moved from its locked orientation with the fixed jaw member 318 and movable jaw member 320 in close proximity to its release orientation with the fixed jaw member 318 and movable jaw member 320 moved away from each other, the opening 332 therebetween expands until it is larger than the enlarged head 316 of the tension element 32 at which time the fixed end 33 of the tension element 32 is released from its position between the fixed jaw member 318 and the movable jaw member 320.

In accordance with a preferred embodiment, the jaw drive element 322 is a balloon 338 which may be selectively expanded for engagement with the fixed jaw member 318 and the movable jaw member 320 in a manner selectively moving the fixed jaw member 318 and the movably jaw member 320 to their release orientation. While a particular jaw drive element 322 is disclosed above in accordance with a preferred embodiment of the present invention, it is contemplated other drive element mechanisms may be employed without departing from the spirit of the present invention.

Figures 42, 43:
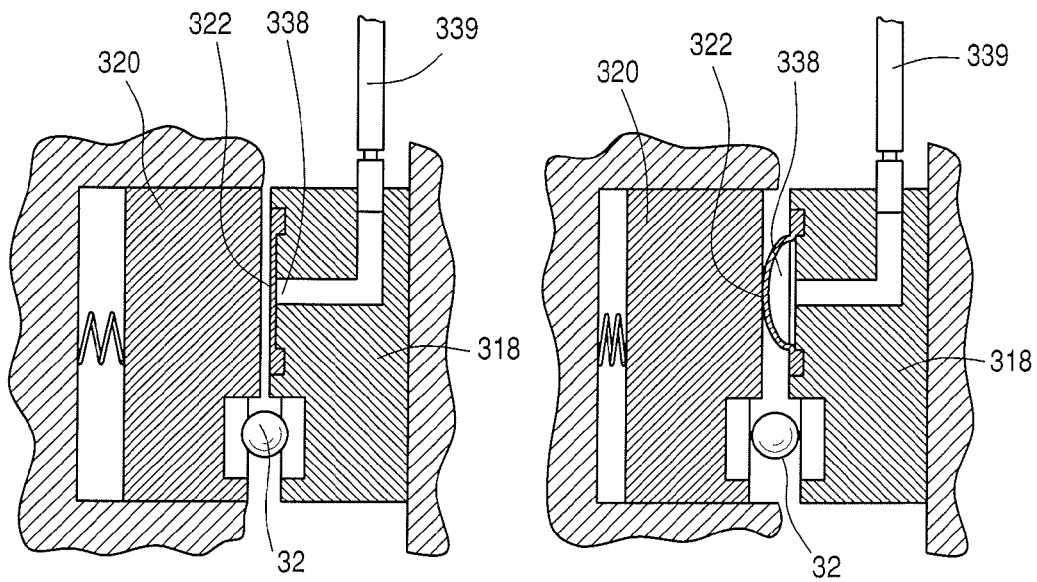

For example, and in accordance with an alternate embodiment shown with reference to FIGS. 42 and 43, the jaw drive element 322 might take the form of a balloon 338 secured to the fixed jaw member 318, which upon expansion presses against the movable jaw member 320 to place the jaw mechanism 314 in its release orientation. It is contemplated such a balloon 338 would be constructed of silicone and be supplied with fluid for expansion via a catheter 339 extending along the present apparatus.

Figures 44, 45:
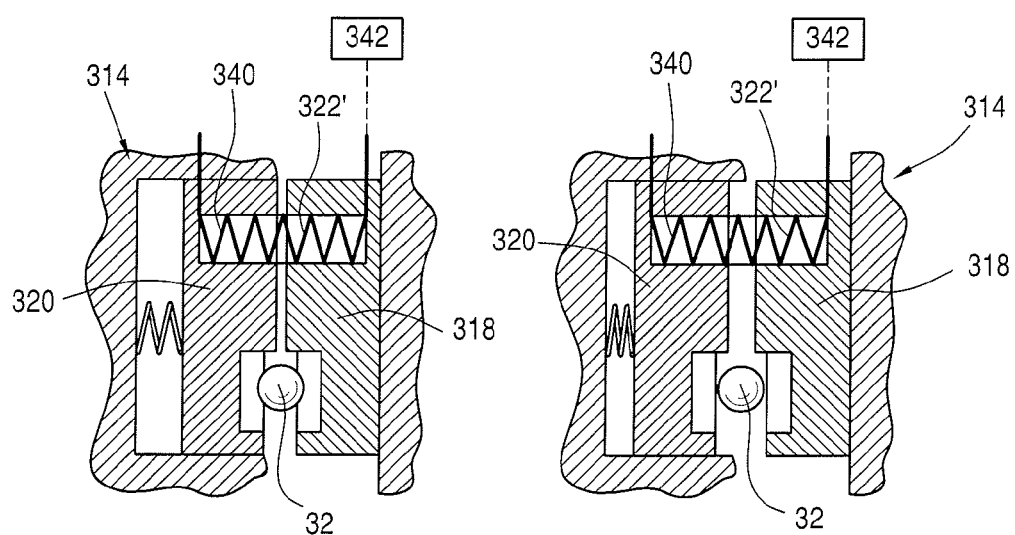

Another jaw drive element 322' is shown with reference to FIGS. 44 and 45. In accordance with this embodiment, a shape memory alloy spring 340 is positioned between the fixed jaw member 318 and the movable jaw member 320. The spring 340 is linked to a source of electricity 342. Upon application of the a voltage across the spring 340, the spring 340 will change shape, for example, and in accordance with a preferred embodiment, expand, forcing the fixed jaw member 318 and movable jaw members 320 apart in a manner moving the jaw mechanism 314 to its release orientation.

In accordance with an alternate embodiment as shown with reference to FIGS. 46-48, the jaw mechanism 314 includes a first movable jaw member 320a and a second movable jaw member 320b. The first movable jaw member 320a and the second movable jaw member 320b are pivotally connected with first and second spring biasing members 344a, 344b forcing them toward one another. A jaw drive element 322 is positioned between the first movable jaw member 320a and the second movable jaw member 320b.

The first movable jaw member 320a is substantially L-shaped and includes a first leg 324a and a second leg 326a oriented perpendicular to each other. Similarly, the second movable jaw member 320b is substantially L-shaped and includes a first leg 324b and a second leg 326b oriented perpendicular to each other. Each of the first and second movable jaw members 320a, 320b include a laterally extending flange 346a, 346b through which a pivot pin 348 extends for pivotally linking the first movable jaw member 320a to the second movable jaw member 320b in a manner described above. The first movable jaw member 320a and the second movable jaw member 320b sit facing each other in a mirror like orientation with the first legs 324a, 324b of the respective first and second movable jaw members 320a, 320b substantially parallel to each other and the second legs 326a, 326b of the respective first and second movable jaw members 320a, 320b facing each other in an aligned manner. By adopting this orientation, the first and second movable jaw members 320a, 320b create a cavity in which the enlarged head 316 of the tension element 32 may sit while the remainder of the tension element 32 extends through the opening 332 formed between the free ends 334, 336 of the respective second legs 326a, 326b of the first and second movable jaw members 320a, 320b. As will be appreciated based upon the following disclosure, the first and second movable jaw members 320a, 320b are biased toward each other maintaining the free ends 334, 336 of the respective second legs 326a, 326b of the first and second movable jaw member 320a, 320b in proximity to each other for holding the enlarged head 316 of the tension element 32 until it is desired to release the tension element 32.

When one desires to release the tension element 32, that is, release the enlarged head 316 of the tension element 32 from its position between the first and second movable jaw members 320a, 320b, the jaw drive element 322 is expanded in a manner pushing the first and second movable jaw members 320a, 320b away from each other. As the first and second movable jaw members 320a, 320b are pushed away from each other, that is, as the jaw mechanism 314 is moved from its locked orientation with the first and second movable jaw members 320a, 320b in close proximity, to its release orientation with the first and second movable jaw members 320a, 320b moved away from each other, the opening 332 therebetween expands until it is larger than the enlarged head 316 of the tension element 32 at which time the fixed end 33 of the tension element 32 is released from its position between the first and second movable jaw members 320a, 320b.

As with embodiment described above, the jaw drive element 322 is a balloon 338 which may be selectively expanded for engagement with the first and second movable jaw members 320a, 320b in a manner selectively moving the first and second movable jaw members 320a, 320b to their release orientation. While a particular jaw drive element is disclosed above in accordance with a preferred embodiment of the present invention, it is contemplated other drive element mechanisms may be employed without departing from the spirit of the present invention. For example, another jaw drive element 322' is shown with reference to FIGS. 49 and 50. In accordance with this embodiment a shape memory alloy spring 340 is positioned between the movable jaw members 320a, 320b. The spring 340 is linked to a source of electricity 342. Upon application of a voltage across the spring 340, the spring 340 will expand forcing the movable jaw members 320a, 320b apart in a manner moving the jaw mechanism 314 to its release orientation.

In accordance with yet another embodiment shown in FIGS. 51 and 52, the fixed end 33 of the tension element 32 is secured in position for selective release via a fracture mechanism 350. In particular, the fixed end 33 of the tension element 32 is secured to an elongated coupling element 352 extending within a shape memory alloy tube 354, wherein upon the application of a change in temperature, for example, and in accordance with a preferred embodiment, heating, of the shape memory alloy tube 354, the tube 354 will expand in a manner fracturing the elongated coupling element 352 and permitting release of the fixed end 33 of the tension element 32.

The shape memory alloy tube 354 is substantially cylindrical and includes a proximal end 356 and a distal end 358. The elongated coupling element 352 is shaped and dimensioned to extend within the tube 354 between the proximal end 356 and the distal end 358. The tube 354 includes a first opening 360 at the proximal end 356 and a second opening 362 at the distal end 358. The first opening 360 is slightly smaller than the enlarged head 316a of the coupling element 352 and the enlarged head 316a is, therefore, shaped and dimensioned to sit upon the ledge 357 defined by the first opening 360. The second opening 362 of the tube 354 is slightly smaller than the first opening 360. However, the second end of the coupling element 352 also includes an enlarged head 316b which is shaped and dimensioned to sit upon the ledge 359 defined by the second opening 362. As such, the coupling element 352 is held between with first opening 360 of the tube 354 and the second opening 362 of the tube 354 with the enlarged heads 316a, 316b of the coupling element 352 sitting outside of the tube 354. The coupling element 352 is provided with a reduced diameter fracture section 364 located between the enlarged head 316a at the first end of the coupling element 352 and the enlarged head 316b at the second end of the coupling element 352. In accordance with a preferred embodiment of the present invention, the fracture section 364 is located adjacent the second end of the coupling element 352. The fixed end 33 of the tension element 32 is secured to the coupling element 352 at the second end thereof.

With this construction in mind, a heating coil 366 is positioned about the shape memory alloy tube 354 for selective heating of the shape member alloy tube 354 so as to cause expansion thereof. In practice, when it is desired to release the fixed end 33 of the tension element 32, the heating coil 366 is supplied with current causing coil 366 to heat. The heat causes expansion of the shape memory alloy tube 354. The expansion of the shape memory alloy tube 354 results in the application of tension to the coupling element 352. The applied tension stretches the coupling element 352 along its length as enlarged heads 316a and 316b are moved apart, which ultimately results in the fracture thereof at the weakened fracture section 364. Once the fracture section 364 breaks, the second end of the coupling element 352 is free to fall away from the tube 354 along with the fixed end 33 of the tension element 32.

It is also contemplated that cooling could be employed as a mechanism for changing the shape of the elongated tube and the tube may be cooled through the use of a Peltier-cooling element positioned thereabout.

In accordance with a variation of the embodiment described above with reference to FIGS. 51 and 52, the tension element release system is adapted to allow for fluid filling of the gastric band 21 upon the release of the tension element 32 or failure of the tension element 32. In accordance with such an embodiment as shown with reference to FIGS. 53, 54 and 55, the ring 22 is provided with a secondary cavity 370 that is placed in fluid communication with a fluid source 374 once the tension element is released. The secondary cavity 370 extends along the circumference of the ring 22 and is adapted for filling thereof so as to apply pressure via the application of fluid pressure in manner similar to a conventional balloon based gastric band.

The secondary cavity 370 extends about the length of the ring 22 and the tension element 32 extends within (or adjacent to) the secondary cavity 370 such that when the tension element 32 is release as described below fluid access is provided to the secondary cavity 370 for the inflow of fluid necessary to fill the secondary cavity 370 and maintain the application of pressure by the ring 22.

As with the embodiment described above with reference to FIGS. 51 and 52, the fixed end 33 of the tension element 32 is secured in position for selective release via a fracture mechanism. In particular, the fixed end 33 of the tension element 32 is secured to an elongated coupling element 352 extending within a shape memory alloy tube 354, wherein upon heating of the shape memory alloy tube 354, the tube 354 will expand in a manner fracturing the elongated coupling element 352 and permitting release of the fixed end 33 of the tension element 32.

The shape memory alloy tube 354 is substantially cylindrical and includes a proximal end 356 and a distal end 358. The elongated coupling element 352 is shaped and dimensioned to extend within the tube 354 between the proximal end 356 and the distal end 358. The tube 354 includes a first opening 360 at the proximal end 356 and a second opening 362 at the distal end 358. The first opening 360 is slightly smaller than the enlarged head 316a of the coupling element 352 and the enlarged head 316a is, therefore, shaped and dimensioned to sit upon the ledge 357 defined by the first opening 360. The second opening 362 of the tube 354 is slightly smaller than the first opening 360. However, the second end of the coupling element 352 also includes an enlarged head 316b which is shaped and dimensioned to sit upon the ledge 359 defined by the second opening 362. As such, the coupling element 352 is held between the first opening 360 of the tube 354 and the second opening 362 of the tube 354 with the enlarged heads 316a, 316b of the coupling element 352 sitting outside of the tube 354. The coupling element 352 is provided with a reduced diameter fracture section 364 located between the enlarged head 316a at the first end of the coupling member 352 and the enlarged head 316b at the second end of the coupling member 352. In accordance with a preferred embodiment of the present invention, the fracture section 364 is located adjacent the second end of the coupling element 352. The fixed end 33 of the tension element 32 is secured to the coupling element 352 at the second end thereof.

With this construction in mind, a heating coil 366 is positioned about the shape memory alloy tube 354 for selective heating of the shape member alloy tube 354 so as to cause expansion thereof. When it is desired to release the fixed end 33 of the tension element 32, the heating coil 366 is supplied with current causing the coil 366 to heat. The heat causes expansion of the shape memory alloy tube 354. The expansion of the shape memory alloy tube 354 results in the application of tension stretching the coupling element 352 along its length as enlarged heads 316a and 316b are moved apart which will ultimately result in the fracture thereof at the weakened fracture section 364. Once the fracture section 364 breaks, the second end of the coupling element 352 is free to fall away from the tube 354 along with the fixed end 33 of the tension element 32.

However, and in addition to the embodiment described above with reference to FIGS. 51 and 52, the coupling element 352 includes a central port 372 connected to a remote fluid source 374 via port 377. The central port 372 extends from the first end of the coupling member 352 to a stop point 375 adjacent the second end of the coupling member 352, but beyond the fracture section 364. As such, when the fracture section 364 is broken as described above, the fluid is free to flow through the coupling element 352, through the second opening 362 of the tube 354 and into the secondary cavity 370 for filling the secondary cavity 370 and supplying the ring 22 with a pressure source for maintaining the application of pressure against the stomach of the user.

Referring to FIGS. 56A, 56B and 56C, yet another embodiment of implementing a balloon based back-up system in conjunction with the mechanical tension offered by the tension element 32 is disclosed. In accordance with such an embodiment, the fixed end 33 of the tension element 32 is secured to the second end 28 of the ring 22 via a release mechanism 312 allowing selective release of the fixed end 33 of the tension element 32 from the second end 28 of the ring 22 for release of tension being applied by the ring 22. The release mechanism 312 includes a jaw mechanism 314 that selectively engages the fixed end 33 of the tension element 32. The fixed end 33 is provided with a bulbous head 316 that is selectively seated within the jaw mechanism 314 in the manner discussed below in greater detail.

The jaw mechanism 314 includes a fixed jaw member 318 and a movable jaw member 320. A jaw drive element 322 is positioned between the fixed jaw member 318 and the movable jaw member 320. The fixed jaw member 318 is substantially L-shaped and includes a first leg 324 and a second leg 326 oriented perpendicular to each other. Similarly, the movable jaw member 320 is substantially L-shaped and includes a first leg 328 and a second leg 330 oriented perpendicular to each other. The fixed jaw member 318 and the movable jaw member 320 sit facing each other in a mirror like orientation with the first legs 324, 328 of the respective fixed jaw member 318 and the movable jaw member 320 substantially parallel to each other and the second legs 326, 330 of the respective fixed jaw member 318 and the movable jaw member 320 facing each other in an aligned manner. By adopting this orientation, the fixed jaw member 318 and the movable jaw member 320 create a cavity in which the enlarged head 316 of the tension element 32 may sit while the remainder of the tension element 32 extends through the opening 332 formed between the free ends of the respective second legs 326, 330 of the fixed jaw member 318 and movable jaw member 320. As will be appreciated based upon the following disclosure, the movable jaw member 320 is biased toward the fixed jaw member 318 maintaining the free ends forming an opening 332 between the fixed jaw member 318 and movable jaw members 320 in proximity to each other for holding the enlarged head 316 of the tension element 32 until it is desired to release the tension element 32.

When one desires to release the tension element 32, that is, release the enlarged head 316 of the tension element 32 from its position between the fixed jaw member 318 and the movable jaw member 320, the jaw drive element 322 is expanded in a manner pushing the movable jaw member 320 away from the fixed jaw member 318. As the movable jaw member 320 is pushed away from the fixed jaw member 318, that is, as the jaw mechanism 314 is moved from its locked orientation with the fixed jaw member 318 and movable jaw member 320 in close proximity, to its release orientation with the fixed jaw member 318 and movable jaw members 320 moved away from each other, the opening 332 therebetween expands until it is larger than the enlarged head 316 of the tension element 32 at which time the fixed end 33 of the tension element 32 is released from its position between the fixed jaw member 318 and the movable jaw member 320.

In accordance with a preferred embodiment, the jaw drive element 322 is a balloon 338 which may be selectively expanded for engagement with the jaw members 318, 320 in a manner selectively moving the jaw members 318, 320 to their release orientation. As will be appreciated with the following disclosure, the proximal end of the jaw mechanism 314 where the balloon 338 is position is in fluid communication with a fluid source 374 via a port 377 and the balloon 338 is oriented along the jaw mechanism 314 so as to block the flow of fluid until it is desired. When the balloon 338 is fully expanded for release of the fixed end 33 of the tension element 32 as described above, a needle 376 fixed relative to and extending through the movable jaw member 320 contacts the balloon 338 to rupture the balloon 338. With the rupturing of the balloon 338, a passageway 378 is formed between the remote fluid source 374 and the cavity formed between the fixed jaw member 318 and the movable jaw members 320. The remote fluid source 374 is in fluid communication with the passageway 378 and fluid is free to flow through the jaw mechanism 314 and into the secondary cavity 370 (see FIGS. 53, 54 and 55) for filling the secondary cavity 370 and supplying the ring 22 with a pressure source for maintaining the application of pressure against the stomach of the user.

As discussed above with regard to the embodiments in FIGS. 53, 54 and 55, a fluid source 374 is required for implementation of the embodiment. This fluid source 374 is preferably incorporated into the antenna/controller pod 23. In order to ensure fluid pressure is not applied in an undesirable manner, the fluid source 374 is provided with a fail-safe mechanism for releasing fluid pressure in the event of a malfunction of the tension element and when desired by the operator as discussed below with regard to FIGS. 59-67.

In accordance with a variation on this embodiment, the rupture of the balloon 338 could allow for the release of fluid from the ring 22 facilitating release thereof in conjunction with the release of the tension element 32. This would occur where the fluid source (or in this variation, the fluid reservoir) 374 is empty and the fluid is allowed to flow from a prefilled secondary cavity 370 and to the fluid reservoir 374 rather than the fluid flowing form the fluid source 374 to the secondary cavity 370.

In accordance with an alternate embodiment, and with reference to FIGS. 57A, 57B, 58A and 58B, the flow of fluid from the cavity 370 to the fluid source (or reservoir) 374 may be controlled by an electrically sensitive membrane 375 that is destroyed upon the application of the electricity. Once destroyed the passageway between the fluid reservoir 374 and the cavity 370 of the ring 22 is open allowing for the free flow of fluid.

In accordance with the concept of allowing for the release of fluid held in the secondary cavity 370 of the ring 22, the fluid reservoir 374 could be an expandable reservoir that expands or contracts to control the volume of fluid (and as such the pressure applied by the ring). Expansion or contraction of the fluid reservoir 374 is controlled by a shape memory alloy actuator 377 that expands or contracts the fluid reservoir 374 based upon the application of electricity (and ultimately the generation of heat therein) thereto via electrical leads 379. Because the fluid reservoir 374 will be in a vacuum relationship with the cavity 370, controlled expansion and contraction of the fluid reservoir 374 will cause fluid to be drawn from or forced into the cavity 370 of the ring 22.

Figure 59:
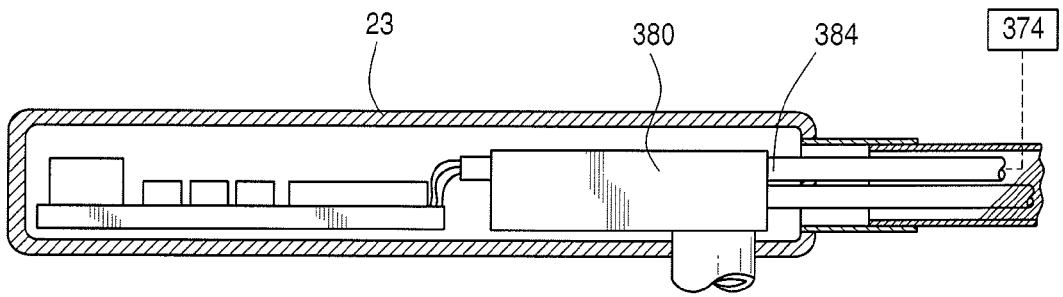
FIGS. 59 to 71 show various embodiments for releasing the tension element.
Figure 60:
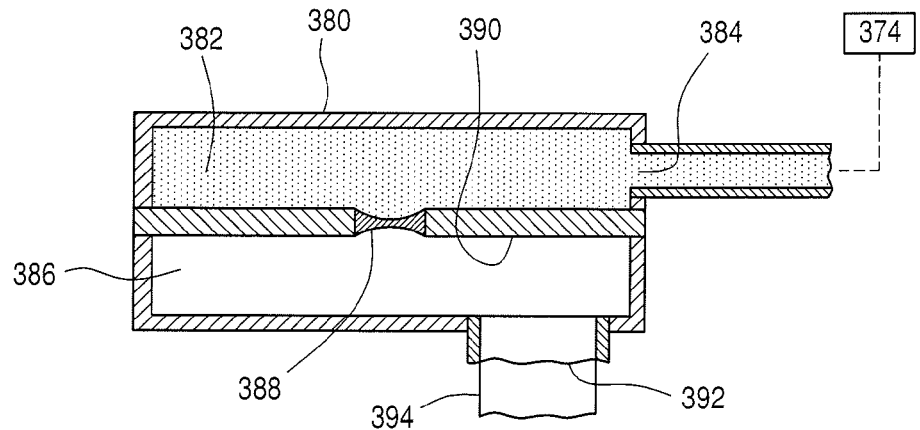
Figure 61:
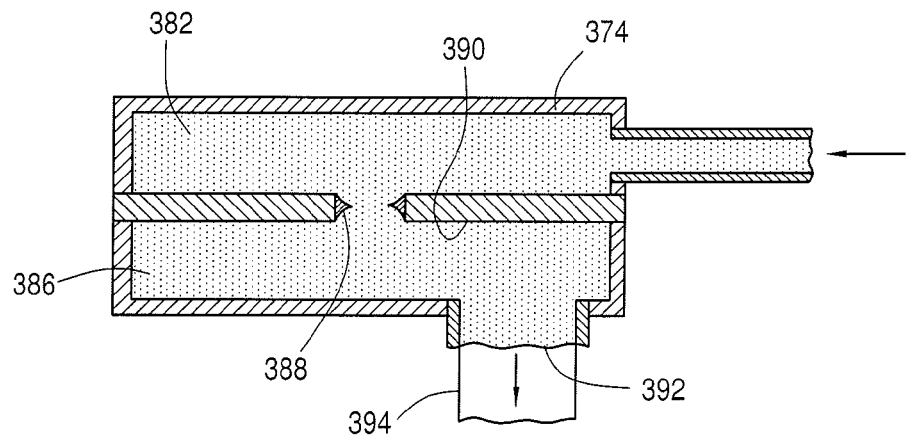

In accordance with an embodiment shown in FIGS. 59, 60 and 61, a fluid source valve 380 is provided along the fluid path to the ring 22. The fluid source valve 380 includes a first chamber 382 in communication with an upstream portion of the fluid source 374 via an inlet 384. The fluid source valve 380 includes a second chamber 386 separated from the first chamber 382 by a valve release membrane 388 formed in a septum 390 separating the first chamber 382 from the second chamber 386. The second chamber 386 includes an outlet 392 leading to a catheter 394 linking the fluid source to the ring 22. When it is desired to allow for the flow of fluid to the ring 22, electrical energy as applied to the valve release membrane 388 destroying the valve release membrane 388 and allowing fluid to freely flow from the inlet 384, through the first chamber 382, the valve release opening 389 and the second chamber 386, and into the outlet 392 for flow though the catheter 394 and into the ring 22.

Figure 62:
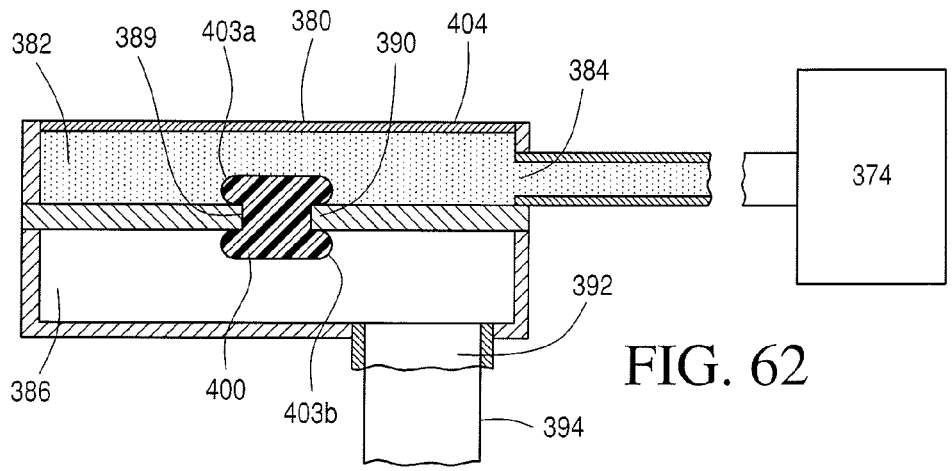
Figure 63:
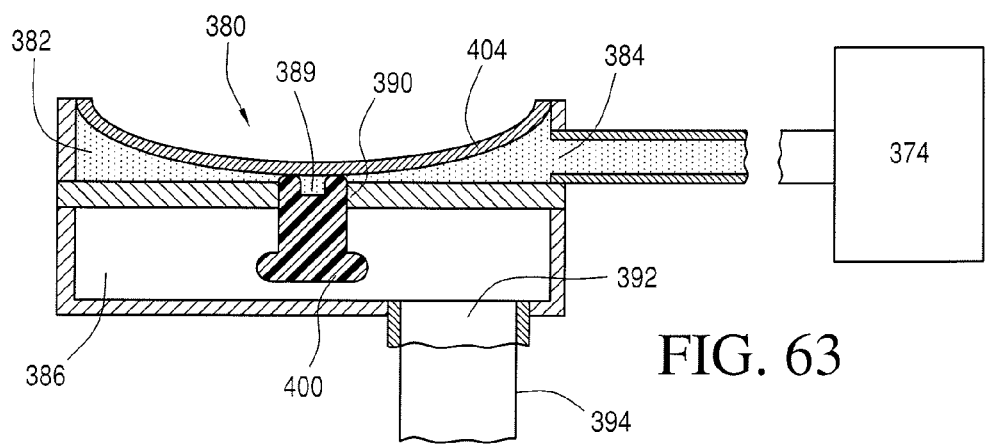
Figure 64:
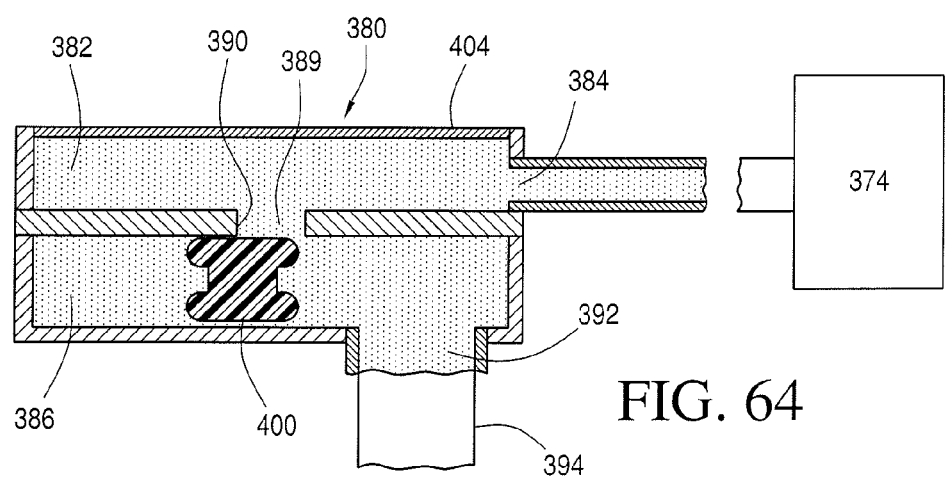

In accordance with an alternate embodiment, and with reference to FIGS. 62, 63 and 64, the fluid source valve 380 includes a first chamber 382 in communication with an upstream portion of the fluid source 374 via an inlet 384. The fluid source valve 380 includes a second chamber 386 separated from the first chamber 382 by a valve release opening 389 formed in a septum 390 separating the first chamber 382 from the second chamber 386 and in which a resilient plug 400 is positioned. The plug 400 is held in position by upper and lower resilient lips 403a and 403b respectively biasing the plug 400 with the valve release opening 389 in septum 390. The second chamber 386 includes an outlet 392 leading to a catheter 394 linking the fluid source 374 to the ring 22. When it is desired to allow for the flow of fluid to the ring 22, an operator may apply pressure through the skin of a patient to access a flexible upper wall 404 of the first chamber 382 and push the plug 400 from its position within the valve release opening 389 and allow fluid to freely flow from the inlet 384, through the first chamber 382, the valve release opening 389 and the second chamber 386, and into the outlet 392 for flow though the catheter 394 and into the ring 22.

Figure 65:
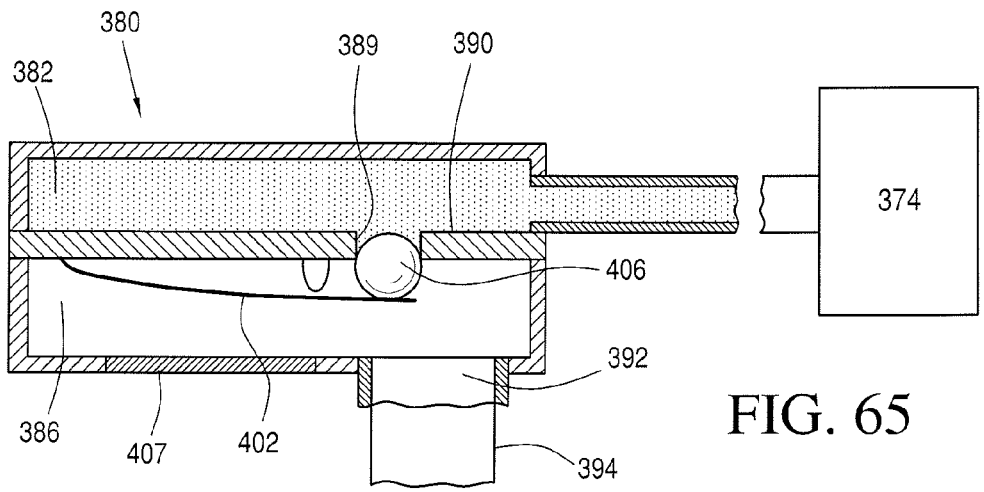
Figure 66:
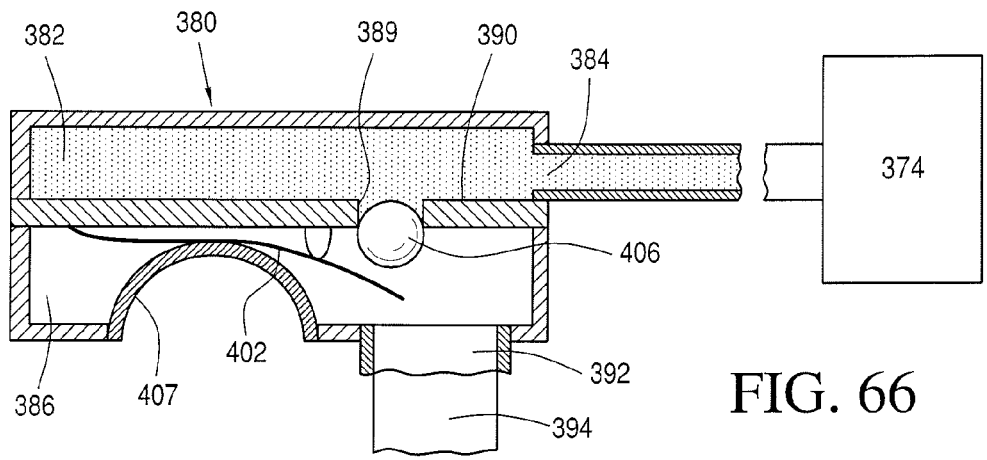
Figure 67:
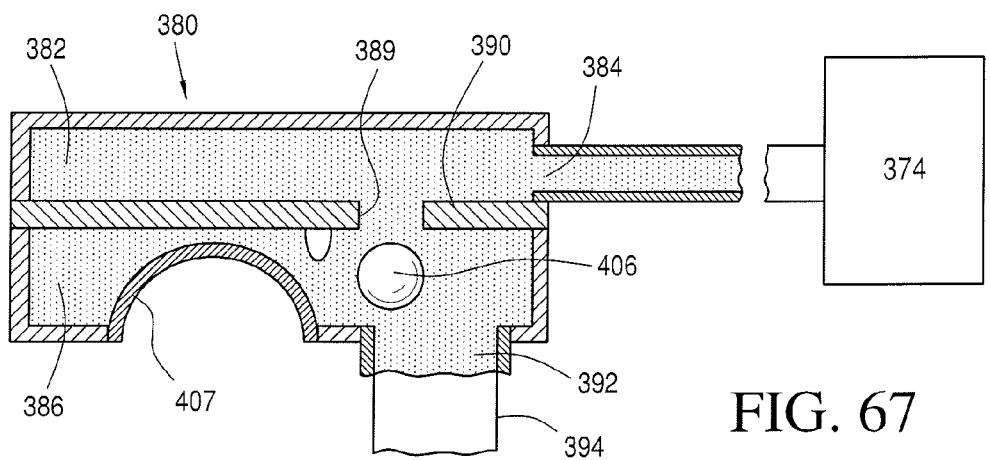

In accordance with yet another alternate embodiment, and with reference to FIGS. 65, 66 and 67, the fluid source valve 380 includes a first chamber 382 in communication with an upstream portion of the fluid source 374 via an inlet 384. The fluid source valve 380 includes a second chamber 386 separated from the first chamber 382 by a valve release opening 389 formed in a wall or septum 390 separating the first chamber 382 from the second chamber 386. A ball 406 is positioned in the second chamber 386 and held in valve release opening 389 by a spring member 402 biasing the ball 406 toward the first chamber 382 and plugging the valve release opening 389. The second chamber 386 includes an outlet 392 leading to a catheter 394 linking the fluid source 374 to the ring 22. When it is desired to allow for the flow of fluid to the ring 22, an operator may apply pressure through the skin of a patient to access a flexible wall 407 of the second chamber 386 and push the spring 402 in a manner releasing the ball 406 from its position within the valve release opening 389 and allowing fluid to freely flow from the inlet 384, through the first chamber 382, the valve release opening 389 and the second chamber 386, and into the outlet 392 for flow though the catheter 394 and into the ring 22.

Figures 68, 69:
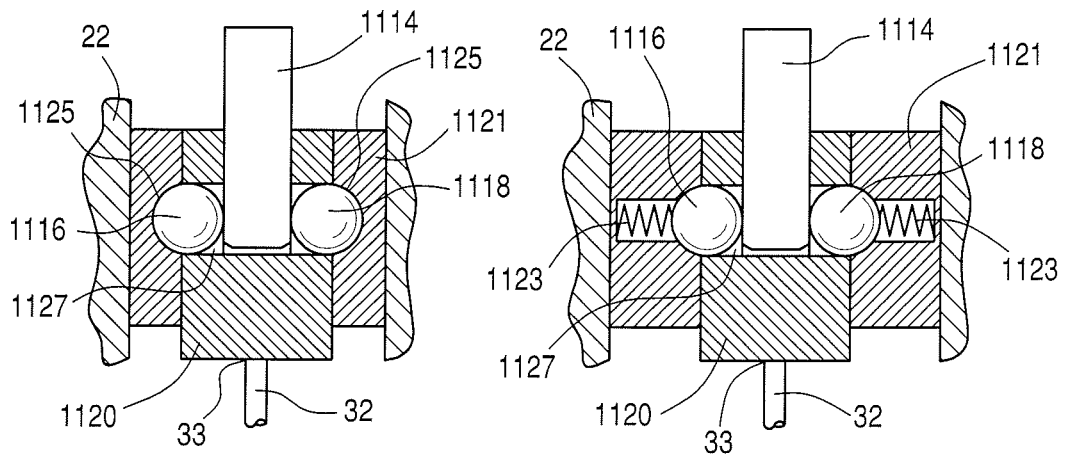

In accordance with alternate embodiments as shown with reference to FIGS. 68 and 69, the fixed end 33 of the tension element 32, that is the portion of the tension element 32 secured to the ring 22 such that action of the drive element 35 causes enlargement or reduction in the effective diameter of the tension element 32, is selectively released via a selective connection mechanism. In accordance with a first embodiment as shown with reference to FIG. 68, actuation of a pin 1114 (whether it be by way of shrinking or removal) allows for movement of first and second detent balls 1116, 1118 permitting release of a connection 1120 linking the fixed end 33 of the tension element 32 to the ring 22.

In particular, the fixed end 33 of the tension element 32 is securely held in position relative to the ring 22 based upon the interference fit created between a retaining disk 1121 including a circumferential recess 1125 formed along the inner wall thereof, the first and second detent balls 1116, 1118, the pin 1114 and the connection 1120. With the various components held as shown in FIGS. 68 and 69, the connection 1120 is fixedly held relative to the retaining disk 1121 which is secured to the ring 22. Once the pin 1114 is removed from its position forcing the detent balls 1116, 1118 into the circumferential recess 1125 and sitting within a central cavity 1127 of the connection 1120, the detent balls 1116, 1118 will move centrally (as a result of the tension applied by the tension element 32) and the fixed end 33 of the tension element will be free to move since the interference fit will have been broken.

Referring to FIG. 69, movement of the detent balls 1116, 1118 is further facilitated by the provision of springs 1123 which encourage the detent balls 1116, 1118 to move centrally upon the removal of the pin 1114.

As discussed above, removal of the pin is achieved either physically or by way of shrinking. Where it is desired to shrink the pin 1114, the pin 1114 is preferably composed of a shape memory alloy adapted to shrink sufficiently upon the application of heat to allow for the movement of the detent balls 1116, 1118 from their positioned within the circumferential recess 1125. In accordance with such and embodiment, a heater mechanism composed of a resistive wire (not shown) is coiled about the shape memory alloy pin 1114. The heating coil uses RF energy transferred to the pin 1114 by means of an inductive coupling realized between the antenna/controller pod 23 and an external RF emitter.

Alternately, it is contemplated the pin may be constructed for simply sliding from its position within the central cavity of the connection. In accordance with another embodiment, the pin may be an electro activated polymer based drive element which shrinks by means of an applied voltage and/or current induced in the pin by means of an inductive coupling.

Figures 70, 71:
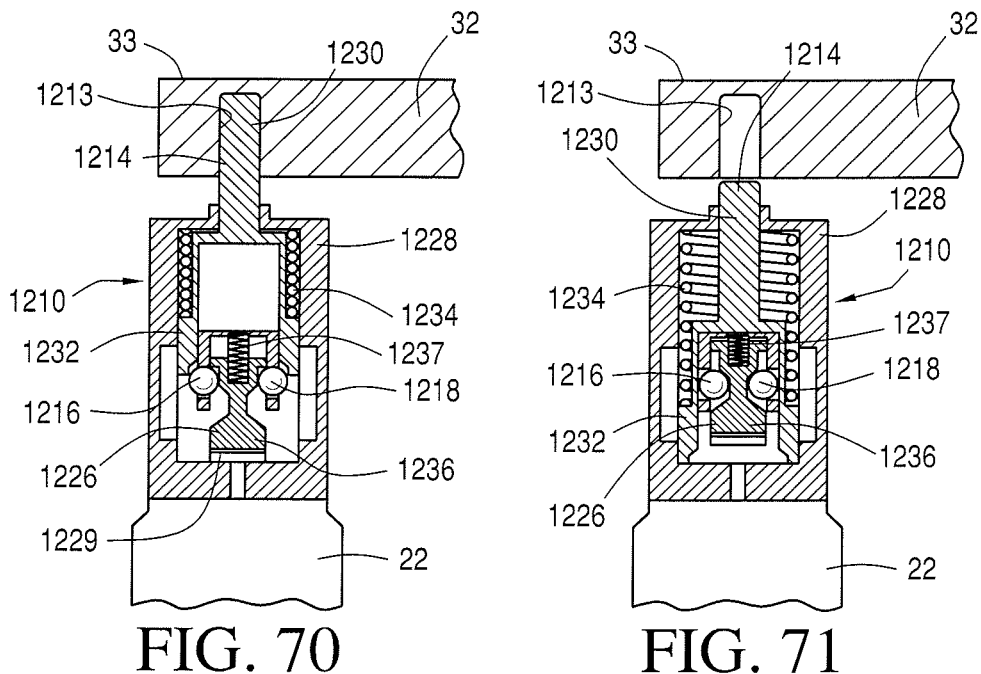

In accordance with a third embodiment as shown with reference to FIGS. 70 and 71, the fixed end 33 of the tension element 32 is selectively secured to the ring 22 by way of a retaining pin 1214. The retaining pin 1214 is fixedly mounted within the ring 22 and engages an aperture 1213 formed in the tension element 32. The retaining pin 1214 is actuated via a mechanically amplified retractable pin assembly 1210. The pin assembly 1210 is secured to the ring 22 and triggered by the motion of a shape memory drive element or a piezoelectric drive element 1226. The mechanically amplified retractable pin assembly 1210 allows the motion necessary for activating the moving retaining pin 1214 to be extremely small (for example, in the hundreds of a micrometer range). The reduced motion is achieved by means of shape memory alloy or piezoelectric based drive elements.

The embodiment includes a housing 1228 secured to the ring 22 and in which a spring biased retaining pin 1214 is mounted for movement between a lock positioned and a release position. The retaining pin 1214 includes an output pin 1230 shaped and dimensioned for seating within an aperture 1213 formed at the end of the tension element 32. The retaining pin 1214 further includes a spring flange 1232 which is acted upon by a drive spring 1234 when the shape memory alloy drive element (such as nitinol) 1226 permits movement thereof. More particularly, controlled movement of the retaining pin 1214 is achieved by creating an interference fit between the retaining pin 1214 and the shape memory alloy drive element 1226 by positioning first and second detent balls 1216, 1218 between the pin 1214 and the drive element 1226. The drive element 1226 includes a drive element body 1236 having an hourglass shape and moves between a first position (see FIG. 70) and second position (see FIG. 71). When the drive element body 1236 is in its first position, the detent balls 1216, 1218 are forced into an interference position preventing movement of the pin 1214 (see FIG. 70). However, when the drive element 1226 is heated it breaks a coupling linking it to the base of the housing 1228 and is free to move upwardly under the bias provided by spring 1237 (see FIG. 71). When the drive element 1226 moves upwardly in this manner, the detent balls 1216, 1218 are free to move into the narrow section of the drive element body 1236 allowing the detent balls 1216, 1218 to move from their position interfering with movement of the pin 1214. Thereafter, the drive spring 1234 moves the pin 1214 to its release position disconnecting the retaining pin 1214, in particular, the output pin 1230, from engagement with the tension element 32.

In summary, the mechanically amplified retractable pin assembly 1210 employs a shape memory alloy drive element 1226 for triggering energy release stored in a loaded compression drive spring 1234. When in the extended position as shown with reference to FIG. 70, the pin 1214 is seen to be loaded by the compression drive spring 1234. The drive spring 1234 remains firmly locked in this position due to the ball lock show in FIG. 70. This is mad possible by the drive element body 1236 which drives outwardly an array of detent balls 1216, 1218. Once actuated however, the spring 1237 drives shape memory alloy drive element drives 1226 upwardly thereby causing the detent balls 1216, 1218 to roll inwardly and allowing the pin 1214 to retract under the force of the drive spring 1234.

Under certain circumstances it may become necessary to release the tension element 32 for emergency removal of the ring 22 from its position around the stomach. As such, and in accordance with a first embodiment as shown with reference to FIGS. 73, 74, 75 and 76, the ring 22, and in particular, the tension element 32, is provided with a release pin 512 that allows for release of the free end 34 of the tension element 32 from its secure attachment position relative to the ring 22. The release pin 512 transversely extends through the ring 22 at a position adjacent to the fixed end 33 of the tension element 32. As a result, when the release pin 512 extends through the ring 22 and is in engagement with the fixed end 33 of the tension element 32, the tension element 32 is securely held in position for contraction and expansion of the ring 22 as discussed herein. However, when the release pin 512 is pulled from its position along the ring 22 and out of engagement with the fixed end 33 of the tension element 32, the fixed end 33 of the tension element 32 is released for free movement within the ring 22 (see FIGS. 75 and 76). As such, the tension created between the free end 34 of the tension element 32 and the fixed end 33 of the tension element 32, which ultimately allows for a reduction in the effective size of the ring 22, is released and the ring 22 is allowed to return to its unbiased large diameter configuration. Once in this large diameter configuration, the ring 22 may be readily removed from its position about the stomach of the patient.

Figure 77:
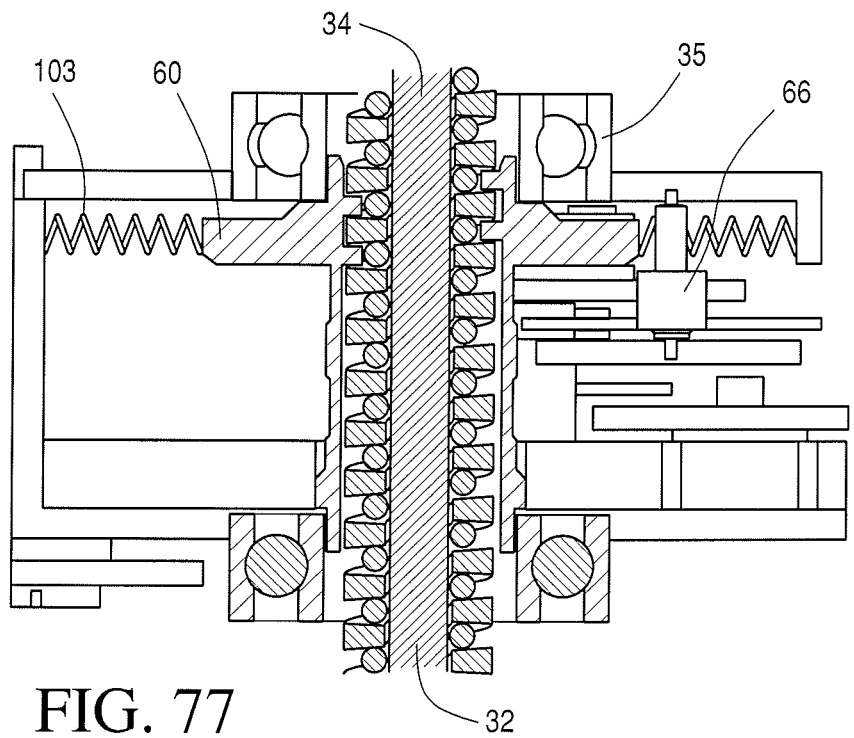
Figure 78:
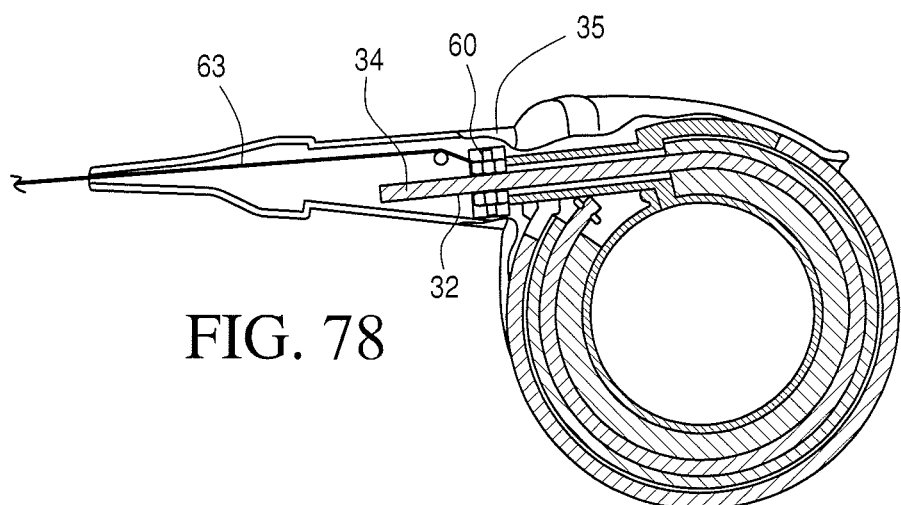

In accordance with an alternate embodiment, and with reference to FIGS. 77 and 78, the nut 60 of the drive element 35 is replaced with a slip nut 60 that allows for selective release of the free end 34 of the tension element 32 from its position within the drive element 35. More particularly, the slip nut 60 allows the threaded free end 34 of the tension element 32 to slip past the drive nut 60 when necessary to allow the band restriction to be released if the motor 66 fails to operate. The slip nut 60 has the advantage of being either spring 103 loaded to release at a known pull force of the threaded screw (see FIG. 77) or the slip nut 60 could be normally closed and a linkage 63 is provided that could be activated at the antenna/controller pod 23 (see FIG. 78).

Figure 79:
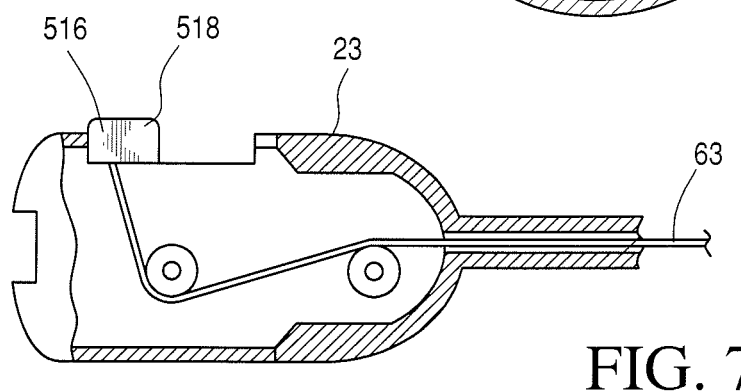

Referring now to the embodiment presented with reference to FIG. 77, the nut 60 is spring-loaded for release of the threaded free end 34 of the tension element 32 at a known pull force. More specifically, a slip nut 60 is a nut formed in multiple pieces which are held together via springs or other means. FIG. 77 shows the slip nut 60 spring loaded to open at a desired pull force on the threaded free end 34 of the tension element 32. Springs by design provide force greater than the forces generated under normal conditions when food is swallowed, but if the band is stretched circumferentially by using an esophageal dilator the force overcomes the springs and the threaded free end 34 slips through the nut 60 relaxing the restriction. FIG. 78 shows the slip nut 60 wherein multiple pieces are held together with a linkage 63 that terminates in the antenna/controller pod 23 for disengaging the nut 60 from the threaded free end 34. The termination of the linkage 63 could be activated by a simple toggle 516. FIG. 79 shows this toggle 516 and also provides a sketch of the linkage termination. The simple push pull design allows a doctor to make an incision in the skin to access the toggle 516. A further improvement would be to provide a button, or some means of activating the linkage without cutting the skin to access the release mechanism. In implementing such an embodiment, it is contemplated the button would be spring loaded such that upon access to the button with, for example, a hypodermic needle, pushing the button releases the spring and thereby activates the linkage release mechanism.

With reference to the embodiment shown in FIG. 79, the split nut 60 is activated for release through actuation of a button 518 at the antenna/controller pod 23. This embodiment overcomes the need for access into the patient's abdomen and could be activated without the need for incisions. If an emergency situation presented itself the patient could have a small incision made above the antenna/controller pod 23 on the sternum and the fail-safe linkage 63 could be activated directly. This would allow the device to be replaced at a later date, or troubleshoot the device and possibly replace the antenna/controller pod 23 in a subcutaneous procedure without needing to remove the entire implant.

Another embodiment for the release of the threaded free end 34 of the tension element 32 is shown with reference to FIGS. 80 and 81. This embodiment includes a nut 60 construction that improves upon the nut's ability to engage and disengage simply. The use of an elliptical nut 60 that pivots on an axis perpendicular to the axis of the threaded free end 34 of the tension element 32 allows for easy engagement and disengagement of the threaded free end 34 of the tension element 32. This embodiment also utilizes a linkage 63 from the antenna/controller pod 23 and a switch/toggle 516 to pull the threaded free end 34 of the tension element 32 for disengagement. The nut 60 is spring loaded via spring 517 to provide positive displacement for the nut 60 to engage the threads of the threaded free end 34 of the tension element 32 when the fail-safe is not engaged. FIG. 80 shows the elliptical nut 60 in the engaged position and FIG. 81 shows the elliptical nut 60 in the fail-safe disengaged position. In FIG. 81, the linkage wire 63 that is connected to the antenna/controller pod 23 is moved to a position for fail-safe release of the threaded free end 34 of the tension element 32, which causes the elliptical nut 60 to move and release from the threaded free end 34.

In accordance with yet another embodiment as shown with reference to FIG. 82, an antenna/controller pod 23 that utilizes a magnetic deactivation function is disclosed. This requires a magnetic coil or magnetic emitting antenna 522 to be placed over the antenna 83 of the antenna/controller pod 23 and the oscillating electromagnetic field deactivates the device electronically. That is, the magnetic field induces a reverse polarity in the antenna/controller pod 23, which in turn reverses the voltage sent to the motor 66. This back drives the motor 66 without the use of the control pod in case of an electrical failure in the controller pod, but the motor was still operable. The controller pod would have a secondary circuit to allow the oscillating magnetic field coupling to generate a sufficient amount of power to drive the motor in a given direction. In this case, the desire would be to rotate the motor such that the pressure around the tissue is relieved. MRI sensitivity should not be an issue as an MRI generates a very high intensity permanent field (which will not generate a voltage in a magnetic coil or magnetic emitting antenna) and a very low intensity oscillating electromagnetic field (which will not generate a significant voltage since it is low intensity). The technical challenges of providing enough energy to the implant to reverse the voltage to the motor 66 is also challenged if the wires from the antenna/controller pod 23 becomes detached from the motor 66 or antenna/controller pod 23 itself. FIG. 82 shows the magnet over the antenna 83 providing energy to reverse the motor 66.

Referring now to other embodiments for release of the threaded free end 34 of the tension element 32. In FIGS. 83, 84 and 85, the drive nut 60 has a split construction and is composed of four distinct elements 560a, 560b, 560c, 560d forming a central aperture 524 through which the threaded free end 34 of the tension element 32 passes for threaded driving as discussed above. A driving gear 526 is secured to the outer surface 528 of the nut 60 and drives it in a circular configuration as described above. However, the drive nut 60 is resilient and is adapted for biasing such that the threads 530 formed along the inner surface of the nut 60 disengage from threads 532 formed along the external surface 534 of the free end 34 of the tension element 32. In particular, each of the nut elements 560a-d making up the nut 60 has a C-shaped cross sectional profile as shown with reference to FIGS. 83 and 85. The C-shaped profile includes a first plate member 536 and a second plate member 538 connected by a central connecting member 540. The central connecting member 540 also functions as a part of the inner surface 542 of the aperture 524 through which the fixed end 33 of the tension element 32 passes. The connecting member 540 is provided with a weakened portion 544. As such, when pressure is applied to the first plate member 536 in a direction toward the second plate member 538, the first plate member 536 will then move downwardly toward the second plate member 538 causing the connecting member 540 to move from its normal orientation relative to the second plate member 538 and form an acute angular relationship with respect to the second plate member 538. By applying pressure to all of the first plate members 536 of the respective nut elements 560a-d simultaneously, the inner threads 530 along the nut 60 are moved away from the free end 34 of the tension element 32 thereby providing for release and free movement of the tension element 32 relative to the nut 60.

In accordance with a preferred embodiment, pressure is applied to the first plate member 536 of the respective nut elements 560a-d through the utilization of a plurality of pressure application plates 546. Each of these pressure application plates 546 includes a resilient balloon 548 which may be expanded upon application of fluid pressure thereto. Since the pressure application plates 546 are formed so as to be positioned directly adjacent the first plate members 536 of the respective nut elements 560a-d, when a balloon 548 is expanded, the balloon 548 will expand into contact with the first plate member 536 of the nut element 560a-d pushing it toward the second plate member 538 of the nut element 560a-d and causing the connecting member 540 to angle away from the free end 34 of the tension element 32 as described above.

Figure 86:
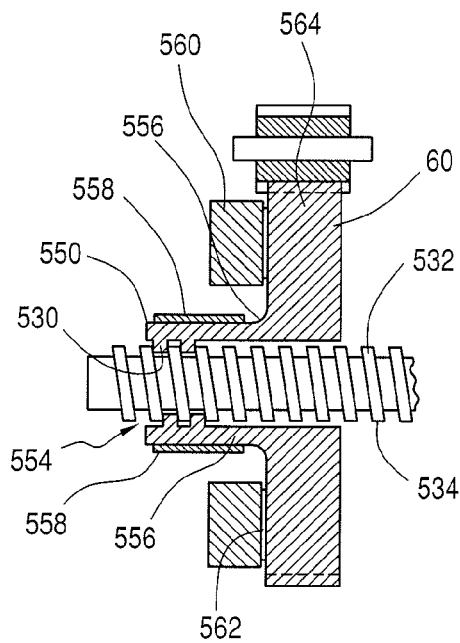
Figure 87:
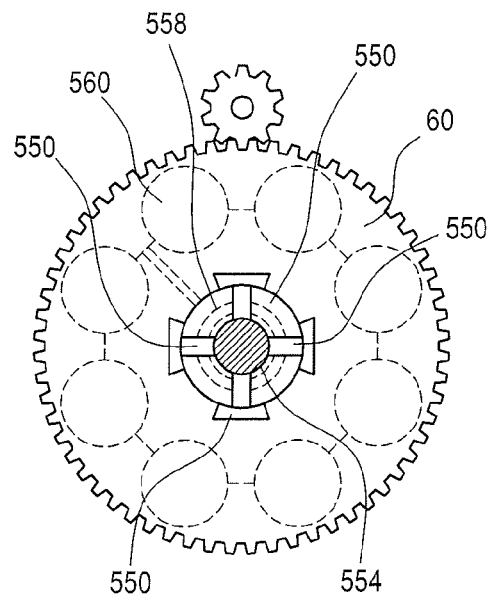
Figure 88:
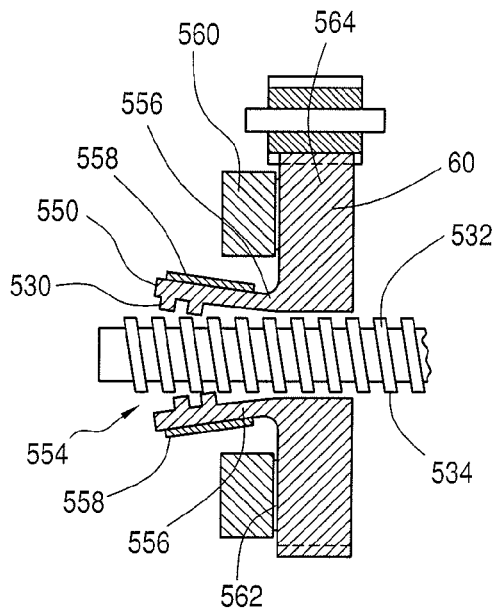

In accordance with yet another embodiment of the present invention, and with reference to FIGS. 86, 87 and 88, the nut 60 is provided with flanges 550 upon which the internal threading 530 of the aperture 554 is positioned. These flanges 550 are secured to the nut 60 for controlled movement relative thereto. In particular, and with reference to FIG. 86, when the nut 60 and in particular, the flanges 550, are intended for engagement with threading 530 formed along the outer surface 534 at the free end 34 of the tension element 32, the flanges 550 are oriented substantially normal to the plane in which the nut 60 lies. As such, and when in this configuration, the internal threading 552 along the flanges 550 engages the threading 532 at the free end 34 of the tension element 32 and rotation of the nut 60 causes the threaded free end 34 to be moved relative to the nut 60 for drawing the tension element 32 through the nut 60.

However, the rear outer surface 556 of each flange 550 is provided with a resistive heating element 558 that is connected to an electrical coil 560 secured along the back surface 562 of the outer periphery 564 of the nut 60. As such, when electricity is applied to the coils 560, the resistive heaters 558 are actuated heating the flanges 550. The flanges 550 are constructed such that when they are heated, or otherwise encounter a change in temperature, they will bend away from the free end 34 of the tension element 32 forming an acute angle with the plane in which the nut 60 lies (see FIG. 88). Once in this configuration, and with reference to FIG. 88, the free end 34 of the tension element 32 is free to move relative to the nut 60 for free movement of the tension element 32 relative thereto.

Referring now to FIGS. 89, 90 and 91, yet another embodiment for release of the tension element 32 is disclosed. In accordance with this embodiment, the fixed end 33 of the tension element 32 is secured to a two-bar linkage 566. When the tension element 32 is intended for utilization in constriction of the stomach, the two-bar linkage 566 is folded so that the links 568, 570 nearly overlap (see FIG. 89). When the band 21 needs to be released in an emergency, the two-bar linkage 566 is actuated via a pull lever 567 (see FIG. 91) so as to pull the two bar linkage 566 from its folded configuration and into an extended configuration (see FIG. 90). With the two bar linkage 566 in an extended configuration, the effective length of the tension element 32 is increased providing additional diameter within the ring 22 and allowing the gastric band 21 to be moved from its position along the stomach.

Figure 92:
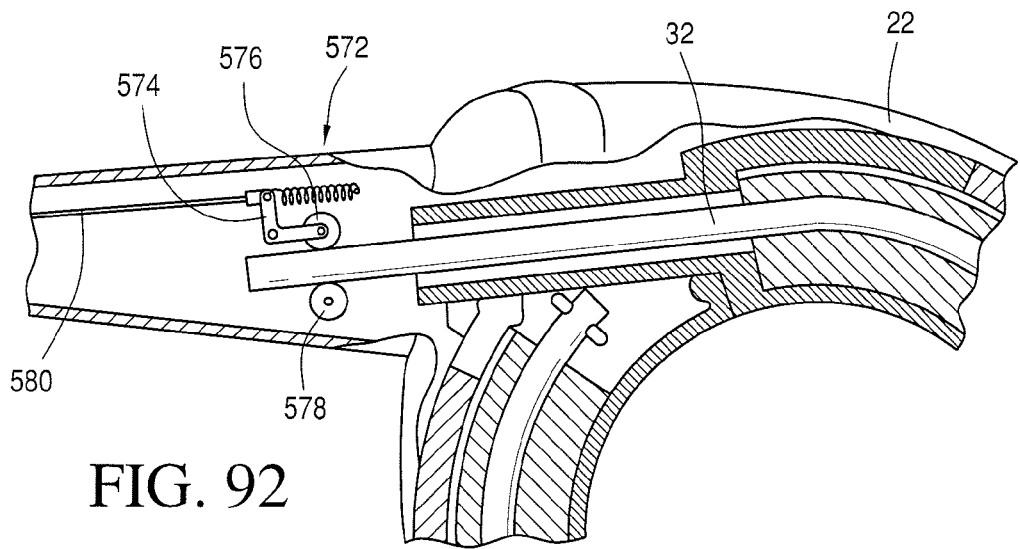
Figure 93:
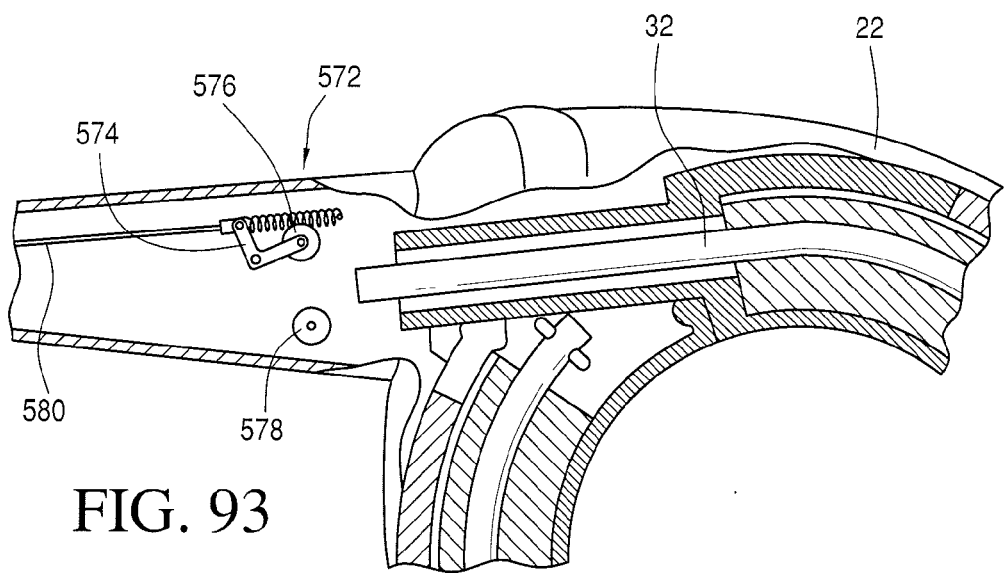
Figure 94:
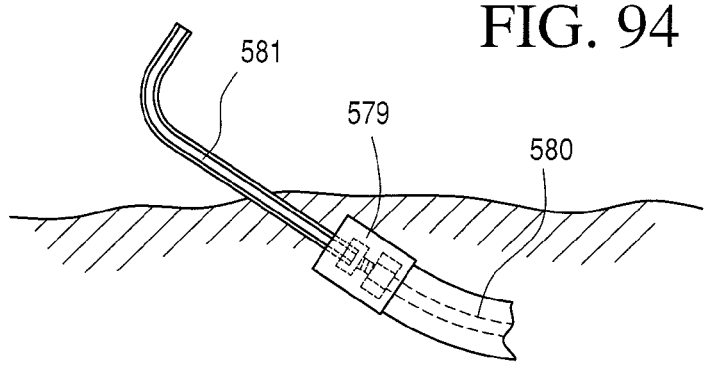

Referring now to FIGS. 92, 93 and 94, a compression, friction drive assembly 572 is utilized for pulling the tension element 32. The friction drive assembly 572, however, includes a release member 574 which moves the opposed rollers 576, 578 of the friction drive assembly 572 apart from each other allowing for free movement of the tension element 32 within the ring 22. Controlled movement of the release member 574 is achieved via the utilization of a pull wire 580 which, when acted upon, forces the rollers 576, 578 of the friction drive assembly 572 apart against the bias of the spring 577 that biases them toward the tension element 32, permitting free movement of the tension element 32. In accordance with a preferred embodiment, and with reference to FIG. 94, movement of the wire 580 is controlled by a screw mechanism 579 that may be selectively acted upon with, for example, a hex wrench 581, to loosen or tighten the wire 580.

Figure 95:
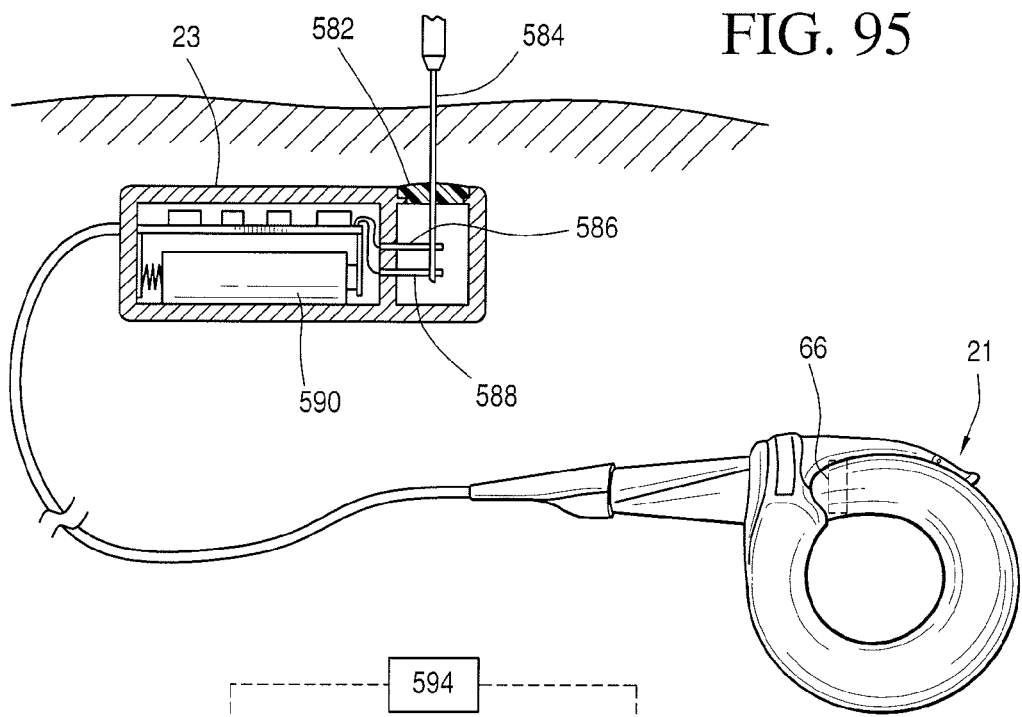
FIGS. 95 and 96 show embodiments for accessing the electronic controls of the antenna/controller pod for controlling operation of the ring in accordance with the present invention.

In accordance with yet another embodiment of the present invention, and with reference to FIG. 95, the antenna/controller pod 23 is provided with an access port 582 providing a medical practitioner with access to the control electronics of the antenna/controller pod 23 for control thereof in the event of failure. In accordance with such an embodiment a needle 584 would access the access port 582 so as to act like a contact that would either flex contacts 586, 588 or just bridge the contacts 586, 588 to run the motor 66 in the direction to open the gastric band 21 to a maximum diameter thereby relieving any pressure applied by the gastric band 21. For such a method to work, the antenna/controller pod 23 is provided with a battery 590 having a shelf life, for example, of ten or more years, and with enough power to store energy to power the gastric band 21 for a reasonable length of time. Since there is a battery 590 provided with the antenna/controller pod 23, telemetry could be used via wireless technology such as Bluetooth and could allow a patient to self adjust the gastric band 21 without the need for a power module. It is further contemplated rechargeable batteries may be employed and recharging may be achieved on a regular basis via a power unit at a doctor's office or while the patient is sleeping so that more benefits could come from the ability to non-invasively adjust the band.

Figure 96:
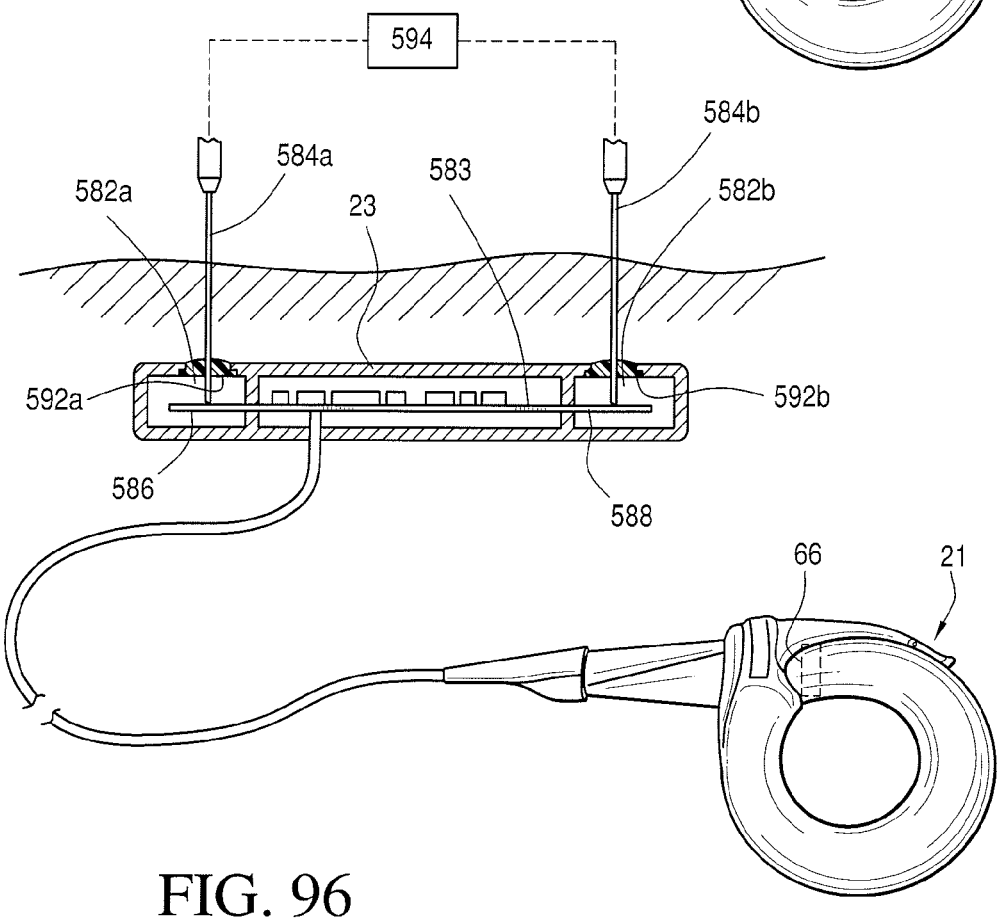

In accordance with a variation on the embodiment disclosed with reference to FIG. 96 the antenna/controller pod 23 is provided with dual access ports 582a, 582b linked to the printed circuit band 583. As such, and when emergency situations arise under circumstances where the antenna/controller pod 23 does not have sufficient power, the two needles 584a, 584b applied to the first and second ports 582a, 582b of the antenna/controller pod 23 are charged to supply power to the antenna/controller pod 23. In accordance with this embodiment, the first and second ports 582a, 582b are provided with self-healing elastomeric targets 592a, 592b for needle placement.

As briefly discussed above, the needles 584a, 584b are charged. As such, the needles 584a, 584b are connected to a power source 594 that is readily available in a hospital. When the needles 584a, 584b are contacting the conductors 586, 588 in the printed circuit board 583 of the antenna/controller pod 23, the motor 66 will run in the opening direction and the diameter of the gastric band 21 is increased to eliminate any pressure applied by the gastric band 21.

The gastric band 21 would then return to normal operating conditions when appropriate and can be used as designed in accordance with the principles of the present invention. The present embodiment would also function for its intended purpose in the event the printed circuit board failed provided the emergency electrical path employed in accordance with this embodiment is not part of the operating circuitry of the printed circuit board.

Ring Closure System

Figures 97A, 97B:
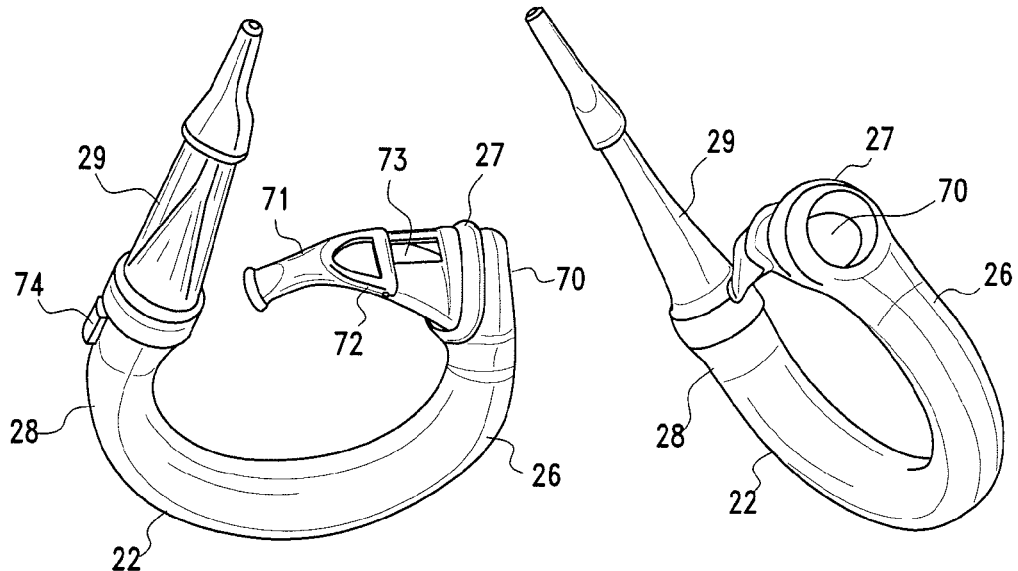
FIGS. 97A and 97B are perspective views illustrating the clip used to close the ring into a loop.

With respect to FIGS. 97A and 97B, a preferred embodiment of the clip 27 for securing the gastric band 21 in the closed position is described. The clip 27 on the first end 26 of the ring 22 includes an aperture 70, a tab 71 having a hinge 72 and a slot 73. The aperture 70 is dimensioned to accept the second end 28 therethrough, while the slot 73 is dimensioned to accept the flange 74 disposed on the second end 28.

To close the ring 22, the clip 27 is grasped by the tab 71 and the tag 25 of the antenna/controller pod 23 (see FIG. 1) is inserted through the aperture 70. The clip 27 is then pulled toward the second end 28 so that the housing 29 passes through the aperture 70 while the housing 29 is grasped with atraumatic forceps; the conical shape of the housing 29 facilitates this action. Force is applied to the tab 71 until the slot 73 captures the flange 74, thereby securing the ring 22 in the closed position. The physician may subsequently choose to disengage the slot 73 from the flange 74 by manipulating the tab 71 using laparoscopic forceps, for example, to reposition the ring 22. Advantageously, however, forces inadvertently applied to the tab 71 in an opposite direction will cause the tab 71 to buckle at the hinge 72, but will not cause the flange 74 to exit the slot 73. Accordingly, the hinge 72 of the tab 71 prevents accidental opening of the clip 27 when the tab 71 is subjected to forces that cause the tab 71 to fold backwards away from the housing 29, such as may arise due to movement of the patient, the organ, of or bolus of fluid passing through the organ.

Figure 98:
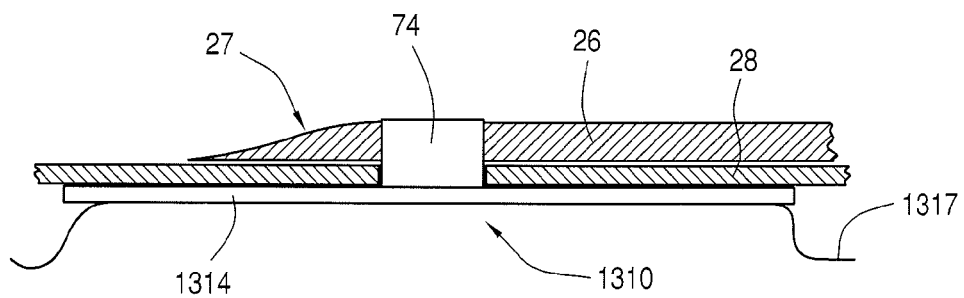
FIGS. 98 and 99 show a release mechanism for a clip of the ring in accordance with an alternate embodiment of the present invention.
Figure 99:
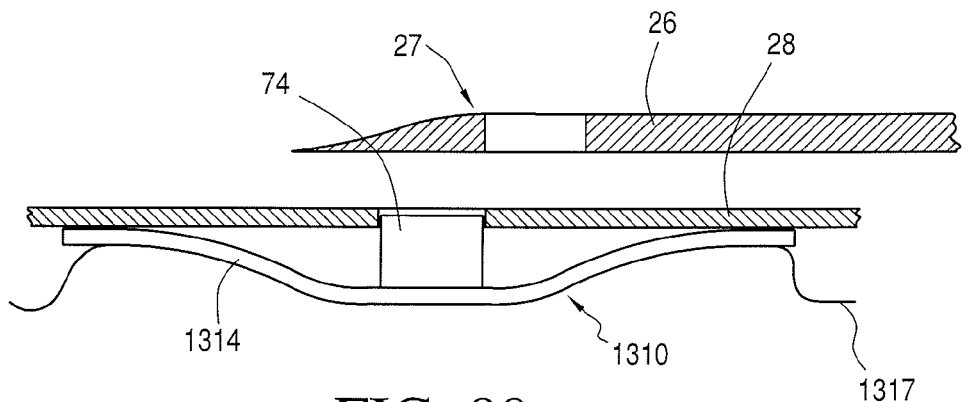

As discussed above, it may at times become necessary to release the pressure applied by the gastric band 21. With this in mind, and in accordance with yet another embodiment as shown with reference to FIGS. 98 and 99, the first and second ends 26, 28 of the gastric band 21 are provided with a mechanism allowing release from their locked positions via a remote latch unlock mechanism 1310. In particular, the clip 27 holding the first and second ends 26, 28 of the gastric band 21 together is released via a variety of electromechanical mechanisms. For example, actuation of an emergency release button (not shown) on the antenna/controller pod 23 will cause release of the clip 27. When the button triggers a communication, a voltage is applied on a flange actuator 1314 by the electronics of the antenna/controller pod 23. The temperature of the actuator 1314 then increases and this triggers movement of the flange 74 toward the inside of the gastric band 21 until the band clip 27 is released (for example, via a shape memory alloy actuator or a bimetallic actuator). Such an embodiment, might allow for treatment without the patient visiting the hospital or other treatment center. The unit might be activated via modem or Internet connection by the surgeon.

Antenna/Controller Pod

With respect to FIGS. 100 and 101, the antenna/controller pod 23 of the present banding system is described. The antenna/controller pod 23 is disposed at the distal end of the antenna cable 24 and includes the removable tag 25 and holes 75. The tag 25 comprises a grip structure that facilitates manipulation and placement of the antenna/controller pod 23 during implantation; after which the tag 25 is removed using a scissors cut. The tag 25 also includes hole 25b that allows the use of a suture thread to assist in passing the antenna/controller pod 23 behind the stomach. The holes 75 also are dimensioned to be compatible with standard suture needles from size 1-0 to 7-0 to permit the antenna/controller pod 23 to be sutured to the patient's sternum, thereby ensuring that the antenna/controller pod 23 remains accessible to the external antenna 14 and cannot migrate from a desired implantation site.

As shown in FIG. 101, the antenna/controller pod 23 encloses a printed circuit board 76 that carries the antenna 83 and microcontroller circuitry of the gastric band 21. The antenna 83 receives energy and commands from the external control 10 (see FIG. 1), and supplies those signals to the microcontroller, which in turn powers the motor 66 of the drive element 35. The circuitry of the antenna/controller pod 23 uses the energy received from the incoming signal to power the circuit, interprets the commands received from the external control 10, and supplies appropriate signals to the motor 66 of the drive element 35. The circuit also retrieves information regarding operation of the motor 66 of the drive element 35 and relays that information to the external control 10 via the antenna 83. The circuit board preferably is covered with a water-resistant polymeric covering, e.g., Parylene, to permit use in the high (up to 100%) humidity environment encountered in the body.

The antenna/controller pod 23 includes a mechanical closure system that is augmented by silicone glue so that the pod is fluid tight. This silicone glue also is used to protect soldered wires 79 from humidity. The antenna/controller pod 23 preferably is small, e.g., 16 mm×33 mm×4 mm, to ensure compatibility with a standard 18 mm trocar and so as to be compatible with placement on the sternum. The antenna/controller pod 23 preferably has a smooth, atraumatic shape to avoid tissue damage, has good mechanical strength to withstand handling with surgical graspers and to prevent mechanical deformation to the printed circuit board, and has good electromagnetic permeability to allow efficient energy transmission through the antenna/controller pod 23. The antenna/controller pod 23 preferably has a relatively thin planar configuration to avoid rotation of the antenna/controller pod 23 when placed under the skin, and may include holes that permit the antenna/controller pod 23 to be sutured in position.

With respect to FIG. 102, the antenna cable 24 is shown in cross-section. The antenna cable 24 preferably is a coaxial shielded cable encapsulated in a silicone tube 77 to provide biocompatibility. The tube 77 is selected to provide leak-proof encapsulation, with sufficient strength to permit the antenna cable 24 to be manipulated with atraumatic graspers. The braided shield 78 of the antenna cable 24 prevents longitudinal deformation of the antenna cable 24, and surrounds five helically wound insulated wires 79. Four of the wires 79 are used to supply power to the micromotor of the drive element 35; the remaining wire and braided shield 78 are used to supply a signal from the reference position switch to the controller.

As discussed above with respect to FIG. 1, the gastric band 21 according to the present invention provides an integrated system for regulating food ingestion in the stomach of a patient, wherein variation of the diameter of the ring 22 may be adjusted without any invasive surgical intervention. To accomplish this, the drive element 35 is linked to the subcutaneous antenna/controller pod 23 to receive a radio frequency control and power signal. In accordance with a preferred embodiment, the motor 66 of the drive element 35 has no internal energy supply, but rather is powered by the receiving circuit of the antenna 83 through a rechargeable energy storage device, such as a capacitor. In particular, the receiving circuit converts radio frequency waves received from the external control 10 via the antenna 14 into a motor control and power signal. In accordance with an alternate embodiment, it is contemplated the drive element may be driven via an implantable rechargeable battery.

Power and Control Circuitry

Figure 105:
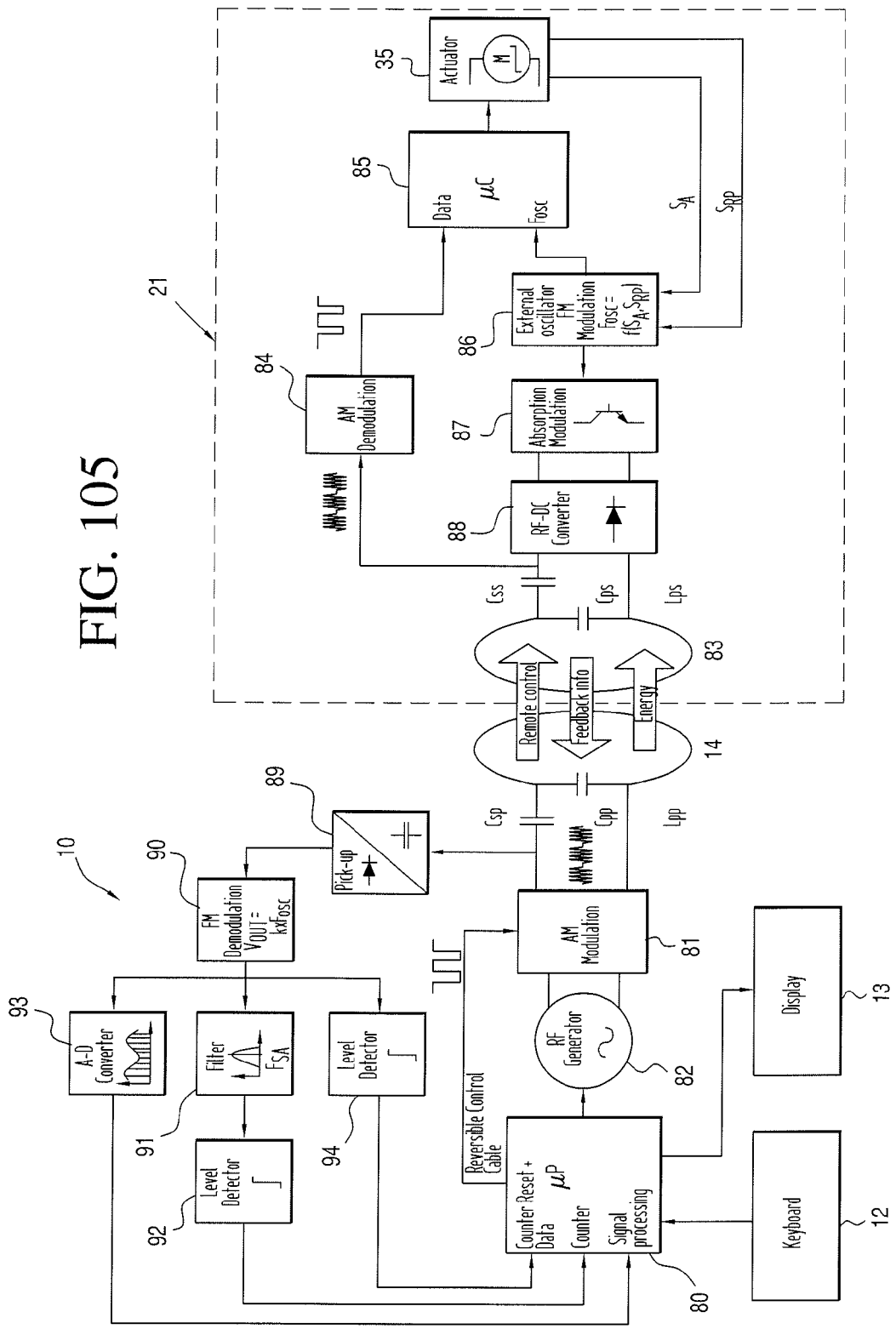
FIG. 105 is a schematic view of the telemetric power and control circuitry of the present invention.

Referring to FIG. 105, a preferred embodiment of the circuitry employed in the external control 10 and the gastric band 21 of the present invention is described, based on the principle of passive telemetry by FM-AM absorption modulation. The external control 10 is shown on the left hand side of FIG. 105, and includes a microprocessor 80 coupled to the control panel 12 and the display screen 13 (see FIG. 1). The external control 10 produces a signal comprising one or more data bytes to be transmitted to the implantable antenna/controller pod 23 and the drive element 35.

The external control 10 includes a modulator 81 for amplitude modulation of the RF wave from the RF generator 82, which signal is emitted by the external antenna 14. The emitted wave is received by the antenna 83 in the antenna/controller pod 23, where the AM demodulator 84 extracts the data bytes from the envelope of received RF signal. The data bytes then are decoded and written into an EEPROM of the microcontroller 85. A special code is used that allows easy decoding of the data by the microcontroller 85, but also provides maximal security against communication failure.

An external oscillator 86, which is a voltage controlled oscillator (VCO), provides a clock signal to the microcontroller 85. The external oscillator 86 may consist of, for example, a relaxation oscillator comprising an external resistor-capacitor network connected to a discharging logic circuitry already implemented in the microcontroller or a crystal oscillator comprising a resonant circuit with a crystal, capacitors and logic circuits. The former solution requires only two additional components, is suitable when the stability of the frequency is not critical, and has low current consumption; the latter solution provides a more stable frequency, but requires a greater number of additional components and consumes more power. The external oscillator 86 preferably comprises the external RC network, due to its simplicity.

The microcontroller 85 interprets the received instructions and produces an output that drives the motor 66 of the drive element 35. As discussed above, the drive element 35 comprises a bi-directional stepper motor 66 that drives the nut 60 through a series of reducing gears. Preferably, the two coils of the stepper motor 66 of the drive element 35 are directly connected to the microcontroller 85, which receives the working instructions from the demodulator 84, interprets them and provides the voltage sequences to the motor coils. When the supply of voltage pulses to the stepper motor 66 stops, the gears are designed to remain stationary, even if a reverse torque or force is applied to the nut 60 by the tension element 32.

As also described above, use of a stepper motor 66 in drive element 35 makes it is possible to obtain positional information on the nut 60 and the tension element 32 without the use of sensors or encoders, because the displacement of the tension element 32 is proportional to the number of pulses supplied to the stepper motor coils. Two signals are employed to ensure precise control, reference position signal $S_{RP}$, generated by the reference position switch of FIG. 13, and the drive element signal $S_A$.

According to one preferred embodiment, signal $S_A$ is the voltage signal taken at one of the outputs of the microcontroller 85 that is connected to the motor coils of the drive element 35. Alternatively, signal $S_A$ could be derived from the current applied to a motor coil instead of the voltage, or may be an induced voltage on a secondary coil wrapped around one of the motor coils of the drive element 35. In either case, signal $S_A$ is a pulsating signal that contains information on the number of steps turned by the rotor and further indicates whether blockage of the mechanism has occurred. Specifically, if the rotor of the stepper motor fails to turn, the magnetic circuit is disturbed, and by induction, affects signal $S_A$, e.g., by altering the shape of the signal. This disturbance can be detected in the external control, as described below.

Signals $S_A$ and $S_{RP}$ are converted into frequencies using the external oscillator 86, so that the voltage level of signal $S_A$ applied to the external oscillator 86 causes the oscillator to vary its frequency $F_{osc}$ proportionally to the signal $S_A$. Thus, $F_{osc}$ contains all the information of signal $S_A$. When the crimped cap 45 and the tension element 32 are in the reference position (that is, the ring 22 is fully open), the reference position switch produces reference position signal $S_{RP}$. Signal $S_{RP}$ is used to induce a constant shift of the frequency $F_{osc}$, which shift is easily distinguishable from the variations due to signal $S_A$.

If the external oscillator 86 is a relaxation oscillator, as described above, signals $S_A$ and $S_{RP}$ modify the charging current of the external resistor capacitor network. In this case, the relaxation oscillator preferably comprises an external resistor-capacitor network connected to a transistor and a logic circuit implemented in the microcontroller 85. With $S_A$ and $S_{RP}$, the goal is to modify the charging current of the capacitor of the RC network to change the frequency of the relaxation oscillator. If the charging current is low, the voltage of the capacitor increases slowly and when the threshold of the transistor is reached, the capacitor discharges through the transistor. The frequency of the charging-discharging sequence depends on the charging current.

If the external oscillator 86 is a crystal oscillator, signals $S_A$ and $S_{RP}$ modify the capacitor of the resonant circuit. In this case, the crystal oscillator circuit preferably comprises a crystal in parallel with capacitors, so that the crystal and capacitors form a resonant circuit which oscillates at a fixed frequency. This frequency can be adjusted by changing the capacitors. If one of these capacitors is a Varicap (a kind of diode), it is possible to vary its capacitance value by modifying the reverse voltage applied on it, $S_A$ and $S_{RP}$ can be used to modify this voltage.

In either of the foregoing cases, signals $S_A$ and $S_{RP}$ are used to modify at least one parameter of a resistor-capacitor (RC) network associated with the external oscillator 86 or at least one parameter of a crystal oscillator comprising the external oscillator 86.

Referring still to FIG. 105, signals $S_A$ and $S_{RP}$, derived from the stepper motor or from the output of the microcontroller 85, may be used directly for frequency modulation by the external oscillator 86 without any encoding or intervention by the microcontroller 85. By using the external oscillator 86 of the microcontroller 85 as part of the VCO for the feedback signal, no additional components are required, and operation of the microcontroller 85 is not adversely affected by the changes in the oscillator frequency $F_{osc}$. The oscillating signal $F_{osc}$ drives the voltage driven switch 87 for absorption modulation, such that feedback transmission is performed with passive telemetry by FM-AM absorption modulation.

More specifically, signal $F_{osc}$ drives the switch 87 such that during the ON state of the switch 87 there is an increase in energy absorption by the RF-DC converter 88. Accordingly, therefore the absorption rate is modulated at the frequency $F_{osc}$ and thus the frequency of the amplitude modulation of the reflected wave detected by external control 10 contains the information for signal $S_A$. As discussed below, a pickup 89 in the external control 10 separates the reflected wave where it can be decoded by FM demodulation in the demodulator 90 to obtain signal $S_A'$. This method therefore allows the transmission of different signals carried at different frequencies, and has the advantage that the ON state of the switch 87 can be very short and the absorption very strong without inducing an increase in average consumption. In this way, feedback transmission is less sensitive to variation in the quality of coupling between the antennas 83 and 14.

In the external control 10, the feedback signal $F_{osc}$ is detected by the pickup 89 and fed to the FM demodulator 90, which produces a voltage output $V_{OUT}$ that is proportional to $F_{osc}$. $V_{OUT}$ is fed to the filter 91 and the level detector 92 to obtain the information corresponding to the drive element signal $S_A$, which in turn corresponds to the pulses applied to the stepper motor coil. The microprocessor 80 counts these pulses to calculate the corresponding displacement of the tension element 32, which is proportional to the number of pulses.

Signal $V_{OUT}$ also is passed through the analog-to-digital converter 93 and the digital output is fed to the microprocessor 80, where signal processing is performed to detect perturbations of the shape of the feedback signal that would indicate a blockage of the rotor of the stepper motor. The microprocessor 80 stops counting any detected motor pulses when it detects that the drive element is blocked, and outputs an indication of this status. The level detector 94 produces an output when it detects that the demodulated signal $V_{OUT}$ indicates the presence of the reference position signal $S_{RP}$ due to activation of the reference position switch. This output induces a reset of the position of the tension element calculated by the microprocessor 80 in the external control. In this way, a small imprecision, e.g. an offset, can be corrected.

As described above, the external control 10 transmits both energy and commands to the implantable controller circuitry in the antenna/controller pod 23. The external control 10 also receives feedback information from the implantable controller that can be correlated to the position of the tension element 32 and the diameter of the ring 22. As will be apparent to one of skill in the art, the external control 10 and the implantable controller are configured in a master-slave arrangement, in which the implantable controller is completely passive, awaiting both instructions and power from the external control 10.

Pressure Measuring

Measuring the applied pressure via the present ring 22 is very important in ensuring that excessive pressure is not applied to the stomach. As such, the present invention incorporates the ability to measure the applied pressure in a reliable, effective and convenient manner. In accordance with a first embodiment, and with reference to FIGS. 106 and 107, the applied current for the motor 66 is measured and the measured current is utilized in determining the applied pressure and ultimately as a feedback system for measuring the functional state of the gastric band 21.

In accordance with this embodiment, the current is monitored via a closed loop feedback system 1012 integrated into the operation of the mechanical banding system 1 of the present invention. By incorporating an electrical current measurement to measure electrical current being drawn by the motor 66 of the present banding system, the performance of the banding system may be evaluated for determination of, among other features, the applied pressure of the gastric band 21. The current drawn by the motor 66 is directly related to the force being applied by the banding system. Any increase in the force applied by the gastric band 21 is proportionally linked to an increase in current being drawn by the motor 66 of the gastric band 21. In practice, the current measured in accordance with the application of the present invention is correlated to the static force or pressure the ring 22 applies to the stomach tissue it encircles.

In addition to its use in measuring pressure, the monitoring of the applied current may also be utilized in determining any loss of performance of the banding system due to component wear down, corrosion, etc.

Referring to FIG. 107, the closed loop feedback system 1012 includes leads 1016 accessing the current flowing from the power source 1018 to the motor 66. The current is measured using a current sensing circuit 1020 and the output current measurement 1022 is forward to the microcontroller 85 of the present drive element 35 for action in accordance with the goals of the present invention.

In accordance with an alternate embodiment, and with reference to FIG. 108, measurements of the applied current are made using a Hall sensor 1024 positioned about the wire 1026 supplying the motor 66 with electrical power. When a Hall sensor 1024 is positioned above a current carrying wire 1026, it is capable of measuring current flow through the wire 1026 and ultimately the current being drawn for operation of the motor 66 as it constricts the ring 22 to apply pressure to the stomach which the ring 22 surrounds. In accordance with the embodiment disclosed herein, the measured current is derived from a voltage measurement across a series of resistors 1028 in line with the power source 1018 for the motor 66.

Regardless of the whether a hardwired circuit is employed or a Hall sensor is employed, the voltage is calculated by utilizing Ohms Law, that is, V=IR. Assuming a fixed resistance change in current, a current is directly related to the voltage drop across the resistance of the motor 66. A typical sensing voltage might be between 50 mV and 200 mV.

Figure 109:
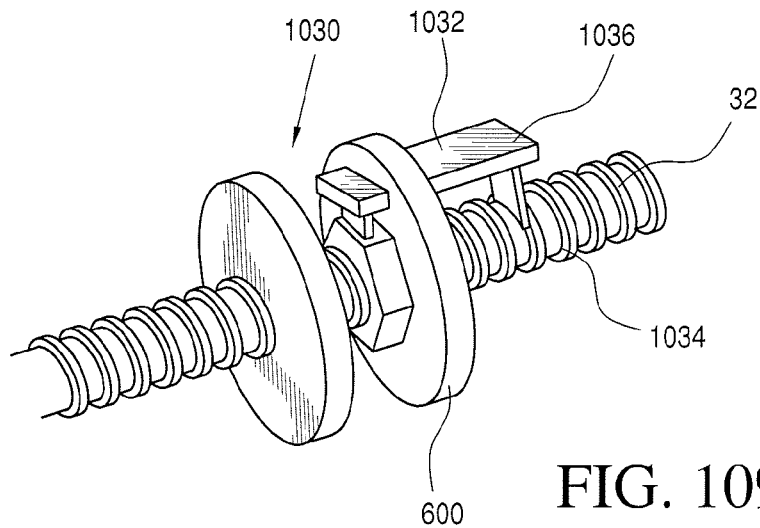

In accordance with an alternate embodiment, and with reference to FIG. 109, the tension applied by the gastric band 21, that is the applied pressure of the gastric band 21, is monitored by a mechanical system 1030. In particular, the tension applied to the flexible tension element 32 is monitored utilizing a strain gauge 1032 acted on by the threading 1034 of the tension element 32. By monitoring the force applied to the strain gauge 1032, the operator is provided with an indication when fail-safe action is necessary.

The strain gage 1032 is preferably coupled to the nut 600 on the drive element housing 53, for example, by means of a cantilevered beam 1036. The interaction of the nut 600 with the threading 1034 of the tension element 32 provides highly accurate force measurements concerning the relationship between the nut 600 and the threading 1034 of the tension element 32. By monitoring the force measurements, the pressure applied by the gastric band 21 is determined and operators of the gastric band 21 are readily able to determine when fail-safe action is necessary based upon a detection of excess tension in the gastric band 21.

Figure 110:
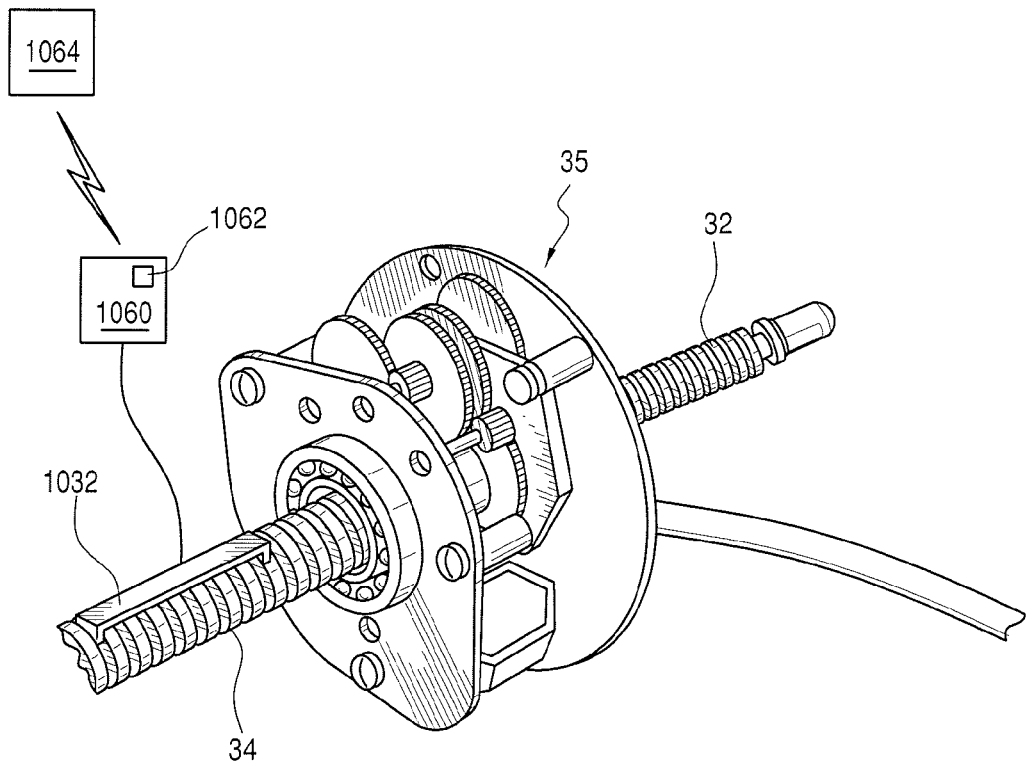

In accordance with a variation of the use of a strain gauge, the strain gauge 1032 may straddle threading on the tension element 32 so as to identify the applied force. See FIG. 110. To identify the applied force the strain gauge output would be connected to a circuit, such as an analog to digital converter (A/D) or microcontroller 1060, that converts the strain into an applied force. The A/D or microcontroller 1060 would provide force data to a telemetry circuit 1062 which in turn would send the data to the external reading device 1064. The applied force could be compared to a force threshold (either dynamic or static) either by the internal circuitry 1060 or by the external reading device 1064 which in turn would provide and indication to the state of the drive mechanism. A higher force/tension in either movement direction may indicate a mechanical failure in the drive mechanism.

As with the prior embodiment, and in addition to its use in measuring tension along the gastric band 21, the monitoring of the force encountered by the strain gauge 1032 may also be utilized in determining any loss of performance of the banding system due to component wear down, corrosion, etc. As such, the strain gauge is preferably linked to a feedback system controlling operation of the drive element 35. It is also contemplated that in addition to a strain gage, position/proximity sensors may be employed, Hall effect sensors may be employed, contact sensors may be employed or a microswitch may be employed.

Figure 111:
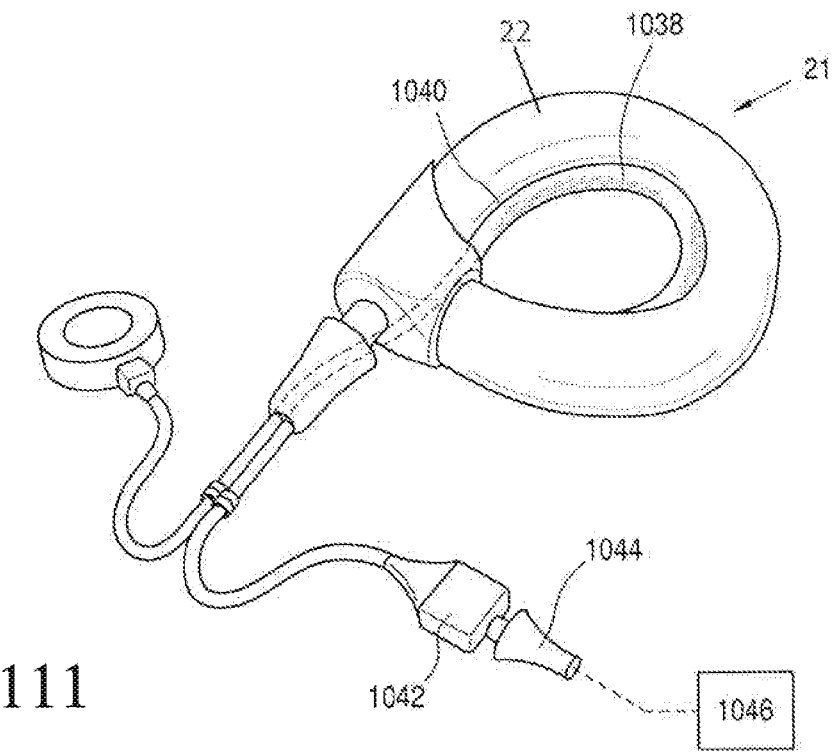

In accordance with yet a further embodiment as shown with reference to FIG. 111, and where a fluid filled bladder 1038 is incorporated along the internal surface 1040 of the ring 22, the pressure of the fluid within the bladder 1038 is measured to provide an indication as to the pressure being applied to the stomach via the present banding system 1.

In accordance with this embodiment, a fluid bladder 1038 is formed along the internal surface 1040 of the mechanical gastric band 21. The fluid bladder 1038 is formed and positioned such that it directly interfaces with tissue. In accordance with a preferred embodiment, the fluid bladder 1038 may be integrally formed with the gastric band or it may be selectively secured thereto for use in accordance with the present invention. As such, and where the fluid bladder 1038 is selectively secured to the gastric band 21, it may be secured to the gastric band 21 prior to or during installation (implantation). A pressure sensor 1042 is linked to the fluid bladder 1038 allowing for remote monitor of the fluid pressure within the bladder 1038.

By constructing the ring 22 in such a manner, not only is a softer tissue interface provided by the fluid bladder 1038, but the inclusion of the fluid bladder 1038 allows for the ability to add a pressure sensor 1042 in the fluid path to measure the fluid pressure in the bladder 1038. When the gastric band 21 is wrapped around the stomach tissue, the monitored pressure within the bladder 1038 relates to the pressure exerted on the tissue. This pressure reading is then used as a primary or secondary feedback to control the applied restriction employed in accordance with the gastric band 21 of the present invention.

In practice, and in accordance with a preferred embodiment as disclosed herein, the bladder 1038 is pre-filled with fluid and calibrated prior to implantation. While pre-implantation calibration is contemplated, it is conceived that calibration may be performed after implantation in accordance with the present invention. As such, the fluid bladder may be adjusted to ensure proper calibration. Such adjustments are achieved by connection of the fluid bladder to a filling tube via a port formed in the fluid bladder. The bladder 1038 is preferably made of silicone or another biocompatible material and is preferably filled with a non-aqueous fluid or gel, for example, silicone or fluoro-silicone oil. The pressure 1042 is preferably a piezoresistive or capacitive sensor designed for implantation in a hermetic package. The pressure 1042 is connected to a telemetry circuit 1044 allowing pressure to be read outside the body using an external reading device 1046.

As with the previously discussed embodiments for measuring the applied pressure of the gastric band 21, the pressure bladder 1038 may also serve as an indicator to the functional state of the mechanical gastric band 21. Pressure should increase when the gastric band 21 is tightened and decrease when the gastric band 21 is loosened. If the mechanical system is not functioning correctly, there will be no change in pressure.

In addition to providing a fail-safe mechanism for operation of the present ring 22, loading information garnered in the manner discussed above, may also be used to aid the surgeon in correctly setting the band's initial degree of restriction during band implantation. That is, the loading information could also be used to help ensure that the band is initially implanted with the correct degree of restrictive adjustment. In this case an indication of tension element loading would provide surgeons (especially novice ones) with an indication of whether they've sufficiently tightened the band onto the tissue to achieve the desired constriction while also making sure that they haven't excessively tightened the band onto the tissue and/or undesirably approached the tension element's yield point.

The load measurements may also be used to prevent over-tightening the band during extended use. In particular, the loading information could also be used in an alternative manner if the band has auto-tightness adjustment capability. In this case the surgeon may or may not be present at the time the tension of the tension element is being adjusted. In this scenario, the load and/or strain measurements could be used to signal the control unit of the motor to either stop tightening the band if a pre-set load threshold is reached or actually reverse the direction of the motor to decrease tension element loading if the threshold has already been exceeded. One way to ensure that the loading threshold is never exceeded is to control the flow of current to the motor using commonly known techniques, such as current clipping, to ensure that the motor is never able to build up enough torque to over-tighten the tension element. Alternatively, an electrical fuse element could be used in conjunction with the current supplied to the motor such that the fuse would trip and either limit or release loads on the tension element if the current supplied to the motor ever exceeds an allowable threshold.

In addition to the measuring techniques discussed above, these benefits could be embodied by use of any of the load measuring techniques, such as, measuring the motor torque. In particular, the tension on the tension element may be derived from motor torque. The algorithm used in this method is well appreciated by those skilled in the art. When using a motor, measure the current drawn of the motor under load, and calculate the torque using the equation below:

$$T = (I - I_{NL}) \times (K_T \times N \times h)$$

Where,
I=Current
T=Torque
$K_T$=Torque Constant
N=Gear Ratio (Equals 1 if there is no gearbox)
h=Gearbox Efficiency (Equals 1 if there is no gearbox)
$I_{NL}$=No-Load Current Please be aware this equation approximates the true load torque and does not take thermal conditions into consideration. The results are reasonably close and suitable for most purposes."

The current may be determined by measuring the current across a shunt resistor in series with the motor at the power source. The microcontroller will measure the voltage across the resistor and convert the value to current using Ohm's Law (I=V/R where I=current, V=voltage and R=Resistance across the shunt resistor) in order to determine torque.

This value may be converted to tension since the tension element is a screw thread or cable.

In general, a representative conversion equation for torque to axial load (cable tension) is:

$$T = DF$$

Where,
T=Torque required
F=Desired cable tension
D=cable thread nominal diameter (major dia)

Since it is not generally recommended that induced stress exceed a safe fraction of the yield strength of the tension element, it may be desirable to introduce a fractional coefficient c (less than or equal to 1) in the equation:

$$T = cDF$$

Expressed in terms of cable tension:

$$F = T/cD$$

Since this relationship is linear, however, any correlations such as those discussed below to band adjustments may be made using torque or tension. Thus, current, torque or cable tension may all be used as an adjustment parameter, much the same as the pressure measurements as described in U.S. Patent Application Publication No. 2006/0211913, entitled "NON-INVASIVE PRESSURE MEASUREMENT IN A FLUID ADJUSTABLE RESTRICTIVE DEVICE", which is incorporated herein by reference.

As discussed above, the tension upon the tension element may be measured by monitoring component strain. The tension may be measured directly via a strain gauge. The strain gauge may be positioned in a number of locations such that the tension would cause a strain, i.e., on the tension element 32 itself, measuring stretch of the tension element 32 (See FIG. 110)
between the rear hub and the nut 60 (see FIG. 109);
between the tension element 32 and an axially grounded portion of the hub.

The strain read by the strain gauge may be translated to tension element 32 tension by the association:

$$\sigma = E\epsilon$$

Where,
$\sigma$=the cable stress=$F_t/A$
$F_t$=the cable tension
A=the cross sectional area of the cable
E=the elastic modulus of the material
$\epsilon$=the strain in the cable
So, $$F_t = E\epsilon A$$

In accordance with yet another embodiment, the strain gauge location could be used as a compressive force gage if the nut is free to translate slightly with the thread. The gauge would be positioned under the nut on the side opposite the direction of translation of the threaded shaft and the nut would impose a compressive force on to the gauge when the band is adjusted. In a manner similar to the tension measured above the force could also be measured with compression as well. Thin film load cells are commercially available and can be found in U.S. Pat. No. 6,272,936. This circuit can be made to fit a very tiny space in-between the nut 60 and the hosing plate.

Figure 112:
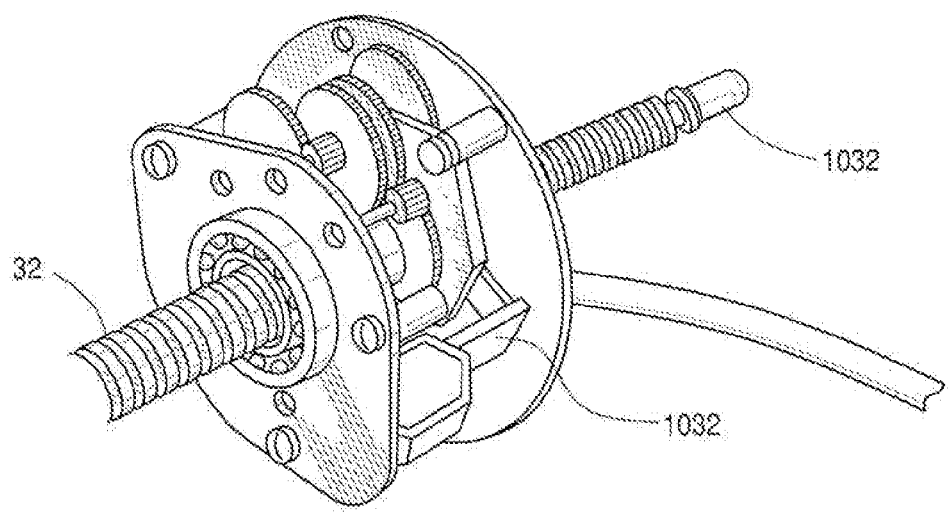

In accordance with yet another embodiment as shown with reference to FIG. 112, the axial loads on the tension element 32 may be measured. In accordance with such and embodiment, the tension force between the end of the spring element (that is the tension member 32), and the threaded shaft at the free end 34 of the tension element 32 is measured. A small transducer 1032 is attached that measures the axial load seen by the threaded shaft as the gastric band 21 is adjusted. This could also be employed at various locations along the tension element 32, such as those indicated by the red circles.

Operational Modes

Figure 103:
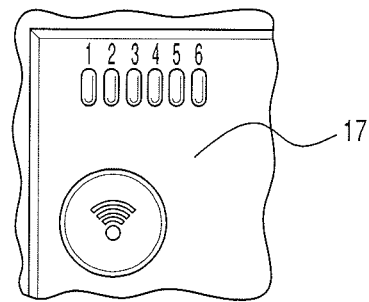
FIG. 103 is a detailed view of the signal strength indicator portion of the remote control of FIG. 1.

Referring to FIG. 103, some of the safety features of the banding system of the present invention are described. As discussed above with respect to FIG. 105, both power and control signals are provided to the implantable controller from the external control 10. Because power is delivered to the implantable controller via magnetic induction, the amount of energy delivered to the controller depends on the quality of the coupling between the external antenna 14 and the antenna circuitry contained within the antenna/controller pod 23.

The quality of the coupling may be evaluated by analyzing the level of the feedback signal received by the external control 10, and a metric corresponding to this parameter may be displayed on the signal strength indicator 17, which includes 6 LEDs (corresponding to six levels of coupling). If the coupling between the antennas 14, 83 is insufficient, the motor 66 of the drive element 35 may not work properly, resulting in an inaccurate adjustment of the gastric band 21.

Accordingly, in a standard mode of operation, adjustment may be made only if the coupling quality is strong enough, as indicated by having at least LED 5 or LED 6 in FIG. 103 illuminated. If, on the other hand, poor coupling exists (e.g., one of the first four LEDs are illuminated) it is still possible to perform some adjustment of the gastric band 21, although the adjustment may be inaccurate.

The design of the external control 10, in combination with the patient microchip card 16 (see FIG. 1), also ensures a high degree of efficacy and safety. First, as contemplated for use with the gastric band 21 of the present invention, the external control 10 is intended primarily for use by a physician in an office or hospital setting, and not by the patient alone. Of course, in alternative embodiments, such as to treat urinary or fecal incontinence, it would be essential to provide an external control 10 for use by the patient. The simplicity of the design of the external control 10 and ease of use would provide no impediment to use by the patient for such embodiments.

As discussed with respect to FIG. 1, patient microchip card 16 stores, among other data, a serial number identifying a corresponding gastric band 21 and the diameter of the ring 22 upon completion of the previous adjustment. When the external control 10 first transmits energy to the implantable controller of the gastric band 21, the gastric band 21 identifies itself to the external control 10. In the standard mode of operation, the serial number stored on the patient microchip card 16 must match that received from the gastric band 21, otherwise no adjustment is permitted.

As a fail-safe, however, the physician still may adjust the gastric band 21 even if the patient has lost or misplaced his microchip card 16. In this case, the external control 10 may be set in a "no card mode". In this mode, the information displayed on the display screen 13 of the external control 10 corresponds only to the relative variation of the gastric band 21 during that adjustment session, and is no longer indicative of absolute diameter. When the physician activates this mode, an emergency bit is set in the memory of the implantable controller to indicate the "no card mode". In subsequent adjustment sessions, the implantable controller will signal that the gastric band 21 was adjusted in the "no card mode" and all further adjustments will be reported on a relative basis. If the patient again locates the microchip card 16, the emergency bit may be cleared by fully opening the gastric band 21 and thus reaching the reference contact, which re-initializes the position. Subsequent adjustments will again be managed in the standard mode of operation.

During adjustment of the ring 22, a physician places the external antenna 14 in a face-to-face position on the skin of the patient relative to the antenna/controller pod 23 of the ring 22, and to receive feedback information from which the constricted diameter of the ring 22 may be computed. In accordance with the principles of the present invention, it is possible to vary the diameter of the ring 22 without having to undertake invasive surgical intervention, and this variation may be carried out at will, because multiple control cycles may be carried out at regular or irregular intervals, solely under the control of the treating physician.

The banding system of the present invention is expected to be particularly reliable, relative to previously-known hydraulic bands that can be adjusted by the patient, because only the physician typically will have access to the external control box needed to adjust the ring. For a ring embodiment intended for treatment of morbid obesity, the patient therefore does not have free access to any means to adjust the diameter of the ring.

Moreover, because the gastric band of the present invention provides a precise readout of the current diameter of the ring in the standard mode of operation, it may not be necessary for the patient to ingest a radiographic material (e.g., barium dye) to permit radiographic visualization of the ring to confirm the adjusted size. The process of adjusting the band accordingly may be carried out in a doctor's office, without the expense associated with radiographic confirmation of such adjustments. In addition, the self-blocking configuration of the tension element and nut, in combination with the mechanical nature of the gastric band, overcome problems associated with previously-known hydraulically actuated gastric band systems.

Methods of Implantation and Removal

Figure 104:
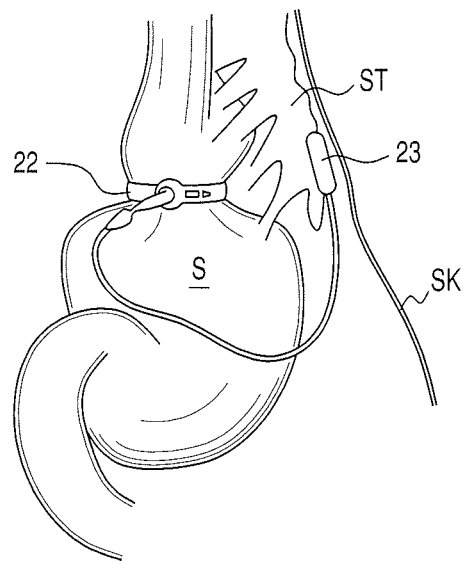
FIG. 104 is a schematic diagram illustrating placement of the implantable portion of the present invention within a patient.

Referring now to FIG. 104, the gastric band 21 of the present invention is shown implanted in a patient. The ring 22 is disposed encircling the upper portion of the patient's stomach S while the antenna/controller pod 23 is disposed adjacent to the patients sternum ST. The antenna/controller pod 23 is located in this position beneath the patients skin SK so that it is easily accessible in the patients chest area to facilitate coupling of the antenna/controller pod 23 to the external antenna 14 of the external control 10 (see FIG. 1).

Other Features

Figure 72:
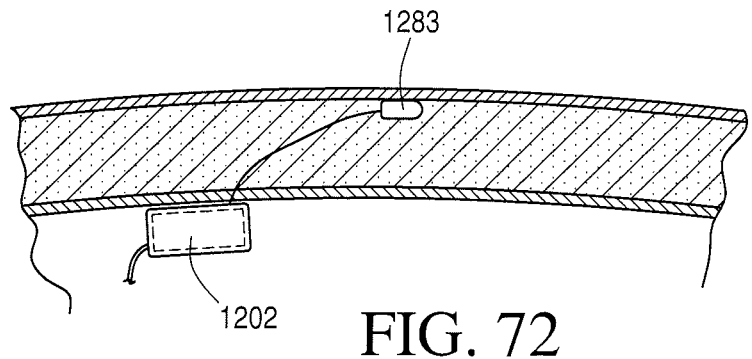
FIG. 72 is a schematic showing an alternate embodiment with a titanium case encasing electronic components of the invention.

In addition to the features discussed above, the present invention provides a mechanism for protecting the implanted electronics from electromagnetic interference (for example, from MRI). In particular, the electronics of the device are encased in a titanium case 1202 (see FIG. 72) and the antenna 1283 is moved external to the titanium case 1202. In this way, the electronics may be implanted deeper into the body cavity, leaving only a thin antenna near the surface of the skin.

In addition, time limit warning on the packaging of the device may be avoided where the gastric band is prefilled with fluid or gel, air would not permeate the silicone. The fluid could be incorporated during manufacturing or injected once the device is opened in the operating room. This would also improve the tissue interface of the gastric band by making it softer.

if the gastric band were shipped in fluid or instructed to place the device in a saline bath when opened, it could stay in place indefinitely.

If the silicone is coated with parylene, titanium or similar compositions to reduce permeation rates thereby increasing the open air time.

If the balloon is left unsealed. Since the band is mechanical and not hydraulic, the balloon has no functional need to be sealed.

As stated in the System Overview portion of the present application, the telemetrically-powered and controlled ring system of the present invention has numerous applications apart from gastric banding for the treatment of morbid obesity. For example, the ring system of the present invention may advantageously be used for the treatment of fecal incontinence, ileostomy, coleostomy, gastro-esophageal reflux disease, urinary incontinence and isolated-organ perfusion.

For treatment of fecal incontinence, the ring may be used with little or no modifications. In addition, because the ring adjustment procedure will be performed by the patient on at least a daily basis, a portable user-friendly external control may be used. In addition, because the ring will regularly be transitioned between the closed and fully opened position, the patient microchip card is unneeded. Instead, the fully closed position may be stored in the memory of the implantable controller, and read by the external remote at each use (subject to periodic change by the physician).

A similarly modified device could be used by patients who have undergone ileostomy or coleostomy, or disposed surrounding the esophageal junction, to treat gastro-esophageal reflux disease.

For treatment of urinary incontinence, the ring may be further modified to minimize the volume of the ring surrounding the urethra by moving the drive element motor to a location elsewhere in the lower abdomen or pelvis, and coupling the drive element to the motor via a transmission cable.

The present invention also may be beneficially employed to perform isolated-organ perfusion. The treatment of certain cancers requires exposure to levels of chemotherapy agents that are too high for systemic circulation. It has been suggested that one solution to this problem is perform an open surgery procedure in which blood flow to the cancerous organ is stopped and quiescent blood replaced by circulation from an external source containing a desired dose of drug. Individual or multiple rings of the present invention may be used as valves to isolate the cancerous organ and permit perfusion of the organ with high doses of drugs. Such procedures could thus be performed on a repetitive basis without surgery, thereby reducing the trauma and the risk to the patient while improving patient outcomes.

Although particular embodiments of the present invention have been described above in detail, it will be understood that this description is merely for purposes of illustration. Further variations will be apparent to one skilled in the art in light of this disclosure and are intended to fall within the scope of the appended claims.

As discussed above, it is possible to make highly accurate load measurements regarding the load applied by the ring in accordance with the present invention. This information may be used to dynamically adjust the band's degree of restriction to optimize weight loss. This may prove helpful to surgeons in making a correlation between tension on the tension element and how tightly the band is tightened on tissue. Much the same as the pressure measurements as described in U.S. Patent Application Publication No. 2006/0211913, entitled "NON-INVASIVE PRESSURE MEASUREMENT IN A FLUID ADJUSTABLE RESTRICTIVE DEVICE", which is incorporated herein by reference; that is, the manner in which pressure magnitude and pulse counting of peristaltic waves is used as a target against which to adjust, the load or strain measurements may be used in a similar fashion as a measure of peristaltic pressure. Such systems are disclosed in U.S. Patent Application Publication No. 2006/01898888, entitled "DEVICE FOR NON-INVASIVE MEASUREMENT OF FLUID PRESSURE IN AN ADJUSTABLE RESTRICTION DEVICE", and U.S. Patent Application Publication No. 2009/0187202, entitled "OPTIMIZING THE OPERATION OF A RESTRICTION SYSTEM", which are also incorporated by reference. Pressure waves from esophageal peristalsis will cause tension changes in the cable which may be read and correlated to proper or improper adjustment. Pulses may be counted from this same means, along with pulse width, duration, etc. Much of the information that can be gained will be able to be derived form the present mechanism.

Multiple methods of storing the measured loads on the band are discloses, which include but are not limited to:
   Storing motor torque;
   Storing mechanical strain;
   Storing compressive and axial loads.

With regard to storing motor torque, the component torque, as described above, may also be stored for later analysis by a torque measuring device (torque watch). Simpler models would just record and store peak values, which may be sufficient for this application. Alternatively, a more complex model would allow for storage of continuously obtained torque information. Due to storage capacity, it is likely that the data would need to be recorded in set increments and be downloaded periodically. Alternately, if the torque was measured indirectly using a DC motor as described above, a multimeter may be used to record and store peak values and/or continuously obtain information which could then be converted to torque via the above equations.

As to storing mechanical strain, the component strain, as described above, may also be stored for later analysis by a strain gauge. Simpler models would just record and store peak values, which may be sufficient for this application. Alternatively, a more complex model would allow for storage of continuously obtained strain information. Due to storage capacity, it is likely that the data would need to be recorded in set increments and be downloaded periodically.

Compressive and axial loads may also be stored, as described above. This information is stored for later analysis by a strain gauge. A basic force gauge may be used to store compressive and axial loads. Simpler models would just record and store peak values, which may be sufficient for this application. Alternatively, a more complex model would allow for storage of continuously obtained torque information.

Stored information to interested parties (i.e., Surgeon, Primary Care Physician (PCP), Patient, etc.) may be relayed to other parties for use at remote locations. With regard to the relay of information to the surgeon/PCP, a surgeon or primary care physician may be interested in obtaining and using the information gathered to make determinations about the restriction provided by the band and/or complications arising from the tightness of the band. As a result, it is desirable that the information measured and stored as described above is also accessible by the surgeon or PCP. One mechanism for achieving this would be to use an external data logger which would be worn by the patient. Information stored in this device could be downloaded by the surgeon or PCP by means of a USB port. For example, see U.S. Patent Application Publication No. 2006/0199997, entitled "MONITORING OF A FOOD INTAKE RESTRICTION DEVICE" and U.S. Patent Application Publication No. 2008/0249806, entitled "DATA ANALYSIS FOR AN IMPLANTABLE RESTRICTION DEVICE AND A DATA LOGGER", which are hereby incorporated by reference.

As to the relay of information to the patient, patients would be interested in obtaining some information about the status of the restriction in their band for various reasons. For example, one reason would be to indicate that there may be a problem with their implant and direct them to visit their surgeon. Since it would probably not be necessary or useful for them to receive numerical information about the torque, strain or load present in their band, a different type of relaying method would be important. One option would be an audible noise (i.e., alarm) which would indicate to them if there was a potential issue with their implant. Alternatively, if they were wearing an external data logger as described above, a visual light (i.e., flashing red or green) could indicate the status of their implant.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. Apparatus for regulating functioning of a patient's organ or duct, comprising:
   an elongated member having a first end and a second end;
   a fastener disposed on the first end of the elongated member, the fastener configured to engage the second end of the elongated member so that the elongated member forms a loop around the organ or duct;

a tension element disposed for movement within the elongated member, the tension element including a free end and a fixed end;

a drive element associated with and engaging the tension element for causing the tension element to control tension applied by the elongated member against a patient's body organ or duct;

a load monitor ensuring that excessive pressure is not applied to the patient's body organ or duct; and a tension element release system, wherein the fixed end of the tension element is secured via a release mechanism allowing selective release of the fixed end of the tension element for release of the applied tension.

2. The apparatus according to claim 1, wherein the load monitor includes a monitoring circuit monitoring current drawn by the drive element.

3. The apparatus according to claim 2, wherein drive element is motor.

4. The apparatus according to claim 2, wherein the monitoring circuit is a closed loop feedback circuit.

5. The apparatus according to claim 4, wherein the monitoring circuit includes leads accessing current flowing from a power source to the motor of the drive element.

6. The apparatus according to claim 5, wherein the monitoring circuit includes a current sensing circuit and output current measurement from the current sensing circuit is forwarded to a microcontroller for control of the drive element.

7. The apparatus according to claim 1, wherein the tension element is slidingly disposed within a substantially cylindrical tube of a compressible material so that when the tension element is pulled through the drive element, the compressible material is compressed and a diameter of opening in the loop is reduced.

8. The apparatus according to claim 7, wherein the compressible material is surrounded on a dorsal face thereof by a dorsal element that is flexible, but sturdier than the compressible material.

9. The apparatus according to claim 8, wherein the dorsal element is silicone.

10. The apparatus according to claim 1, wherein the release mechanism includes a jaw mechanism that selectively engages the fixed end of the tension element.

11. The apparatus according to claim 10, wherein the jaw mechanism includes a jaw drive element for controlled movement of the jaw mechanism.

12. The apparatus according to claim 10, wherein the jaw mechanism includes a first jaw member which is movable and a second jaw member which is movable, the first jaw member and the second jaw member being biased toward each other.

13. The apparatus according to claim 1, wherein the release mechanism includes a first jaw member and a second jaw member with a jaw drive element positioned between the first jaw member and the second jaw member for selectively moving the first and second jaw members between a locked orientation and a released orientation.

14. Apparatus for regulating functioning of a patient's organ or duct, comprising:

an elongated member having a first end and a second end;

a fastener disposed on the first end of the elongated member, the fastener configured to engage the second end of the elongated member so that the elongated member forms a loop around the organ or duct;

a tension element disposed for movement within the elongated member, the tension element including a free end and a fixed end;

a drive element associated with and engaging the tension element for causing the tension element to control tension applied by the elongated member against a patient's body organ or duct;

a load monitor ensuring that excessive pressure is not applied to the patient's body organ or duct; and a tension element release system, wherein the fixed end of the tension element is secured via a release mechanism allowing selective release of the fixed end of the tension element for release of the applied tension, wherein the release mechanism includes a jaw mechanism that selectively engages the fixed end of the tension element and the jaw mechanism includes a jaw drive element for controlled movement of the jaw mechanism, the jaw drive element being a shape memory alloy spring positioned between a first movable jaw member and a second movable jaw member.

15. The apparatus according to claim 14, wherein the shape memory alloy spring is linked to a source of electricity.

* * * * *